US012283351B2

United States Patent
Goddard, III et al.

(10) Patent No.: US 12,283,351 B2
(45) Date of Patent: Apr. 22, 2025

(54) SCREENING METHODS AND RELATED CATALYSTS, MATERIALS, COMPOSITIONS, METHODS AND SYSTEMS

(71) Applicants: CALIFORNIA INSTITUTE OF TECHNOLOGY, Pasadena, CA (US); BOARD OF REGENTS OF THE NEVADA SYSTEM OF HIGHER EDUCATION ON BEHALF OF THE UNIVERSITY OF NEVADA, RENO, Reno, NV (US)

(72) Inventors: William A Goddard, III, Pasadena, CA (US); Alessandro Fortunelli, Pisa (IT); Qi An, Reno, NV (US)

(73) Assignees: CALIFORNIA INSTITUTE OF TECHNOLOGY, Pasadena, CA (US); BOARD OF REGENTS OF THE NEVADA SYSTEM OF HIGHER EDUCATION ON BEHALF OF THE OF THE UNIVERSITY OF NEVADA, RENO, Reno, NV (US)

( * ) Notice: Subject to any disclaimer, the term of this patent is extended or adjusted under 35 U.S.C. 154(b) by 1406 days.

(21) Appl. No.: 16/698,909

(22) Filed: Nov. 27, 2019

(65) Prior Publication Data
US 2020/0168300 A1 May 28, 2020

Related U.S. Application Data

(60) Provisional application No. 62/771,988, filed on Nov. 27, 2018.

(51) Int. Cl.
*B01J 23/745* (2006.01)
*B01J 23/80* (2006.01)
(Continued)

(52) U.S. Cl.
CPC ............ *G16C 20/10* (2019.02); *B01J 23/745* (2013.01); *B01J 23/80* (2013.01); *B01J 23/86* (2013.01);
(Continued)

(58) Field of Classification Search
CPC . B01J 23/745; B01J 23/80; B01J 23/86; B01J 23/89; C01C 1/0411
See application file for complete search history.

(56) References Cited

U.S. PATENT DOCUMENTS 3,770,658 A 11/1973 Ozaki et al.
3,787,335 A 1/1974 Yarrington
(Continued)

FOREIGN PATENT DOCUMENTS

CN 1955722 A 5/2007
CN 102909030 B * 1/2015
(Continued)

OTHER PUBLICATIONS

An, Q., et al., "First-Principles High-Throughput—Screening Catalyst Design for Ammonia Synthesis". Accepted Manuscript.Nov. 27, 2018. 31 Pages (submitted).
(Continued)

*Primary Examiner* — Jun Li
(74) *Attorney, Agent, or Firm* — Steinfl + Bruno LLP

(57) ABSTRACT

Provided herein are screening methods to select catalysts having a desired set of target properties from a reference catalyst, and catalysts so obtained, as well as related catalysts material, composition, methods and systems.

19 Claims, 18 Drawing Sheets

(51) Int. Cl.

| | |
|---|---|
| *B01J 23/86* | (2006.01) |
| *B01J 23/89* | (2006.01) |
| *B01J 35/00* | (2024.01) |
| *B01J 35/30* | (2024.01) |
| *G06F 30/20* | (2020.01) |
| *G16C 20/10* | (2019.01) |
| *G16C 20/30* | (2019.01) |
| *G16C 20/64* | (2019.01) |
| *G16C 60/00* | (2019.01) |
| *C01C 1/04* | (2006.01) |

(52) U.S. Cl.
CPC .............. *B01J 23/89* (2013.01); *B01J 35/19* (2024.01); *B01J 35/391* (2024.01); *G06F 30/20* (2020.01); *G16C 20/30* (2019.02); *G16C 20/64* (2019.02); *G16C 60/00* (2019.02); *C01C 1/0411* (2013.01)

(56) References Cited

U.S. PATENT DOCUMENTS

| | | | |
|---|---|---|---|
| 3,830,753 A | 8/1974 | Ichikawa et al. | |
| 3,951,862 A | 4/1976 | Sze | |
| 4,235,749 A * | 11/1980 | Gens ..................... | C01C 1/0411 502/174 |
| 5,846,507 A * | 12/1998 | Liu ......................... | B01J 23/76 502/247 |
| 6,235,676 B1 | 5/2001 | Jacobsen et al. | |
| 9,150,423 B2 | 10/2015 | Hosono et al. | |
| 2011/0171100 A1* | 7/2011 | Carpenter .............. | B82Y 30/00 423/362 |
| 2012/0082612 A1* | 4/2012 | Carpenter .............. | B01J 23/745 423/362 |
| 2014/0072499 A1* | 3/2014 | Carpenter .............. | B01J 23/745 977/777 |
| 2016/0288114 A1 | 10/2016 | Way et al. | |
| 2018/0093261 A1* | 4/2018 | De Almeida ............ | B01J 37/03 |
| 2020/0197911 A1* | 6/2020 | Beach ..................... | B01J 35/612 |

FOREIGN PATENT DOCUMENTS

| | | | | |
|---|---|---|---|---|
| CN | 105289624 A * | 2/2016 | | |
| EP | 2444154 A1 | 4/2012 | | |
| JP | 2014151290 A * | 8/2014 | ............ | B01J 21/063 |
| WO | WO-2014115582 A1 * | 7/2014 | ............ | B01J 21/066 |
| WO | WO-2018164182 A1 * | 9/2018 | ............. | B01J 23/28 |
| WO | 2020/113136 A1 | 6/2020 | | |
| WO | 2020/113136 A9 | 6/2020 | | |

OTHER PUBLICATIONS

An, Q., et al., "Predictive First-Principles-Based Ammonia Syntesis over Fe Catalysts," Conference presentation abstract.Dec. 4, 2018. 1 Page.

An, Q., et al., "QM-mechanism-based hierarchical high-throughput in silica screening catalyst design for ammonia synthesis," Journal of the American Chemical Society, 140(50): p. 17702-17710.Nov. 27, 2018. 9 Pages.

Bronsted, N., "Acid and basic catalysis," Chem. Rev., 5 (3), 231-338.1928. 108 Pages.

Campbell, C. T., et al., "Equilibrium constants and rate constants for adsorbates: two-dimensional (2D) ideal gas, 2D ideal lattice gas, and ideal hindered translator models," J. Phys. Chem. C., 120 (19), 10283-10297.Apr. 14, 2016. 15 Pages.

Chase Jr., M. W., et al., "NIST-JANAF thermochemical tables, 4th ed.; Journal of Physical and Chemical Reference Data Monograph 9," *American Chemical Society*: Washington, DC,1998.

Chen, B., et al., "Heterogeneous singlewalled carbon nanotube catalyst discovery and optimization," Chem. Mater., 14 (4), 1891-1896.Published on Web Mar. 12, 2002. 6 pages.

Cheng, M.-J. et al., "The critical role of phosphate in vanadium phosphate oxide for the catalytic activation and functionalization of n-butane to maleic anhydride," Journal of the American Chemical Society, 135(12): p. 4600-4603.Feb. 24, 2013. 4 Pages.

Cheng, M.-J., et al., "The Mechanism of Alkane Selective Oxidation by the MI Phase of Mo—V—Nb—Te Mixed Metal Oxides: Suggestions for Improved Catalysts," Topics in Catalysis, 59(17-18): p. 1506-1517.Pub Online Jul. 29, 2016. 13 Pages.

Cheng, T., et al. "Full atomistic reaction mechanism with kinetics for CO reduction on Cu (I00) from ab initio molecular dynamics free-energy calculations at 298 K," Proceedings of the National Academy of Sciences, 114(8): p. 1795-1800.Feb. 21, 2017. 6 Pages.

Chenoweth, K., et al., "Development and application of a ReaxFF reactive force field for oxidative dehydrogenation on vanadium oxide catalysts," The Journal of Physical Chemistry C, 112(37): p. 14645-14654.Published online Jul. 25, 2008. 10 Pages.

Dijkstra, E.W., "A note on two problems in connexion with graphs," Numerische mathematik, 1(1): p. 269-271.1959. 3 pages.

Dupuis, V., et al., "Intrinsic magnetic properties of bimetallic nanoparticles elaborated by cluster beam deposition," *Phys. Chem. Chem. Phys.*,2015, 17, 27996. 11 Pages.

Erisman, J. W., et al., "How a century of ammonia synthesis changed the world," Nat. Geosci., 1, 636-639.Oct. 2008. 4 Pages.

Evans, M. G., et al., "Inertia and driving force of chemical reactions," Trans. Faraday Soc., 34, 11-24.1938. 14 Pages.

Ferrin, P., et al., "Modeling ethanol decomposition on transition metals: a combined application of scaling and Brønsted-Evans-Polanyi relations," *J. Am. Chem.* Soc.,131(16), 5809-5815.2009. 7 Pages.

Fleurat-Lessard, P. et al., "Tracing the minimum-energy path on the free-energy Surface," The Journal of chemical physics, 123(8): p. 084101.Published online Aug. 26, 2005. 18 Pages.

Fortunelli, A., et al., "First-Principles High-Throughput-Screening Catalyst Design for Ammonia Synthesis," Poster presentation for department conference. Dec. 24-26, 2018. 2 Pages.

Foster, S. L., et al., "Catalysts for nitrogen reduction to ammonia," Nature Catal., 1, 490-500.Jul. 2018. 11 Pages.

Fuller, J., et al., "Reaction mechanism and kinetics for ammonia synthesis on the Fe (211) reconstructed surface," *Physical Chemistry Chemical Physics*21: p. 11444- 11454.2019. 11 Pages.

Goddard III, W.A., "Quantum mechanics based mechanisms for selective activation of hydrocarbons by mixed metal oxide heterogeneous catalysts—A tribute to Robert Grasselli," *Catalysis Today*,2019. 7 Pages.

Grasselli, R.K., "Ammoxidation of propylene and propane to acrylonitrile. chapter 5 of RSC Nanoscience & Nanotechnology No. 19 Nanostructured Catalysts: Selective Oxidations," Edited by Christian Hess and Robert Schloegl, in*Royal Society of Chemistry 2011*. Published by the Royal Society of Chemistry,2011. 45 Pages.

Greeley, J., et al., "Computational high-throughput screening of electrocatalytic materials for hydrogen evolution," Nature Mater., 5, 909-913.Nov. 2006. 5 Pages.

Grimme, S., et al., "A consistent and accurate ab initio parametrization of density functional dispersion correction (DFT-D) for the 94 elements H—Pu," The Journal of chemical physics, 132(15): p. 154104. Pub Online Apr. 16, 2010. 20 Pages.

Hakim, S. H., et al., "Synthesis of supported bimetallic nanoparticles with controlled size and composition distributions for active site elucidation," *Journal of Catalysis*328, 75-90.2015. 15 Pages.

Hannemann, S., et al, "Combination of flame synthesis and high throughput experimentation: The preparation of alumina supported noble metal particles and their application in the partial oxidation of methane," *Applied Catalysis A: General*,316, pp. 226-239.Jan. 10, 2007. 14 pages.

Hara, M., et al., "Ru-loaded C12A7:e—electride as a catalyst for ammonia synthesis," ACS Catal, 7 (4), 2313-2324 . . . Feb. 15, 2017. 12 Pages.

Hermes, E.D, et al., "Micki: A python-based object-oriented microkinetic modeling code," The Journal of chemical physics, 151(1): p. 014112.Pub Online Jul. 3, 2019. 14 Pages.

Hoffmann, M.J., et al. Kmos Project: kMC on steroids: A vigorous attempt to make lattice kinetic Monte Carlo modeling as fast as possible. Webpage<http://mhoffman.github.io/kmos/> accessed onJan. 22. 2020. 1 Page.

(56) References Cited

OTHER PUBLICATIONS

Huang, Y., et al., "Identification of the Selective Sites for Electrochemical Reduction of CO to C2+ Products on Copper Nanoparticles by Combining Reactive Force Fields, Density Functional Theory, and Machine Learning," ACS Energy Letters, 3(12): p. 2983-2988. Nov. 8, 2018. 6 Pages.
Hughes, T. F., et al., "Development of accurate DFT methods for computing redox potentials of transition metal complexes: results for model complexes and application to cytochrome," J. Chem. Theory Comput., 8 (2), 442-459. Jan. 13, 2012. 18 Pages.
Iannuzzi, M., et al. "Efficient exploration of reactive potential energy surfaces using Car-Parrinello molecular dynamics," Physical Review Letters, 90(23): p. 238302. Jun. 13, 2003. 4 Pages.
Jacobsen, C.J., et al., "Catalyst design by interpolation in the periodic table: bimetallic ammonia synthesis catalysts," Journal of the American Chemical Society, 123(34): p. 8404-8405.2001. 2 Pages.
Jang, Y.H., et al., "Mechanism of selective oxidation and ammoxidation of propene on bismuth molybdates from DFT calculations on model clusters," The Journal of Physical Chemistry B, 106(23): p. 5997-6013.2002. 17 Pages.
Johnson, E.R et al., "A post-Hartree-Fock model of intermolecular interactions: Inclusion of higher-order corrections," The Journal of chemical physics, 124(17): p. 174104.Pub Online May 5, 2006. 10 Pages.
Jones, D. J., et al., "Discovery and optimization of new chromium catalysts for ethylene oligomerization and polymerization aided by high-throughput screening," J. Am. Chem. Soc., 127 (31), 11037-11046.2005. 10 Pages.
Kresse, G., et al., "Efficient iterative schemes for ab initio total-energy calculations using a plane-wave basis set," Phys. Rev. B, 54 (16), 11169-11186. Oct. 15, 1996. 18 Pages.
Lai, J., et al., "Recent Advances in the Synthesis and Electrocatalytic Applications of Platinum-Based Bimetallic Alloy Nanostructures," *ChemCatChem*,2015. 3206-3228. 23 Pages.
Laio, A., "Escaping free-energy minima," Proceedings of the National Academy of Sciences, 99(20): p. 12562-12566. Oct. 1, 2002. 5 Pages.
Li, L., et al., "Computational identification of descriptors for selectivity in syngas reactions on a Mo2C catalyst," ACS Catal., 5 (9), 5174-5185.Jul. 24, 2015. 12 Pages.
Ling, T., et al., "Icosahedral face-centered cubic Fe nanoparticles: facile synthesis and characterization with aberration-corrected TEM," *Nano letters*,9(4): p. 1572-1576.2009. 5 Pages.
Lum, Y., et al., "Electrochemical CO reduction builds solvent water into oxygenate products," Journal of the American Chemical Society,140(30): p. 9337-9340.Jul. 16, 2018. 4 Pages.
McDonald, M., et al., "Highly Efficient Ni-Doped Iron Catalyst for Ammonia Synthesis from QM-Based Hierarchical High Throughput Catalyst Screening," *The Journal of Physical Chemistry C*,. 123: p. 17375-17383.Jun. 20, 2019. 16 Pages.
Mittasch, A., et al., "Early studies of multicomponent catalysts," Adv. Catal, 2, 81-104.1950. 25 Pages.
Montemore, M. M., et al., "Scaling relations between adsorption energies for computational screening and design of catalysts," Catal. Sci. Technol., 4, 3748-3761.2014. 14 Pages.
Mortensen, J.J., et al., "Nitrogen adsorption and dissociation on Fe (I I I).*Journal of Catalysis*," 182(2): p. 479-488.1999. 10 Pages.
Nørskov, J.K., et al., "Towards the computational design of solid catalysts," Nature chemistry, 1(1): p. 37-46.Apr. 2009. 10 Pages.
O'Neill, B. J., "Catalyst Design with Atomic Layer Deposition," *ACS Catal.* 2015, 5, 1804-1825.Published Feb. 6, 2015. 22 Pages.
Perdew, J.P., et al., "Generalized gradient approximation made simple," Physical review letters, 77(18): p. 3865-3868.Oct. 28, 1996. 4 Pages.
Perdew, J.P., et al., "Generalized gradient approximation made simple," Physical review letters, 78: p. 1396-1396.Feb. 17, 1997. 2 Pages.

Piccolo, L., et al., "Understanding and controlling the structure and segregation behavior of AuRh nanocatalysts," *Scientific reports*, 6: p. 35226.2016.
Qian, J., et al, "Effect of Co doping on mechanism and kinetics of ammonia synthesis on Fe (III) surface," Journal of Catalysis. 370: p. 364-371.Available online Jan. 22, 2019. 8 Pages.
Qian, J., et al., "Reaction mechanism and kinetics for ammonia synthesis on the Fe (III). surface," Journal of the American Chemical Society, 140(20): p. 6288-6297.Apr. 27, 2018. 10 Pages.
Regalbuto, J.R. Catalyst preparation: Science and engineering, CRC Press/Taylor & Francis Group, LLC, Boca Raton, FL,2007. 140 Pages.
Sabatier, P., "Hydrogenations et deshydrogenations par catalyse," Ber. Dtsch. Chem. Ges, 44 (3), 1984-2001. 1911.19 Pages.
Schlögl, R., "Catalytic synthesis of ammonia—a 'never-ending story'?" Angew. Chem., Int. Ed, 42 (18), 2004-2008.2003. 5 Pages.
Senftle, T.P., et al., "The ReaxFF reactive force-field: development, applications and future directions," npj Computational Materials. 2: p. 15011.Published Online Mar. 4, 2016. 14 Pages.
Somorjai, G.A., et al., "Surface structures in ammonia synthesis," Topics in Catalysis, 1(3-4): p. 215-231.1994. 19 Pages.
Stamatakis, M., "Kinetic modelling of heterogeneous catalytic systems," Journal of Physics Condensed Matter, 27(1): p. 013001. Published Nov. 13, 2014. 30 Pages.
Stochastic Parallel PARticle Kinetic Simulator (SPPARKS). Kinetic Monte Carlo Simulator webpage< Simulatorspparks.sandia.gov accessed onJan. 22, 2020. 2 Pages.
Wales, D. J., "Energy landscapes: calculating pathways and rates," Int. Rev. Phys. Chem., 25, 237-282.2006. 47 Pages.
Wang, D., et al., "Bimetallic Nanocrystals: Liquid-Phase Synthesis and Catalytic Applications," *Adv. Mater.*, 23, 1044-1060.2011. 17 Pages.
Wikipedia, "Atomic radius," available online at< web.archive.org web="" 20190331021653=""< a=""href="https://en.wikipedia.org/wiki/Atomic_radius>">https://en.wikipedia.org/wiki/Atomic_radius./web.archive.org>Last edited Mar. 2019. Accessed on Jan. 2020.
Wikipedia, Ethylene oxide. Available online< web.archive.org web= "" 20170314133026=""< a =""href="https://en.wikipedia.org/wiki/Ethylene_oxide">https://en.wikipedia.org/wiki/Ethylene_oxide</web.archive.org>Last modified Mar. 7, 2017. Accessed Jan. 2, 2020.
Wikipedia, Steam reforming. Available online< web.archive.org web="" 20170412014610=""< a="" href="https://en.wikipedia.org/wiki/Steam_reforming,">https://en.wikipedia.org/wiki/Steam_reforming, </web.archive.org>Last modified Apr. 6, 2017. Accessed Jan. 7, 2020. 4 Pages.
Wolcott, C.A., et al., "Degree of rate control approach to computational catalyst screening," Journal of catalysis, 330: p. 197-207. Available online Aug. 3, 2015. 11 Pages.
Xiao, H., et al., "Atomistic mechanisms underlying selectivities in CI and C2 products from electrochemical reduction of CO on Cu (III)," Journal of the American Chemical Society, 139(1): p. 130-136.Dec. 7, 2016. 7 Pages.
Zaffran, J., et al., "Trade-off between accuracy and universality in linear energy relations for alcohol dehydrogenation on transition metals," J. Phys. Chem. C, 119 (23), 12988-12998. May 18, 2015. 11 Pages.
Zhang, H., et al., "Catalytically highly active top gold atom on palladium nanocluster," *Nature Materials*, vol. 11, pp. 49-52.Jan. 2012. 4 Pages.
Written Opinion for International PCT Application No. PCT/US2019/063799 filed on Nov. 27, 2019. Filed on behalf of California Institute of Technology. Mail Date: May 6, 2020. 6 Pages.
International Preliminary Report on Patentability for International PCT Application No. PCT/US2019/063799 filed on Nov. 27, 2019 filed on behalf of California Institute of Technology. Mail Date: Jun. 10, 2021. 8 Pages.
International Search Report for International PCT Application No. PCT/US2019/063799 filed on Nov. 27, 2019. Filed on behalf of California Institute of Technology. Mail Date: May 6, 2020. 5 Pages.

(56) References Cited

OTHER PUBLICATIONS

Alia, S.M. et al. "Galvanic Displacement as a Route to Highly Activeand Durable, Extended Surface Electrocatalysts" Catal. Sci. Technol., 2014, 4, 3589-3600 DOI: 10.1039/C4CY00736K. 13 pages.

An, Q. et al., "Si-Doped Fe Catalyst for Ammonia Synthesis at Dramatically Decreased Pressures and Temperatures" J. Am. Chem. Soc. 2020, 142, 8223-8232. 10 pages.

Definition from Wiktionary—kinked. 2014. https://en.wiktionary.org/w/index.php?title=kinked&oldid=28749736. 2 pages.

Definition from Wiktionary—outmost. 2014. https://en.wiktionary.org/w/index.php?title=outmost&oldid=27557237. 2 pages.

Definition from Wiktionary—stepped. 2014. https://en.wiktionary.org/w/index.php?title=stepped&oldid=31045931. 2 pages.

Fuller, J. et al. "Discovery of Dramatically Improved Ammonia Synthesis Catalysts through Hierarchical High-Throughput Catalyst Screening of the Fe(211) Surface" Chemistry of Materials 2020 32 (23), 9914-9924DOI: 10.1021/acs.chemmater.0c02701. 11 pages.

Fuller, K. et al. "Reaction Mechanisms, Kinetics, and Improved Catalysts for Ammonia Synthesis from Hierarchical High Throughput Catalyst Design" Accounts of Chemical Research 2022 55 (8), 1124-1134 DOI: 10.1021/acs.accounts.1c00789. 11 pages.

Ritala, M. et al. "Atomic Layer Deposition" Department of Chemistry, University of Helsinki. 2002 Chapter 2. ISBN 0-12-512909-2. 57 pages.

Wikipedia "Reactivity Series" The Wayback Machine, 2018. https://web.archive.org. 5 pages.

Fuller, J. et al. "Vibrational Spectroscopy Signatures of Catalytically Relevant Configurations for N2 Reduction to NH3 on Fe Surfaces via Density Functional Theory" J. Phys. Chem. C 125 (51):27919-27930 (2021) DOI: 10. 1021/acs.jpcc.1c08829. 32 pages.

Hagen S, et al. "New efficient catalyst for ammonia synthesis: barium-promoted cobalt on carbon". Chem Commun., (Cambridge). The Royal Society of Chemistry. 2002 pp. 1206-12077. doi: 10.1039/b202781j.

* cited by examiner

A Table 1 - extract

| Element | barrier-1 | barrier-2 | barrier-3 | barrier-4 | barrier-5 | Rate ($S^{-1}$, 673 K) |
|---|---|---|---|---|---|---|
| Rh | 1.51 | 1.60 | 1.31 | 1.44 | 1.60 | 14.61 |
| Pt | 1.55 | 1.59 | 1.36 | 1.60 | 1.60 | 14.61 |
| Pd | 1.51 | 1.63 | 1.42 | 1.51 | 1.63 | 8.71 |
| Cu | 1.64 | 1.61 | 1.56 | 1.52 | 1.64 | 7.33 |
| Ni | 1.60 | 1.39 | 1.48 | 1.53 | 1.68 | 3.68 |
| Fe | 1.68 | 1.57 | 1.53 | 1.43 | 1.68 | 3.68 |

B Table 2 – Table 1 as modified by including semi-empirical corrections

| Element | barrier-1 | barrier-2 | barrier-3 | barrier-4 | barrier-5 | Rate ($S^{-1}$, 673 K) |
|---|---|---|---|---|---|---|
| Rh | 1.76 | 1.60 | 1.48 | 1.44 | 1.76 | 0.93 |
| Pt | 1.34 | 1.59 | 1.07 | 1.02 | 1.59 | 17.36 |
| Pd | 1.44 | 1.63 | 1.27 | 1.23 | 1.63 | 8.71 |
| Cu | 1.51 | 1.61 | 1.36 | 1.31 | 1.61 | 12.30 |
| Ni | 1.55 | 1.39 | 1.35 | 1.31 | 1.63 | 8.71 |
| Cd | 1.14 | 1.84 | 1.14 | 1.09 | 1.84 | 0.23 |
| Ag | 1.31 | 1.81 | 1.21 | 1.16 | 1.81 | 0.39 |
| Zn | 1.36 | 1.79 | 1.23 | 1.19 | 1.79 | 0.55 |
| Au | 1.00 | 1.82 | 0.78 | 0.77 | 1.82 | 0.33 |
| Ir | 1.75 | 1.88 | 1.32 | 1.27 | 1.88 | 0.12 |
| Co | 1.75 | 1.51 | 1.51 | 1.47 | 1.92 | 0.06 |
| Fe | 1.98 | 1.57 | 1.75 | 1.71 | 1.98 | 0.02 |

FIG. 16

|  | T=673, $pH_2$=15, $pN_2$=5, $pNH_3$=1 – pure Fe(111) | | | T=673, $pH_2$=15, $pN_2$=5, $pNH_3$=1 – Rh-Fe(111) | | | T=673, $pH_2$=6.5, $pN_2$=5, $pNH_3$=1 – Rh-Fe(111) | | |
|---|---|---|---|---|---|---|---|---|---|
| configuration | $t_i$ (%) | $-\ln(P_i/P_0)$ | $\Delta G$ | $t_i$ (%) | $-\ln(P_i/P_0)$ | $\Delta G$ | $t_i$ (%) | $-\ln(P_i/P_0)$ | $\Delta G$ |
| 3N_NH$_2$ | 14.8 | 0.00 | 0.00 | 4.3 | 0.00 | 0.00 | 31.0 | 0.00 | 0.00 |
| 3N_H | 3.14 | 0.09 | 0.08 | 0.6 | 0.11 | 0.09 | 2.4 | 0.15 | 0.14 |
| 2N_NH$_2$_H | 62.1 | -0.08 | -0.05 | 0.6 | 0.11 | 0.12 | 1.1 | 0.20 | 0.22 |
| 2N | 2E-5 | 0.78 | 0.80 | 4E-5 | 0.67 | 0.67 | 6E-5 | 0.76 | 0.77 |
| 4N | 0.44 | 0.20 | -0.42 | 4E-2 | 0.27 | -0.36 | 0.7 | 0.22 | -0.26 |
| 2N_2H | 2.65 | 0.10 | 0.12 | 2.3 | 0.04 | 0.04 | 1.6 | 0.17 | 0.18 |
| 2N_2H_lin | 8.5 | 0.03 | 0.06 | 90.2 | -0.18 | -0.18 | 60.6 | -0.04 | -0.03 |
| 2N_NH2_2H | 8.2 | 0.03 | 0.07 | 1.2 | 0.07 | 0.09 | 1.3 | 0.18 | 0.21 |
| NH$_3$ mol/s/(2x2) | 4.6 | | | 9.7 | | | 15.3 | | |
| total time (s) | 530 | | | 3702 | | | 3342 | | |
| total NH$_3$ mol | 2441 | | | 35980 | | | 50996 | | |
| 3N_NH$_3$_H ↔ 3N_H | 1231 | | | 18000 | | | 25508 | | |
| 2N_NH$_3$_H ↔ 2N_H | 1210 | | | 17980 | | | 25488 | | |

FIG. 17

SCREENING METHODS AND RELATED CATALYSTS, MATERIALS, COMPOSITIONS, METHODS AND SYSTEMS

CROSS REFERENCE TO RELATED APPLICATIONS

The present application claims priority to U.S. Provisional Application No. 62/771,988, entitled "First-Principles Hierarchical High-Throughput-Screening (FP-HHTS) Invention For In Silico Design Of Novel High Performance Multi-component Catalysts And Reactive Systems" filed on Nov. 27, 2018, the content of which is incorporated herein by reference in its entirety.

STATEMENT OF GOVERNMENT GRANT

This invention was made with government support under Grant No. DE-AC07-05ID14517 awarded by the Department of Energy. The government has certain rights in the invention.

FIELD

The present disclosure relates to a screening method that can be used to design and/or select component catalysts with a desired performance and catalysts obtained thereby. In particular, the present disclosure relates to screening methods and in particular, computer-based screening methods, related catalysts, materials, compositions, methods and systems

BACKGROUND

Catalysts' properties and their optimization have been at the center of various efforts to improve catalytic systems and related methods and composition. In particular, a common procedure is based on adding alloying elements into a given catalyst therefore achieving multi-component systems to optimize its performance.

Despite progresses made in the recent years, however, achieving catalyst with desired properties is still challenging in particular with reference wet bench and in silico methods which require time and resources to identify features of the desired catalyst which can make the related development impracticable if not impossible.

SUMMARY

Provided herein are a screening method and related catalysts, materials, compositions methods and systems, which are based on hierarchical screening of the activity of candidate catalysts for a target chemical reaction to select active catalyst with desired target properties for the target reaction, in a significantly reduced amount of time with respect to existing approaches.

In particular, a screening method according to the present disclosure is a computer based method of screening for activity alone or in combination with stability and/or selectivity for a target chemical reaction under a target condition, in which a plurality of candidate catalysts having structural and/or compositional difference with respect to a reference catalyst of the target chemical reaction are hierarchically screened with respect to a rate-limiting step of the target chemical reaction under the target reaction condition.

Accordingly, according to a first aspect a computer based method is described of screening for activity alone or in combination with stability and/or selectivity for a target chemical reaction under a target condition, a plurality of candidate catalysts having structural and/or compositional difference with respect to a reference catalyst of the target chemical reaction The method comprises hierarchically screening the plurality of candidate catalysts for activity alone or in combination with stability and/or selectivity for a target chemical reaction under a target condition, the hierarchically screening performed with respect to a rate-limiting step of the target chemical reaction under the target reaction condition, to provide a selected active catalyst optionally stable and/or selective for the target chemical reaction, the selected active catalyst having a reaction rate under the target reaction conditions higher than the reaction rate of the reference catalyst.

According to a second aspect, a computer-based method is described of hierarchically screening for activity for a target chemical reaction under a target condition, of a plurality of candidate catalysts having structural and/or compositional difference with respect to a reference catalyst of the target chemical reaction. The method comprises determining rate-limiting steps of the chemical reaction under the target reaction condition, by analyzing a free-energy diagram of the reference catalyst;

ranking said rate-limiting steps according to their energy barrier values in a descending order to provide ranked rate-limiting steps;

defining a plurality of criteria according to the ranked rate-limiting steps to estimate a change on an energy barrier value of each rate-limiting step caused by the structural and/or compositional difference of each candidate catalyst with respect to the reference catalyst;

for each candidate catalyst, evaluating, on a computer, each criterion of the plurality of criteria sequentially in the descending order to provide rate_selected candidate catalysts, wherein candidate catalysts having a negative change on the energy barrier value of a rate-limiting step in a criterion are evaluated in a next criterion;

constructing, on a computer, a free-energy diagram for each rate selected_candidate catalyst and performing a time evolution simulation method, on a computer, for each candidate catalyst to obtain a reaction rate of each selected candidate catalyst; and further selecting the rate selected_candidate catalysts having a reaction rate for the target chemical reaction higher than the reaction rate of the reference catalysts under the target reaction condition to provide a rate selected active catalyst for the chemical reaction under the target condition.

According to a third aspect, a computer-based method is described of hierarchically screening activity, and stability in a target chemical reaction under a target reaction condition of a plurality of candidate catalysts having structural and/or compositional difference with respect to a reference catalyst of the target chemical reaction. The method comprises:

hierarchically screening the plurality of candidate catalysts for activity for the target chemical reaction under the target condition, by performing a computer-based method according to the second aspect of the present disclosure, further comprising testing on a computer, stability of the candidate catalysts, to select candidate catalysts having a stable configuration before the evaluating;

testing on a computer, stability of the rate selected candidate catalysts, to select rate selected candidate catalysts having a stable configuration before the constructing and/or the selecting; and/or testing on a computer, stability of the rate-selected active catalyst, to further select rate selected active catalyst having a stable configuration, to provide rate-selected active catalyst stable for the chemical reaction under the target condition.

According to a fourth aspect, a computer-based method is described for hierarchically screening activity and selectivity for a target chemical reaction under a target reaction condition of a plurality of active catalysts having structural and/or compositional difference with respect to a reference catalyst of the target chemical reaction. The method comprises providing a plurality of rate-selected active catalysts for the chemical reaction under the target condition by hierarchically screening a plurality of candidate catalysts with a computer-based method according to the second aspect of the present disclosure, each rate-selected active catalyst having a target reaction rate;

for each rate-selected active catalyst, constructing, on a computer, a free-energy diagram of a second chemical reaction different from the target chemical reaction and performing a time evolution simulation method on a computer to obtain a second reaction rate of each rate-selected active catalyst;

obtaining a selectivity ratio between the target reaction rate and the second reaction rate of each rate-selected active catalyst; and selecting the rate-selected active catalyst having a selectivity ratio greater than 1 to provide a rate-selected active catalyst selective for the chemical reaction under the reaction condition.

According to a fifth aspect, a computer-based method is described for hierarchically screening activity, stability and selectivity for a target chemical reaction under a target reaction condition of a plurality of active catalysts having structural and/or compositional difference with respect to a reference catalyst of the target chemical reaction. The method comprises providing a rate-selected active catalyst selective for the target chemical reaction under the target condition by hierarchically screening activity and selectivity of a plurality of active catalysts with a method according to the fourth aspect of the present disclosure testing, on a computer, stability of the candidate catalysts, to select candidate catalysts having a stable configuration before the evaluating, testing on a computer, stability of the rate selected candidate catalysts, to select rate selected candidate catalysts having a stable configuration before the constructing and/or the selecting;

testing on a computer, stability of the rate selected catalyst before or after selecting the rate-selected active catalyst having a selectivity ratio greater than 1, to further select rate selected catalyst having a stable configuration, to provide stable rate-selected active catalyst selective for the chemical reaction under the target condition According to a sixth aspect, a multicomponent iron catalyst for synthesis of ammonia from $N_2$ and $H_2$ is described.

The multicomponent iron catalyst for synthesis of ammonia from $N_2$ and $H_2$ comprise a three layers structure having a Formula (I)

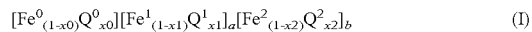

$$[Fe^0_{(1-x0)}Q^0_{x0}][Fe^1_{(1-x1)}Q^1_{x1}]_a[Fe^2_{(1-x2)}Q^2_{x2}]_b \qquad (I)$$

in which $Fe^0$, $Fe^1$, and $Fe^2$ represent an iron atom on an outmost first layer, an iron atom on a second layer, and an iron atom on third layer of an iron crystal or iron film, respectively;

$Q^0$, $Q^1$, and $Q^2$ represent at least one dopant on the outmost first layer, at least one dopant on the second layer, and at least one dopant on the third layer of the iron crystal, respectively;

x0, x1, and x2 represent an atom percentage concentration of the at least one dopant on top layer, an atom percentage concentration of the at least one dopant on second lay, and an atom percentage concentration of the at least one dopant on third layer of an iron crystal, respectively;

(1-x0), (1-x1), and (1-x2) represent an atom percentage of the iron atom in the outmost first layer, an atom percentage of the iron atom on second layer, and an atom percentage of the iron atom on third layer of an iron crystal, respectively; and a, and b respectively represent a number of total atoms on second layer, and a number of total atoms on third layer relative to a number of total atoms top layer, wherein x0, x1, and x2 each range independently from 0 to 0.4 with the proviso that at least one of x0, x1 and x2 ranges from 0.2 to 0.4, and wherein a and b independently range from 0.5 to 2.

According to a seventh aspect, a multicomponent iron catalyst material is described. The multicomponent iron catalyst material comprises a multicomponent iron catalyst for synthesis of ammonia from $N_2$ and $H_2$ comprising a multicomponent iron catalyst having a Formula (I) herein described wherein the outmost first layer of the iron crystal or iron film is presented on a surface of the multicomponent iron catalyst material, wherein the third layer of the iron crystal or iron film is deposited on a substrate comprising a base layer comprising or consisting of at least three layers of iron atoms, wherein the substrate is anchored on a suitable solid support for a catalysis process.

The screening methods and related catalysts, materials, compositions methods and systems herein described allow in several embodiments, to perform hierarchical high-throughput screening that simplifies the analysis of the overall catalytic process by singling out the rate-determining mechanistic steps on which effort should be concentrated to achieve acceleration.

In particular, the screening methods and related catalysts, materials, compositions methods and systems herein described allow, in several embodiments, to perform optimizing and testing of candidate catalysts with only 1% of the computational effort required for a quantum mechanics based calculation (including QM based reactive force field) of the full mechanism for each dopant The screening methods and related catalysts, materials, compositions methods and systems herein described allow in several embodiments, to perform optimizing and testing of candidate catalysts with computational costs at least one order of magnitude lower than would be required to calculate the full mechanism for each dopant.

The screening methods and related catalysts, materials, compositions methods and systems herein described allow, in several embodiments, to identify catalysts with reaction rates 3-50 times increased compared to a reference catalyst with retained or improved stability and improved stability.

The screening methods and related catalysts, materials, compositions methods and systems herein described allow in several embodiments, to optimize catalysts that can drastically reduce the extreme conditions of industrial ammonia synthesis (HB) process, typically held at 773-823 K and total pressure of 150-250 atm, by reducing temperature by 100-150 K and pressures by a factor of 10 or more.

The screening methods and related catalysts, materials, compositions methods and systems herein described allow in several embodiments, to obtain catalysts that can have significantly increased turnover frequency or selectivity by a factor of at least 1.5 and in some cases by a factor of 50 or more.

The screening methods and related catalysts, materials, compositions methods and systems herein described allow in several embodiments, to design active stable and selective multilayer catalysts comprising dopants with a predicted predominant location of the dopants in the outer layers of the catalyst. Accordingly screening methods of the disclosure enable selection of dopants to enhance activity and/or selectivity of a reference multicomponent catalyst which is not achievable with existing methods.

The screening methods and related catalysts, materials, compositions methods and systems herein described can be used in connection with applications wherein improved and in particular optimization of the activity, selectivity and/or stability of existing active catalysts are desired. Exemplary applications comprise industrial catalysis applications, in particular when directed to synthesize a product such as feedstock chemicals (e.g. maleic anhydride or acrylonitrile), non-fossil fuels applications such as production of formaldehyde, ethanol, acrylonitrile which are valuable industrial products in the field of polymer, pharmaceutical applications, in particular when directed to the functionalization of molecules to synthesize potential drug candidates, agricultural chemistry applications, in particular when directed to synthesize pesticides and herbicides as well as fertilizers, petrochemical application in particular when directed to synthesize and functionalize hydrocarbon-based fuels, and other applications that will be apparent to the skilled person upon a reading of the present disclosure.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 16 shows in one embodiment a pictorial illustration of (panel A) Table 1 is an extract of Table 5 of the exemplary section, and (panel B) Table 2 corresponding to Table 1 modified by including the empirical corrections discussed in the detailed description [1]. Barriers of rate-determining steps in ammonia synthesis over pure and doped Fe(111) surface are estimated via the Brønsted-Evans-Polanyi (BEP) principle. Barrier-5 corresponds to the maximum of barrier (1-4) plus the stability penalty term. Rightmost column is the expected $NH_3$ production rate per (2×2) unit cell per second.

FIG. 17 shows a table listing on the top rows—Percent of populations (i.e., residence times)=$t_i$(%), apparent free energy differences [evaluated as minus the logarithm of ratio of populations=$P_i/P_0$, where $P_0=P_{3N\_NH2}$], and thermodynamic free energy differences ($\Delta G$) for selected configurations in a pure or Rh-doped Fe(111)-(2×2) unit cell under steady-state of ammonia synthesis as predicted by kinetic Monte Carlo kMC simulations at 673 K and different $H_2$, $N_2$, $NH_3$ pressures using data from DFT/PBE-D3 [1]. All configurations are assumed in the zigzag arrangement, except for "2N_2H_lin" which is linear. Temperature in Kelvin, pressure in atmospheres, free energy differences in eV. Bottom rows—$NH_3$ molecules produced per second per (2×2) unit cell under the given conditions [$NH_3$ mol/s/(2× 2)], total simulation time, total number of $NH_3$ molecules produced in the kMC runs (total $NH_3$ mol), further partitioned into the 2 main steps involving $NH_3$ adsorption/desorption: 3N_NH$_3$_H->3N_H; 2N_NH$_3$_H->2N_H.

DETAILED DESCRIPTION

Figure 1:
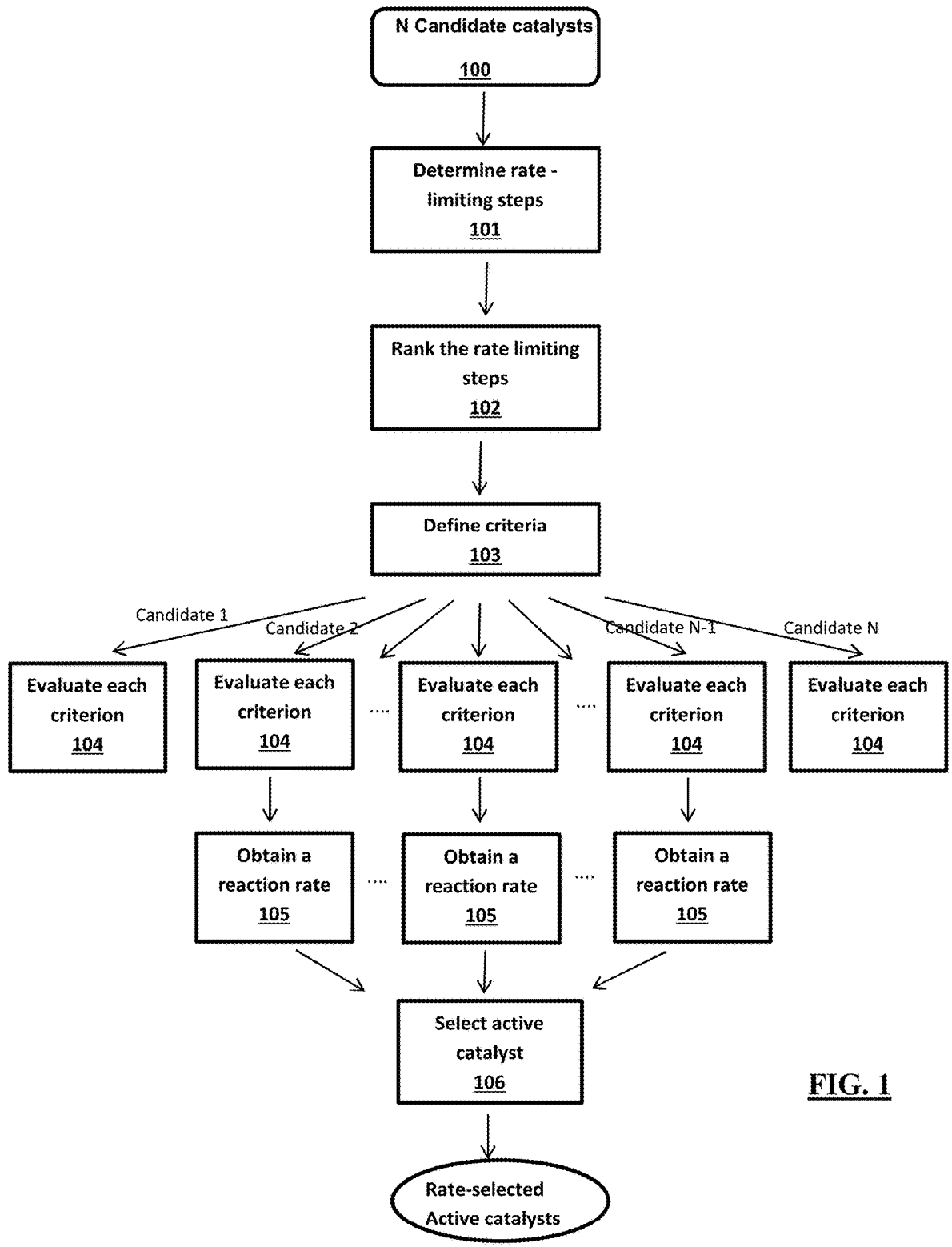
FIG. 1 provides a control-flow diagram that represents one implementation of the first-principles hierarchical high-throughput screening method herein described for active catalysts and its application for optimizing a reference catalyst for a higher reaction rate.

Provided herein are a screening methods and related catalysts, materials, compositions methods and systems based which in several embodiments can be used to provide a catalyst for a target chemical reaction with desired target properties and enhanced activity with respect a reference catalyst under target reaction conditions.

The term "catalyst" in the sense of the disclosure refers to any substance that increases the rate of a chemical reaction without itself undergoing any permanent chemical change. In particular, a catalyst in the sense of the disclosure indicates a substance that provides a reaction pathway with a lower activation energy than a non-catalyzed reaction pathway thus resulting in a chemical reaction having a faster reaction rate with respect to the non-catalyzed reaction. Catalysts typically comprise an active site which indicates an ensemble of atoms of the catalyst that is directly involved in catalyzing a chemical reaction as will be understood by a skilled person. Catalysts' active site comprise selected group of atoms within the catalyst, such as a planar exposed metal surface, a crystal edge with imperfect metal valence or a combination of the two in a heterogeneous catalyst where most of the volume, and/or the surface of the heterogeneous catalyst may be catalytically inactive, as will be understood by a skilled person.

Catalysts in the sense of the disclosure comprise heterogeneous catalysts (not dispersed in the same phase of the reactant and typically a solid substance adsorbing reactants in liquid or gaseous phase), homogeneous catalysts (dispersed in the same phase of the reactants, typically gas or liquid) and enzymes (biological molecule capable of catalyzing chemical reactions, typically proteins or nucleic acids). Exemplary catalysts in the sense of the disclosure include multicomponent catalysts (catalysts which contain mixtures of various chemical constituents rather than one single chemical element or one single chemical compound) and in particular multicomponent metal catalysts including at least two components, which in combination confers catalytic activity to the multicomponent catalyst, such as the MoVNbTeOx catalyst for converting propane plus $NH_3$ and $O_2$ selectively into acrylonitrile [4] or the BiMoOx based multicomponent catalyst for converting propane plus $NH_3$ and $O_2$ selectively into acrylonitrile [5] or the Copper/Zinc-Oxide heterogeneous catalysts for $CO_2$ reaction reduction [6], and additional catalysts of one or more chemical reactions identifiable by a skilled person.

The term "chemical reaction" in the sense of the disclosure indicates a process that leads to the chemical transformation of one set of chemical substances to another. Typically, chemical reactions encompass changes that only involve the positions of electrons in the forming and breaking of chemical bonds between atoms, with no change to the nuclei (no change to the elements present) and can often be described by a chemical equation. Chemical reactions in the sense of the disclosure comprise the transformation of gaseous nitrogen and hydrogen into ammonia, and similar industrially important processes such as partial oxidation of alkenes to epoxides, hydrocarbon partial hydrogenation, carbon monoxide and dioxide reduction, hydrogen or methanol fuel cells, conversion of butane to maleic anhydride and additional chemical reactions identifiable by a skilled person (see e.g. [7])

In screening methods herein described, one or more catalysts are selected with desired target properties and enhanced activity with respect a reference catalyst for a target chemical reaction, to improve the performance of the reference catalyst which is typically defined in terms of rates, selectivity, stability, and/or lifetime of the catalyst Target properties according to the present disclosure are activity, selectivity, stability of a catalyst of a chemical reaction which affects the chemical reaction rate as will be understood by a skilled person.

As used herein, the word "activity" indicates a tendency of a chemical reaction to occur. In particular with reference to a catalyst the term activity indicates a capacity of the catalyst to change and in particular accelerate a chemical reaction. Activity of a catalyst can be measured in terms of reaction rate or Turn-Over-Frequency (TOF) of a reaction catalyzed by the catalyst. An enhanced or improved activity of a catalyst as described herein refers to a catalyst that is capable of increasing the rate of a chemical reaction over a reference catalyst when measure under equivalent reaction conditions.

The term "reaction condition" refers to a set of environmental parameters under which a chemical reaction is performed. Exemplary reaction conditions or set of environmental parameters comprise any one parameter of temperature, pressure, partial pressure of each reactant, voltage, solvent, flow rate, and time of reaction alone or in combination as well as others environmental parameters or reaction conditions identifiable to a person skilled in the art.

As used herein the word "selectivity" indicates an inclination of a chemical reaction to occur in one pathway over another pathway. In particular with reference to a catalyst the term selectivity indicates a degree of inclination for a catalyst to accelerate a chemical reaction in one chemical reaction pathway to produce one chemical product over another chemical reaction pathway to produce another chemical product. Selectivity is measured in terms of ratio between competing reaction rates of one chemical reaction pathway over another chemical reaction pathway leading to one chemical product or another chemical product which are different from each other. An exemplary selective reaction is the Vanadium Pyrophosphate (VPO) catalyst of butane plus oxygen to form maleic anhydride which can be over 70% selective even though 16 steps are involved. Another is the BiMoOx based multicomponent catalyst mentioned above in which 7 dopants were developed over 30 years of development to change 55% selectivity to 80%. An Exemplary chemical reaction presenting selectivity issue, is the reaction of hydrogen and carbon monoxide which yields methane when nickel is used as catalyst and the same reactants yield methanol when copper is used as catalyst. In such case, nickel is selective for the former reaction over the latter reaction, while copper is selective for the latter reaction over the former reaction. Additional examples will be identifiable by a skilled person.

In general, the word "stability" indicates a physical and/or chemical state of a chemical compound or material remaining physically and chemically substantially unchanged. Thus, the term "stability" when used in connection with the screening methods of the present disclosure indicates the physical and/or chemical state of the compound or material over a time scale and/or under a target reaction condition of a chemical reaction.

In particular with reference to a catalyst, the term stability indicates the physical and chemical unchangeability of the catalyst over the time scale and/or under target reaction conditions of a chemical reaction catalyzed by the catalyst. Accordingly, stable catalyst in the sense of the disclosure comprise kinetically stable catalysts which are thermodynamically stable and kinetically stable catalysts which are thermodynamically unstable under the reaction conditions as will be understood by a skilled person. Physical and/or chemical changes of a catalyst detected to identify the related stability comprise catalyst segregation (enrichment of atoms, ions or molecules at a microscopic region of a catalyst), catalyst degradation (breakage of one or more chemical bonds resulting in the change of chemical structure and properties of a catalyst), Physical and/or chemical changes of a catalyst detected to identify the related stability also comprise changes in the location of dopants in layer of a multilayer catalysts as well loss of material (e.g. vaporization as a gas) or degradation (e.g. by oxidation) of the catalysts and additional changes identifiable by a skilled person.

Exemplary stable catalysts include the VPO butane to maleic anhydride and BiMoOx multicomponent ammoxidation catalysts mentioned above that are run for many 1000's of hours with only occasional insertion of active elements to replace material lost by evaporation or decomposition. and additional catalysts identifiable by a skilled person. (see e.g. [8])

Stability of a catalyst in the sense of the disclosure can be measured as a free energy difference between the proposed configuration and/or composition and a set of possible alternative configurations of the catalyst under target reaction conditions of a chemical reaction.

In particular, in preferred embodiments herein described wherein the catalyst is a multicomponent multilayer catalyst including dopants, the stability of the catalyst can be measured as a free energy difference between a set of possible configurations of the dopants in one or more layer of the catalyst to identify the dopant's predominant location among the one or more layers which defines the affinity of the of the dopant for that layer. Accordingly, a dopant will be relatively distributed in the layers according to the standard free energy of the catalyst including the dopants, and have more affinity and therefore be predominantly located in one of the layer over the remaining layers, in the thermodynamically stable configuration of the doped composition. Predominant and predominantly as used herein in connection with location indicate the portion of a catalyst where more than 50% of a component and in particular a dopant is located.

In some preferred embodiments of the screening methods herein described, the catalysts have up to 50 atoms up to 100 atoms or up to 200 atoms or up to 300 atoms, Examples of catalyst with such size comprise catalysts for the $NH_3$ synthesis and VPO catalyst as well as additional catalysts identified by a skilled person.

In other preferred embodiments of the screening methods herein described, the catalysts have 100,000 atoms, up to 150,000 atoms, up to 200,000, up to 400,000 up to 500,000 or up to 1 million or more. Examples of catalyst with such size are the BiMoOx ammoxidation catalyst [5] and the $M_2$ component of the MoVNbTeOx ammoxidation catalyst [4] as well as additional catalysts identifiable by a skilled person.

Accordingly, in preferred embodiments of the screening methods herein described, the screening is performed with respect to the active site of a catalyst, and in some of these embodiments (as for $NH_3$ synthesis and VPO selective oxidation) the active site can have hundreds of atoms enabling QM methods, but in other examples such as the dealloyed nanoparticles and nanowires for the hydrogen fuel cell or the copper nanoparticles for the reduction of $CO_2$ to ethanol there may be 200,000 atoms requiring the ReaxFF reactive force field [9].

In some embodiments of the screening methods herein described, the catalyst can be multicomponent catalysts including at least two components, which in combination confers catalytic activity to the multicomponent catalyst, such as multicomponent catalysts comprising a metal such as iron or a nonmetal atom.

Accordingly, exemplary multicomponent catalysts comprise a multilayer multicomponent catalyst capable of catalyzing at least a solid-gas heterogeneous chemical reaction and doped with at least one dopant atom one or more of the three outmost surface layers of the catalyst. The term "dopant" refers to an element that is not initially present but is introduced into a chemical material to alter its original chemical composition and properties such as its catalytic activity or absorption spectrum or adsorption/sensing efficiency, and additional properties identifiable by a skilled person. Dopants can be substitutional dopants if the dopant substitute an atom of the multilayer multicomponent catalyst, or can be interstitial dopant a site in the catalyst at which there is usually not an atom an iron catalyst Exemplary substitutional dopant in an Fe catalyst are Rh, Pd, Pt, Cu, Zn, Ag, Au, example interstitial dopant in an iron catalyst comprise H, C, and N.

A doped multilayer catalyst is typically formed by a predominant component forming more than 50% of the catalyst, such as a transition metal and in particular iron, and dopants forming less than 50% of the catalysts. Accordingly, in an exemplary embodiment, the predominant component of the two or more components of the multicomponent catalyst is iron and the balance of the two or more components are considered as dopants in the iron. In such exemplary embodiment, the iron can be on a Fe(111) [2] or an Fe(211) [10] plane of a Fe crystal or can be in a film.

In preferred embodiments, of the screening methods herein described the catalyst can be a heterogeneous catalyst which catalyzes reactions involving a number of distinct steps for making a desired products, such as conversion of propane into acrylonitrile, conversion of butane to maleic anhydride, or Haber Bosch reaction for the synthesis of ammonia.

In particular, in some embodiments of the screening methods herein described, the catalysts can be an inorganic catalyst containing at least one inorganic compound and typically one or more transition metal centers such as Fe, Pt, Co, Cu and others identifiable to a skilled person. Examples of inorganic catalysts comprise M1 and M2 Phases of MoVNbTeOx [11], Vanadium pentoxide ($V_2O_5$) [12], $VOPO_4$ [13], $BiMoOx$ [14], Cu/Cu oxide redox pair on copper electrode optionally including Zn as a dopant (Cu, $Cu_{10}Zn$, $Cu_4Zn$, and $Cu_2Zn$) [3], silver nanoparticles deposited on alumina substrates[15] and added with promoters such as alkali and nickel nanoparticles supported on alumina or spinels with promoters such as CaO [16].

In those embodiments, the screening methods herein described can be performed with respect to the target reaction and target reaction conditions indicated in Table 3.

TABLE 3

| Catalyst | No. of Atoms | Target Reaction | Exemplary Target Reaction Conditions |
| --- | --- | --- | --- |
| M2 Phase of MoVNbTeOx | <50 | propane into acrylonitrile | Distribution of the V and Te [11] |
| Vanadium Oxide | <50 | methanol to formaldehyde | a V2O5(001) slab at 650 K exposed to a gas of 30 methanol molecules at 2000 K for 250 Ps[12] |
| $VOPO_4$ | <50 | butane into Maleic Anhydride | Temperature 673-723 K (see [13] at p. 4603, left col. ll. 37-38) |
| $BiMoO_x$ | <50 | propene plus $NH_3$ and $O_2$ to acrylonitrile | "higher partial pressures of [ammonia and propene] [14] |
| Cu/Cu oxide redox pair on cupper electrode optionally including Zn as a dopant (Cu, $Cu_{10}Zn$, $Cu_4Zn$, and $Cu_2Zn$), | <50 | Electrochemical reduction of CO to ethanol | Oxygen in the product might arising water rather than from CO as ethanol formation competes with the formation of ethylene that also arises from *C—CH" (solvent effect and selectivity) [3] |

TABLE 3-continued

| Catalyst | No. of Atoms | Target Reaction | Exemplary Target Reaction Conditions |
| --- | --- | --- | --- |
| Silver nanoparticles deposited on alumina substrates and added with promoters such as alkali metals and traces of chlorine | <50 | Ethelene partial oxidation to ethylene oxide | 325-450° C. (See, e.g., Ref. [15]) |
| Nickel nanoparticles supported on alumina or spinels with promoters such as CaO | <50 | hydrogen and syngas production from Natural Gas Steam Reforming | temperatures above 900° C. (See, e.g., [Ref. [16]) |

In addition, the catalyst can be contained inside a porous support such as a zeolite or a metal-oxide framework In embodiments of the screening methods herein described, the above catalysts and other catalysts in the sense of the disclosure can be screened for activity alone or in combination with stability and/or selectivity, by providing candidate catalysts having a structural or compositional difference with respect to the above catalyst or other catalysts provided as a reference catalyst as will be understood to a person skilled in the art.

The wording "structural difference" in the sense of the disclosure refers to changes in the configuration or spatial arrangement of elements of the reference catalysts that result in a catalyst having the elements distributed on different lattice positions. An example of candidate catalysts having a structural difference with respect to a reference catalyst is an Fe-bcc(211)R surface with respect to a reference Fe catalyst with the Fe(111) surface. Another example is the VPO butane to maleic anhydride catalyst for which there are 6 possible crystal structures with one crystal is important for activating the butane and another crystal is important for keeping other steps selective. In a further example for the MoVNbTeOx ammoxidation catalyst there are two phases: M1 converts propane to propene while M2 converts propene to acrylonitrile.

The wording "compositional difference" in the sense of the disclosure refers to changes in the configurations of elements of the reference catalyst which result in a catalyst having a different chemical composition compared with the reference catalysts. For example, compositional difference encompasses a modification in the constitutive elements of the reference catalyst and/or a modification of the ratio among constitutive elements of the reference catalyst as will be understood by a skilled person.

In some embodiments, the structural or compositional difference of the candidate catalyst with respect to the reference catalyst can be the presence of a substitutional dopant and in particular single or multiple substitutional dopants. The dopant can be introduced through deposition, diffusion, sintering or annealing e.g. via post-depositing a dopant or precursor species containing the dopant that is successively thermally decomposed to leave. Properties of the chemical material of interest in this context are its catalytic activity, a target chemical reaction such as accelerating the rate of a chemical reaction without being consumed in the process.

In these embodiments, the presence of the dopant can affect the mechanism of the catalytic process, the rates, or the selectivity. For example, some dopants have a strong thermodynamic preference and therefore higher affinity for one of the outer three layers and that with the appropriate dopant, the rates and selectivity can be dramatically enhanced In these embodiments, the type, amount and ratios of dopants to be provided depend on the specific chemical properties of the catalyst. For example in exemplary embodiments wherein the catalysts is an iron catalyst based on iron films terminated by an Fe-bcc(111) surface, the dopant can be selected from Rh, Pd, Pt, Cu, Zn, Ag, Au, Cd, Ni, Co, Cr, and Si, or any combination thereof and can be applied through (see FIG. 7). Other exemplary embodiments comprise, Pt doped with Ni or Co or iron films terminated by an Fe-bcc(211) or other surfaces, other catalyst surfaces, such as Pt-fcc(111) for the oxygen reduction reaction, and catalyst systems, such as N-doped amorphous carbonaceous electrodes containing metal impurities. In those embodiments, In the screening methods herein described, the plurality of candidate catalysts having structural and/or compositional difference with respect to a reference catalyst of the target chemical reaction can comprise practically any element of the periodic table. Accordingly, for screening target properties of a reference catalyst a number of 20 to 50 candidates catalysts are typically considered possibly including 2 or more (the BiMoOx includes 7 dopants) to identify an optimal change under target reaction conditions.

In screening methods herein described hierarchically screening a plurality of candidate catalysts comprises hierarchically screening the plurality of candidate catalysts for activity for a target chemical reaction under a target condition In particular, in a screening method according to the present disclosure hierarchically screening for activity for a target chemical reaction the plurality of candidate is performed with respect to a rate-limiting step of the target chemical reaction under the target reaction condition.

In particular in embodiments of the screening method herein described, hierarchically screening for activity with respect to a rate-limiting step of the target chemical reaction under the target reaction condition, comprises determining a plurality of rate-limiting steps of the chemical reaction by analyzing a free-energy diagram of the reference catalyst.

The term "free energy diagram" or "free energy profile" or "free energy network" when used in connection with a chemical reaction indicates a theoretical representation of an energetic pathway along a reaction coordinate as the reactants are transformed into products as will be understood for a person skilled in the field of chemistry. In particular, a free energy diagram can comprise low-free-energy resting states and high-free-energy transition states, in which the resting states are local minima of the free energy profile while transition states are the highest-free-energy points between two resting states. In a free energy diagram according to the disclosure, the free-energy differences between each couple of transition and resting states define a set of free-energy barriers as will be understood by a skilled person.

A free energy diagram for a certain chemical reaction can be obtained from published literature or scientific articles such as[1, 2] [10] [17] [18]The free energy diagram can also be calculated using full quantum mechanics calculation, ReaxFF based reactive molecular dynamics or a combination of both illustrated in the elucidation of the Cu nanoparticle reduction of CO to ethanol, as will be understood by a person skilled in the art of computational chemistry. In particular, analyzing a free-energy diagram of the reference catalyst comprises calculating the free-energy and the free-energy barriers for a set of catalyst/environment configurations with different stoichiometry (due to the presence on the catalytic site of adsorbates/intermediates as generated by the addition/removal of species from/to environment) linked among them by reaction steps, such that a catalytic cycle is established in which the initial and final configurations coincide for the catalyst whereas the transformation of reactants into products has been achieved in the environment.

In some embodiments wherein the catalysts have hundreds of atoms the free energy reaction network can be derived using quantum mechanics (QM) calculations using density functional theory. In those embodiments the screened catalysts can have up to 50 atoms up to 100 atoms or up to 200 atoms or up to 300 atoms, and the screening can use quantum mechanics to obtain the free energy reaction network, allowing computations of free energy reaction network on the timescale of tens of picoseconds up to 100 picoseconds.

In some other embodiments wherein a catalyst contains 100,000 atoms, up to 150,000 atoms, up to 200,000, up to 400,000 up to 500,000 or up to 1 million or more (such as a nanoparticle (NP) or other catalyst s containing hundreds, thousands of atoms) such as 100,000 atoms, up to 150,000 atoms, up to 200,000, up to 400,000 up to 500,000 or up to 1 million or more, the screening can be performed using reactive force fields, such as ReaxFF [9], which allow computations of catalyst with millions of atoms for nanoseconds. In particular the free energy reaction network can be derived using a reactive force field method (such as ReaxFF) which is trained using QM to have nearly the accuracy of QM. A person skilled in the art will understand that in ReaxFF the interatomic potential describes reactive events through a bond-order formalism, where bond order is empirically calculated from interatomic distances. Electronic interactions driving chemical bonding are treated implicitly, allowing the method to simulate reaction chemistry without explicit quantum mechanism consideration. Detailed information on how to perform ReaxFF on large system can be found in published literatures such as Senftle et al. [9]

For example, in some embodiments herein described, where the chemical reaction is ammonia synthesis process over Fe(111), a free-energy reaction network can be derived as described in [2], in which density-functional theory (DFT) predictions [19] [20] [21] [22] free energies and free energies and reaction rates used the (2×2) unit cell of Fe(111) (PBE-D3) [19] [20] exchange correlation functional (Example 2). The computational details can be found in [2] and its supporting information incorporated herein by reference in its entirety.

In another embodiment herein described, the chemical reaction is CO reduction on Cu(100) (FIG. 18), a free-energy reaction network can be derived according to the methods described in Cheng et al. [23], wherein the effects of the solvent were included explicitly to obtain free energy barriers accurate to 0.05 eV. Such full explicit solvent calculations had not been reported previously because the full solvent requires ~1 nanosecond to equilibrate but QM based MD (AIMD) is practical only for ~40 picoseconds. Using ReaxFF reactive molecular dynamics (RMD) simulations enabled equilibration of the solvent so only 10 ps was needed for the AIMD simulations. Free energy barriers for various reaction steps and free-energy differences are obtained by using metadynamics and thermodynamic integration for various reaction steps. The computational details of using metadynamics and thermodynamic integration can be found in references [24] [25] [26] as will be understood by a person skilled in the art.

In particular, analyzing a free-energy diagram of the reference catalyst can be performed by identifying the shortest sequence of reaction between the reactant and the product within the given free energy diagram and then sectioning the path into a sequence of resting states and transition states. The set of energy barriers defined by the free-energy difference between each couple of transition and resting states is then arranged in a descending order. The shortest reaction path can be identified via the Dijkstra's algorithm[27] as will be understood by a person skilled in the art.

An exemplary embodiment wherein the chemical reaction is Haber-Bosch ammonia synthesis and the reference catalyst is an iron catalyst and in particular a Fe(111) is shown in Example 1.

In screening methods herein described, a free-energy diagram for a chemical reaction of a reference catalyst is analyzed to determine a plurality of rate-limiting steps of the chemical reaction.

A "rate limiting step" or a "rate determining step" ("RDS") are the reaction steps of a chemical reaction that determine the overall rate of the chemical reaction as will be understood by a person skilled in the field of chemistry. An RDS characterizes a chemical reaction step or a group of chemically rated reaction steps between each couple of transition and resting states along the free energy diagram. Each RDS is associated with an energy barrier value characterizing the free energy barrier separating two states.

In some embodiments, determining the plurality of rate-limiting steps can be performed by identifying a plurality of reaction steps in the free energy diagram and then portioning them into the plurality of rate-limiting steps. The determining step can further comprise identifying a minimum number of chemical reaction processes or a minimum-barrier path connecting the reactant and the product, sectioning the path into a sequence of resting states and transition states, and then identifying a set of energy barrier values between each couple of transition and resting states. The shortest or minimum-energy reaction path can be identified via the Dijkstra's algorithm[27] as will be understood by a person skilled in the art.

In some embodiments herein described, determining a plurality of rate-limiting steps of the chemical reaction can be performed by identifying all the potentially rate determining steps in the free energy network and then portioning them into distinct processes. This can be carried out by identifying the minimum number of processes of the chemical reaction and the corresponding reaction free energy values using full kinetic Monte Carlo ("kMC") kinetic analysis.

In embodiments herein described, a screening method further comprises defining a plurality of criteria according to the ranked rate-limiting steps to estimate a change on the energy barrier value of each rate-limiting step caused by the structural difference of each candidate catalyst with respect to the reference catalyst.

Exemplary screening criteria for an embodiment wherein the chemical reaction is Haber-Bosch ammonia synthesis and the reference catalyst is Fe(111) are illustrated in Example 2.

In some embodiments, defining a plurality of criteria according to the ranked rate-limiting steps is performed by associating a reaction connecting an initial state to a final state to each energy barrier and estimating the change in the energy barrier. The change in the energy barrier can be estimated using an electronic reaction energy corresponding to the reaction. Alternatively, the change in the energy barrier can be performed by an explicit calculation of the reaction energy barrier for the given reaction step on the candidate catalyst. The chosen initial and final state can correspond to the initial and final state of the given reaction step or can be selected on the basis of their likelihood that the selected energy difference correlate with the reaction barrier that is targeted to estimate.

In particular, estimating the change in free-energy barrier can be performed by calculating the electronic energy difference ($\Delta E$) between the initial state and the final state of the reaction associated to each barrier.

In the exemplary embodiment of the Haber-Bosch synthesis, four criteria are defined, each criterion according to one of the rate-determining steps ranked in a descending order according to its energy barrier value (see e.g. Example 10).

For example, to define the first criterion, the chemical reaction of triple bonded $N_2$ absorption over 2N state, characterized as "2N_NH2_H[zig-zag]->2N[zig-zag]+NH3", is associated with the corresponding RDS and its energy barrier. The change on the energy barrier value of the first RDS caused by the structural difference of each candidate catalyst with respect to the reference catalysts, such as a substitutional dopant, can then be estimated by calculating the electronic energy difference ($\Delta E$) between the initial state "2N_NH2_H[zig-zag]" and the final state of "2N[zig-zag]+NH3".

Accordingly, screening methods of the present disclosure further comprises for each candidate catalyst, evaluating each criterion of the plurality of criteria sequentially in the descending order to provide selected candidate catalysts, wherein the candidate catalysts having a negative change on the energy barrier value of a rate-limiting step in a criterion are evaluated in a next criterion.

In some embodiment, evaluating each criterion further comprises by calculating the energy barrier value of each RDS for each candidate catalyst and then comparing the energy barrier value of the candidate catalyst to the corresponding value of the reference catalyst.

If the candidate catalyst leads to a negative change on the energy barrier value of the RDS in a criterion, i.e. a lower energy barrier value with respect to that of the reference catalyst, this candidate catalyst will be selected for evaluation in the next criterion. If the candidate catalyst leads to a positive change on the energy barrier value, and in particular t a higher energy barrier value with respect to that of the reference catalyst, this candidate catalyst will be eliminated.

In some embodiments, evaluating each criterion further comprises calculating the energy barrier value of each rate-limiting step for each candidate and then comparing the energy barrier value of the candidate catalyst to the corresponding value of the reference catalyst.

For example, in the exemplary embodiment of Haber-Bosch ammonia synthesis wherein Fe is the reference catalyst and 34 dopants are the candidate catalysts, of the 34 dopants, 12 led to a barrier low than the 1.68 eV for Fe in the first criterion. The other dopants were eliminated from further evaluation (Example 11). In the second criterion, 6 more candidate catalysts are eliminated. The 6 remaining candidates all have lower energy barrier than Fe in the third and fourth criterion evaluation.

The method also comprises constructing a free-energy diagram for each tested candidate catalyst and performing a time evolution simulation method such as explicit kMC or microkinetic modeling for each of tested candidate catalysts to obtain a reaction rate of each tested candidate catalyst. The reaction rate can be calculated as a turnover frequency (TOF). A person skilled in the art would understand that a catalyst's turnover frequency or turnover number per time unit characterizes its level of activity. In particular, a TOF is the total number of moles transformed into a desired product by one mole of active site per hour. The larger the TOF, the more active the catalyst.

In particular, the time evolution simulation methods used herein refer to full reaction kinetics methods based on quantum mechanics free energy rate constants. Different from thermodynamics which focuses on the direction in which a chemical reaction occurs, the reaction kinetics methods are concerned with the rates of chemical reactions. The full reaction kinetics methods comprise explicit kinetic Monte Carlo or microkinetic modeling.

As a person skilled in the art would understand, kinetic Monte Carlo refers to a type of Monte Carlo computational method for simulating the time evolution of chemical reaction processes. In particular, the kMC generates a sequence of configurations and times when the transitions between these configurations occur. Exemplary software suitable for performing kinetic Monte Carlo calculations include SPPARKS (spparks.sandia.gov/)[28], kmos (mhoffman.github.io/kmos/)[29], and other software identifiable to a person of ordinary skill in the related art. (see e.g. Ref [30])

As a person skilled in the art would understand, microkinetic modeling is a technique used to extend both experimental and theoretical observations to predict the results of complex chemical reaction under various conditions. In microkinetic modeling, a set of elementary reactions that are thought to be relevant for an overall chemical transformation are specified. For each reaction, a rate constant is required for both the forward and reverse direction. These rate constants can be determined using density functional theory under transition state theory. Once the rate constants are known, a master equation for the entire reaction network can be written down. The master equation expresses the rate of change of each species in the model as a function of the instantaneous concentration of all species in the model, represented as a system of ordinary non-linear differential equations. Detailed information about how to perform microkinetic modeling can be found for example in Hermes et al [31].

In embodiments of screening methods herein described, the methods to hierarchically screening for activity a plurality of candidate catalysts further comprise selecting the tested candidate catalysts having a reaction rate higher than that of the reference catalyst as reactive catalysts.

FIG. 1 provides a control-flow diagram that represents one implementation of the first-principles hierarchical high-throughput screening method herein described for active catalysts and its application for optimizing a reference catalyst for a higher reaction rate.

First, for a given chemical reaction of interest catalyzed by a reference catalyst, a plurality of candidate catalysts is provided (100). Then, a plurality of rate-limiting steps of the chemical reaction are determined by analyzing a free-energy diagram of the reference catalyst (101). The rate-limiting steps are then ranked according to their energy barrier values in a descending order to provide ranked rate-limiting steps of the first chemical reaction (102). A plurality of criteria according to the ranked rate-limiting steps are then defined to estimate a change on the energy barrier value of each rate-limiting step caused by the structural difference of each candidate catalyst with respect to the reference catalyst of the first chemical reaction (103). For each candidate catalyst, each criterion of the plurality of criteria is evaluated sequentially in the descending order to provide selected candidate catalysts, wherein candidate catalysts having a negative change on the energy barrier value of a rate-limiting step in a criterion are evaluated in a next criterion (104). Candidates having a positive change on the energy barrier value of a rate-limiting step in a criterion are eliminated. For the selected candidate catalysts, a free-energy diagram of the chemical reaction is constructed, and a reaction rate is obtained (105). The active catalysts further selected are rate-selected active catalysts having a reaction rate higher than the reaction rate of the reference catalyst (106).

Accordingly, as exemplified in FIG. 1, hierarchically screening for activity the plurality of candidate catalysts with respect to the reference catalyst, is performed to provide a rate-selected active catalyst having a reaction rate under the target reaction condition higher than the reaction rate of the reference catalyst for the same target chemical reaction under the same target condition, as will be understood by a skilled person upon reading of the present disclosure.

In some embodiments of the screening methods herein described, activity of the plurality of candidate catalysts can be screened in combination with the catalyst stability and/or selectivity.

Accordingly, screening methods of the disclosure can further comprise an additional screening of the candidate catalysts and/or rate-selected active catalysts for stability and/or selectivity for the target reaction, in addition to hierarchically screening the plurality of candidate catalysts for activity performed, to select rate-selected active catalysts with retained or increased stability and/or increased selectivity with respect to the stability and selectivity of the reference catalyst.

In screening methods of the disclosure, the additional screening of the candidate catalysts and/or rate-selected active catalysts for stability and/or selectivity for the target reaction can be performed at various steps of the screening method as will be understood by a skilled person. Preferably, screening of the target properties within screening methods of the disclose is performed hierarchically starting from the target property among activity selectivity and stability which is more computationally costly In some embodiments of screening methods herein described, the computer-based method is directed to screening for activity and stability of the plurality of candidate catalysts.

In particular, the screening method herein described can be used for screening a plurality of candidate catalysts of a chemical reaction catalyzed by a reference catalyst for stable active catalysts having a reaction rate with respect to the chemical reaction higher than a reaction rate of the reference catalyst with respect to the same chemical reaction and having a same or increased stability with respect to the stability of the reference catalyst under the same reaction conditions.

The method comprises hierarchically screening the plurality of candidate catalysts for activity for the target chemical reaction under the target condition, by performing a computer-based method to screen for activity of the present disclosure, further comprising testing on a computer, stability of the candidate catalysts, to select candidate catalysts having a stable configuration before the evaluating;

testing on a computer, stability of the rate selected candidate catalysts, to select rate selected candidate catalysts having a stable configuration before the constructing and/or the selecting; and/or testing on a computer, stability of the rate-selected active catalyst, to further select rate selected active catalyst having a stable configuration, to provide rate-selected active catalyst stable for the chemical reaction under the target condition.

Accordingly, the method of screening a plurality of candidate catalysts for active stable catalysts can further be described based on the illustration of FIG. 1, which schematically shows an embodiment of the method of screening for activity of the disclosure which in embodiments directed to additionally screen the plurality of candidate catalysts further comprises performing a stability test to eliminate unstable catalysts in connection with one or more of the steps of the method.

In particular, in those embodiments, the stability test can be performed prior to the active catalysts are selected, such as prior to step 101, after step 101 but prior to step 102, after step 102 but prior to step 103, after step 103 but prior to step 104, after step 104 and prior to step 105; or after step 105 and prior to step 106 in FIG. 1. The stability test can also be performed after the rate-selected active catalysts are selected (after 106 in FIG. 1).

In those embodiments, the stability testing is performed to ensure that the structural and/or compositional difference introduced in the candidate catalysts with respect to the reference catalyst does not introduce insurgence of degradation or segregation mechanisms. For example, the selected active catalysts need to have the structural difference at a specific location of the catalyst such as on a surface or subsurface in order to be stable.

The stability test can be performed by evaluating the energy difference between a proposed configuration for a candidate catalyst and other possible alternative configurations of the same candidate catalyst.

In some embodiments, the stability test comprises for each catalyst identifying a set of catalyst configurations having the structural difference at a different position with respect to one another; computing an electronic energy of each catalyst configuration; and selecting the catalyst having a catalyst configuration with a lowest electronic energy.

The electronic energy of a given configuration can be computed by various ab initio quantum mechanics methods, density-functional theory (DFT) simulations, Quantum Monte Carlo, Møller-Plesset perturbation theory, Configuration interaction, Coupled cluster, Multi-configurational self-consistent field, Hartree-Fock method, tight binding model, perturbation theory and other methods identifiable to a person skilled in the art. Exemplary software suitable for performing atomic scale electronic energy calculations include VASP, and other software identifiable to a person of ordinary skill in the related art. Detailed information on various methods of performing electronic energy calculations can be found in published literatures and textbooks [32] as will be understood by a person skilled in the art.

The stable active catalysts are selected as the active catalysts having a catalyst configuration with a lowest electronic energy among the identified configurations, thus eliminating the possible segregation and degradation configurations.

For example, in embodiments wherein the catalyst candidates comprise one or more substitutional dopants, the stability test can be performed by evaluating the electronic energy of the catalyst in each configuration wherein the substitutional dopant is positioned at a different location such as the Si on the top surface, subsurface, the third layer on Fe-bcc(111) catalyst system or diffused from Fe(111) (undoped) and selecting the catalyst in a catalyst configuration with a lowest electronic energy (Example 14).

In some embodiments, performing the stability testing involves comparing the free energy for the dopant on various layers including both electronic energy and the phonon contributions to provide a total free energy difference.

The various free energy barriers are compared to the free energy barrier of the chemical reaction with the reference catalyst, also referred to as the reference free energy barrier. If the total energy barrier is lower than the reference free energy barrier, then the catalyst configuration is selected as the active catalyst. If the total energy barrier is greater than the reference free energy barrier, then the catalyst configuration is unstable and thus eliminated.

In some embodiments some dopants have a strong thermodynamic preference and therefore higher affinity for one of the outer layers of the catalyst.

Accordingly, in those embodiments, the screening method can be performed to include stability testing directed to select a catalyst having one or more dopant atoms predominantly located in one or more specific layer of the three outer layers of a multicomponent multilayer catalyst.

In particular in those embodiments, candidate catalysts are screened to select the configurations based on the thermodynamic preference of the dopant and related affinity for a particular outer layer of the multicomponent catalysts (outmost first layer, second, or third).

Accordingly, in embodiments herein described where the catalyst is a multicomponent multilayer catalyst the stability testing is preferably performed to select the configuration having one or more dopant atoms predominantly located in one or more specific layer of the three outer layers of the catalyst. In those embodiments, the stability testing can be performed alone or in combination with additional stability testing to provide a total free energy difference.

The stability testing can be performed before or after any one of the other steps of the screening method herein described to select the catalyst configuration that increases the rate and/or selectivity of the catalyst as will be understood by a skilled person upon reading of the instant disclosure.

In an exemplary embodiment provided by an iron multicomponent multilayer catalyst multiple, the screening identified Rh, Pd, Pt, Cu, Zn, Ag, Au, Cd as dopant having the highest affinity for the outmost first layer, and Ni, Co, Cr, and Si as dopant having a highest affinity for the second layer, and Ga as a dopant having the highest affinity for the third layer and at their preferred layer these dopants can accelerate the reactions. (see FIG. 7). Other examples: for the oxygen reduction reaction comprising doping for Pt with Ni or Co which also can increase the rate as will be understood by a skilled person.

In some embodiments herein described, methods are described for screening a plurality of candidate catalysts for active and selective catalysts having a higher selectivity for a target chemical reaction than for at least a second chemical reaction.

In some embodiments, the target chemical reaction and the at least second chemical reaction evolve from same reactants but produce different products. In some embodiments, the target chemical reaction and the at least second chemical reaction involve different reactants and different products.

In those embodiments, the screening method comprises
- providing a plurality of rate-selected active catalysts for the chemical reaction under the target condition by hierarchically screening a plurality of candidate catalysts for activity for the target chemical reaction with a computer-based method herein described, each rate-selected active catalyst having a target reaction rate;
- for each rate-selected active catalyst, constructing, on a computer, a free-energy diagram of a second chemical reaction different from the target chemical reaction and performing a time evolution simulation method on a computer to obtain a second reaction rate of each rate-selected active catalyst;
- obtaining a selectivity ratio between the target reaction rate and the second reaction rate of each rate-selected active catalyst; and
- selecting the rate-selected active catalyst having a selectivity ratio greater than 1 to provide a rate-selected active catalyst selective for the chemical reaction under the reaction condition.

Figure 2:
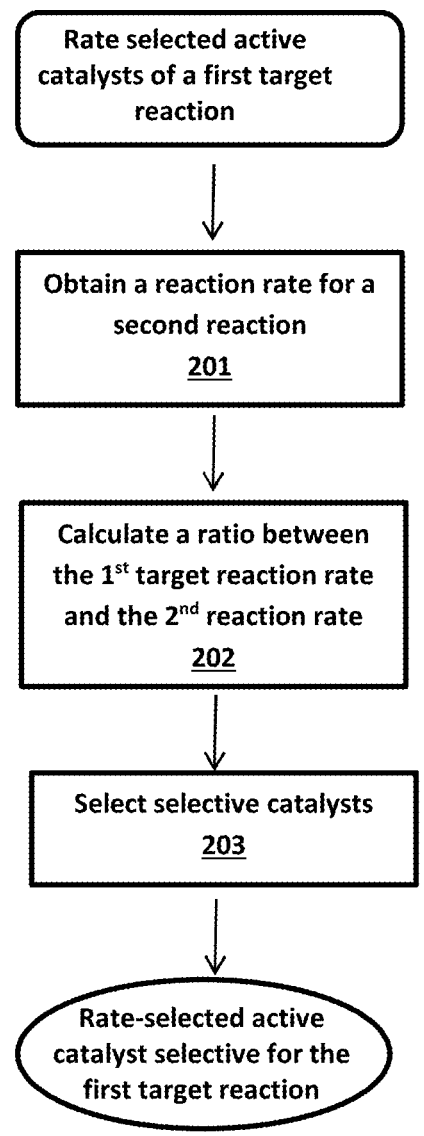
FIG. 2 provides a control-flow diagram that represents one implementation of the first-principles hierarchical high-throughput screening method herein described for selective catalysts and its application for optimizing a reference catalyst for a higher selectivity for a given chemical reaction.

Reference is made in this connection to the schematics of FIG. 2 provides a control-flow diagram representing one implementation of the first-principles hierarchical high-throughput screening method herein described for selective catalysts and its application for optimizing a reference catalyst for a higher selectivity for a first chemical reaction than for at least a second chemical reaction.

The methods herein described comprise selecting a set of active catalysts having a reaction rate higher than the reaction rate of the reference catalyst according to FIG. 1 (200).

For each active catalyst, a free-energy diagram of at least the second chemical reaction is constructed and a second reaction rate of each active catalyst is obtained (201). Then, a ratio between the first reaction rate of each active catalyst and the second reaction rate of each active catalyst is obtained (202). The selective catalysts are selected as the active catalyst having a ratio greater than 1 (203).

Constructing the free-energy diagram of the at least the second chemical reaction and calculating the second reaction rate as illustrated in step 201 of FIG. 2 can be performed using the same methods for step 105 of FIG. 1 as described above.

The ratio between the target reaction rate of each reactive catalyst and the second reaction rate of each reactive catalyst can be obtained by dividing the first reaction rate by the second reaction rate.

In some embodiments, the ratio is in a range from 2 to 100,000. The selective catalysts are selected as having a ratio greater than 2, 5, 10, 100, 1000, or 10000. In some embodiments, the ratio of the selective catalyst is higher than the ratio of the reference catalyst.

Different reaction conditions can also be adjusted and tested for catalysts selective under that specific reaction conditions as will be understood by a person skilled in the art.

Figure 18:
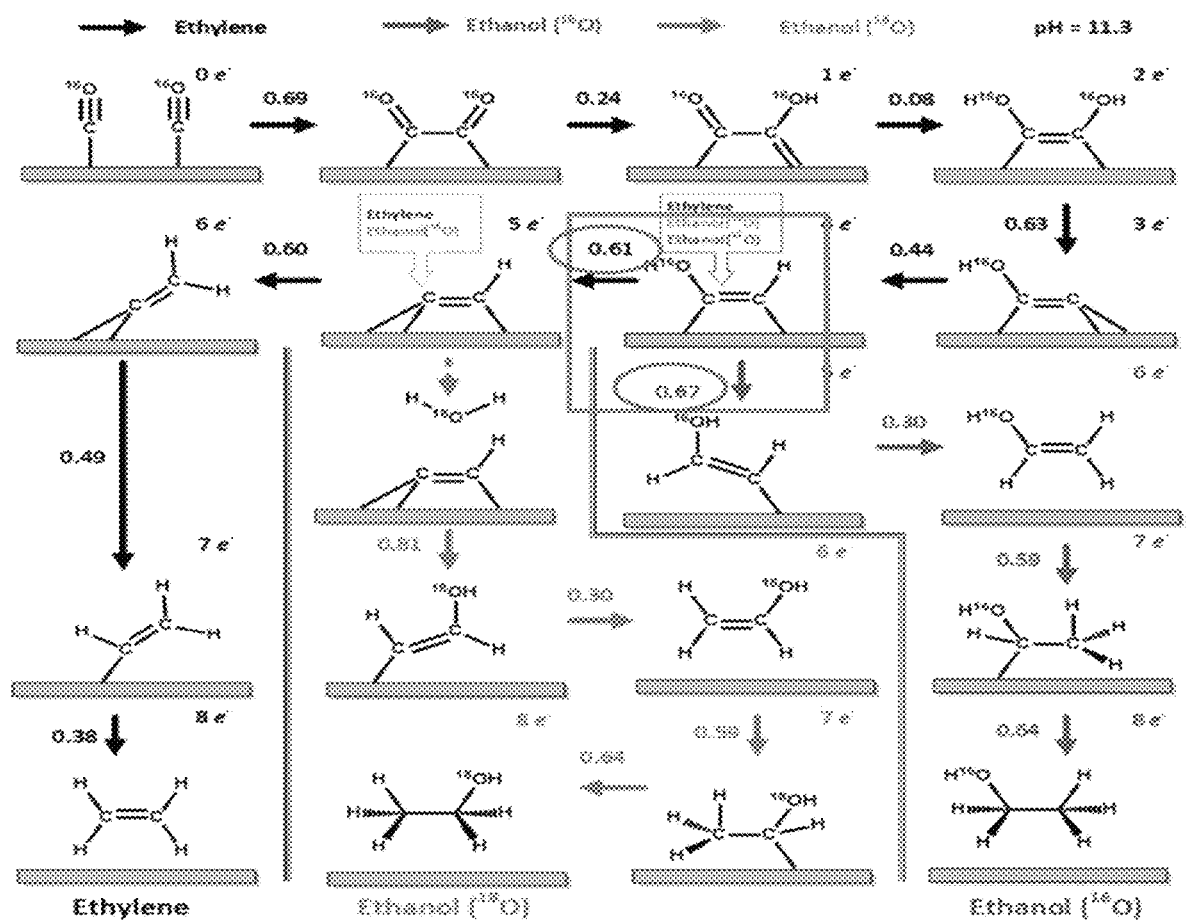
FIG. 18 illustrates in an exemplary reaction mechanism for forming ethylene and ethanol from CO reduction on Cu(100) surface described in [3].

In an exemplary embodiment of electrocatalytic reduction of CO to produce organic products, the method of screening for selective catalyst herein described can be used to screen catalysts having a higher selectivity for the product of ethylene than for other products such as methane or ethanol. The reaction mechanism for forming ethylene and ethanol from CO reduction on Cu(100) surface is illustrated in FIG. 18.

It has been shown that at an overpotential of −0.6 V RHE the two main products from this reaction are ethylene (H2C=CH2) and ethanol (CH3-CH2OH) each of which takes 10 steps, but for which the first 6 are in common. The branching point occurs at the HC=COH intermediate (indicated by the square). Since the activation energy from the common intermediate to ethylene is $\Delta G^\ddagger=0.61$ eV while for formation if ethanol it is $\Delta G^\ddagger=0.067$ the relative barrier is $\delta\Delta G^\ddagger=0.06$ eV which leads a production ratio at 298K of 11:1 ethylene:ethanol. The ratio observed experimentally shows that $\delta\Delta G^\ddagger=0.066$ eV [3] is in excellent agreement with the theory. (Cheng et.al. Full atomistic reaction mechanism with kinetics for CO reduction on Cu(100) from ab initio molecular dynamics free-energy calculations at 298 K [23].

In order to select catalysts more selective for the production of one product over another (ethylene over ethanol), a set of active catalysts having a reaction rate with respect to the reduction of CO to ethylene higher than the reaction rate of the reference catalyst Cu(100) can be selected according to the method illustrated in FIG. 1. Then for each active catalyst, the second free energy profile of the reduction of CO to ethanol can be calculated according to step 201 of FIG. 2. Catalysts selective for ethylene over ethanol are then selected based on the ratio of the first reaction rate and the second reaction rate according to step 203 of FIG. 2. In particular, the ideal selective catalysts will have a ratio greater than the ratio of Cu(100), i.e. greater than 11.

A person skilled in the art will understand that to screen for selective catalysts, the catalysts are selected to lower the free energy barrier of the chemical reaction of interest, i.e. the one leading to the desired product, while increasing the free energy barrier of the other chemical reaction, i.e. the ones leadings to the undesired products.

In some embodiments the screening methods herein described comprise screening the plurality of candidate catalysts for activity, stability and selectivity for the target chemical reaction under the target condition. In particular, the screening method herein described can be used for screening a plurality of candidate catalysts for active, stable and selective catalysts having a higher selectivity for a target chemical reaction than for at least a second chemical reaction as well as having a same or increased stability with respect to the stability of the reference catalyst under the same reaction conditions.

In those embodiments, the method comprises providing a rate-selected active catalyst selective for the target chemical reaction under the target condition by a computer-based method for hierarchically screening activity and selectivity for a target chemical reaction under a target reaction condition herein described such as the one schematically described in FIG. 2, In those embodiments, the method further comprising performing a stability test to eliminate unstable catalysts in connection with one or more of the steps of the method.

For example in the method to screen activity and selectivity of candidate catalyst according to the schematics of FIG. 2, the stability test can be performed prior to the selective catalysts are selected, such as prior to step 201, after step 201 and prior to step 202, after step 202 and prior to step 203 of FIG. 2. The stability test can also be performed prior to, during or after the set of active catalysts of a first reaction is selected (step 200 of FIG. 2). In particular, the stability test can be performed prior to step 101, after step 101 but prior to step 102, after step 102 but prior to step 103, after step 103 but prior to step 104, after step 104 and prior to step 105; or after step 105 and prior to step 106 in FIG.

1). The stability test can also be performed after the selective catalysts are selected, such as after step 203 of FIG. 2.

In some embodiments, the screening methods herein described further comprise providing a plurality of candidate catalysts by modifying the reference catalyst. In particular, modifying the reference catalyst can be performed by introducing a structural and/or compositional difference in the candidate catalysts with respect to the reference catalyst. In some of these embodiments, modifying the reference catalyst is carried out by replacing one or more atoms in the reference catalyst with one or more same or different substitutional elements. In some of these embodiments, modifying the reference catalyst can be carried out by adding an additional element to the reference catalyst, eliminating an element from the reference catalysts, and/or rearranging the elements already in the reference catalysts.

In the embodiments herein described, compared to other existing methods [33] [34] which typically assume linear scaling in the reaction rates to focus on a specific RDS or to reconstruct the energy diagram on given catalysts, the hierarchical high-throughput screening methods herein described consider a number of potential RDS and a diversity of energetic and barrier calculations by arranging all the potentially rate-determining steps of a complex reaction mechanism in hierarchical order and then sequentially filter candidate catalysts that accelerate the overall reaction rate also when the largest barrier corresponding to the previous RDS is no longer rate determining. This approach thus achieves quantitative accuracy and more rigorous and wider applicability in many industrially-relevant catalytic processes.

Accordingly, screening methods herein described allow, in several embodiments, to identify catalysts with reaction rates 3~50 times increased compared to an existing catalyst while either retaining or improving the stability and the selectivity.

The screening methods herein described are computer implemented methods as will be understood by a skilled person.

Figure 3:
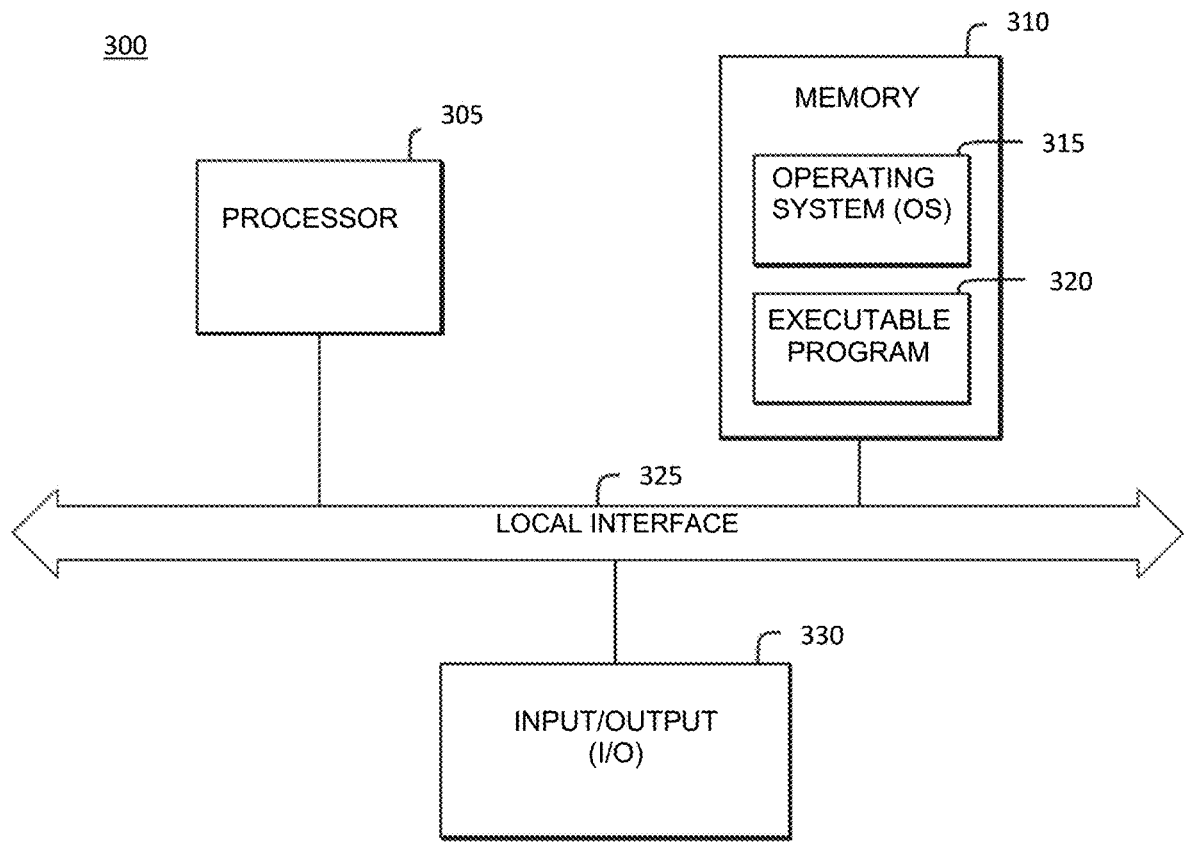
FIG. 3 illustrates an embodiment of hardware implementation for the screening methods herein described.

FIG. 3 illustrates an embodiment of hardware implementation for the present screening methods.

Software realizations of the currently disclosed first-principles hierarchical high-throughput screening methods can be developed to enable design and optimization of catalysts FIG. 3 is an exemplary embodiment of a target hardware (300) (e.g., a computer system) for implementing the embodiments of the present disclosure, including the embodiment shown in FIGS. 1-2. This target hardware comprises a processor (305), a memory bank (310), a local interface bus (325) and one or more Input/Output devices (330). The processor can execute one or more instructions related to the implementation of FIGS. 1-2 et al., and as provided by the Operating System (315) based on some executable program (320) stored in the memory (310). These instructions are carried to the processor (305) via the local interface (325) and as dictated by some data interface protocol specific to the local interface and the processor (305). It should be noted that the local interface (325) is a symbolic representation of several elements such as controllers, buffers (caches), drivers, repeaters and receivers that are generally directed at providing address, control, and/or data connections between multiple elements of a processor based system. In some embodiments the processor (305) can be fitted with some local memory (cache) where it can store some of the instructions to be performed for some added execution speed. Execution of the instructions by the processor can require usage of some input/output device (330), such as inputting data from a file stored on a hard disk, inputting commands from a keyboard, inputting data and/or commands from a touchscreen, outputting data to a display, or outputting data to a USB flash drive. In some embodiments, the operating system (315) facilitates these tasks by being the central element to gathering the various data and instructions required for the execution of the program and provide these to the microprocessor. In some embodiments the operating system is missing, and all the tasks are under direct control of the processor (305), although the basic architecture of the target hardware device (300) will remain the same as depicted in FIG. 3. In some embodiments a plurality of processors can be used in a parallel configuration for added execution speed. In such a case, the executable program can be specifically tailored to a parallel execution. Also, in some embodiments the processor (305) can execute part of the implementation of FIGS. 1-2 and additional configurations identifiable by a skilled person, and some other part can be implemented using dedicated hardware/firmware placed at an Input/Output location accessible by the target hardware (300) via local interface (325). The target hardware (300) can include a plurality of executable programs (320), wherein each can run independently or in combination with one another.

Screening methods of the disclosure allow for accelerated catalyst design and optimization of catalysts with faster turnover frequency with retained or enhanced stability and selectivity, with a reduced time compared to existing methods as will be understood by a skilled person.

In particular, in some embodiments herein described, for catalysts up to 300 atoms the reaction time scale catalyzed by the catalysts can occur on a simulation timescale up to 100 picoseconds. In other embodiments for catalyst over 100,000 atoms and over, using the QM based reactive field method the reaction time scale catalyzed by the catalysts can occur on a simulation timescale of nanoseconds. A reaction timescale is related to the reaction rate of the chemical reaction catalyzed by the catalysts herein described. The higher the reaction rate, the shorter the timescales on which the reaction progresses.

In an exemplary embodiment, the hierarchical high-throughput screening methods herein described reduce the computational effort to 1% of the full QM calculation which enables consideration of 100 possible dopants in the time scale normally requires for just one.

In particular, the screening methods herein described allow for optimizing and testing new candidate catalysts at a significantly reduced computational cost, typically only 1% of the computational cost for commonly used quantum mechanics calculations, while still retaining the level of accuracy obtained only using first-principle ab initio quantum mechanics methods.

Accordingly, the screening methods herein described enable computational design and optimization of multicomponent catalysts at a reasonable computational cost while providing the necessary accuracy.

The term "computational cost" indicate a computational effort typically expressed in core hours, also known as CPU hours, which provide necessary value estimation needed to calculate the cost of a computational simulation.

Accordingly, embodiments of the screening methods herein described allow identification of an optimized catalyst with respect to a reference catalyst with a CPU in the range of less than 18 million hours. For example, the Ni-subsurface doping illustrated in the examples has been singled out of 35 candidates using only ~300 geometry optimizations, for a total of less than 0.25 million cpu-hours and an estimated cost at current prices of less than ~2300 US$, to be compared with about 50 geometry optimization plus phonon calculations and 17 saddle-point searches for each candidate that would be needed if using a conventional computational approach with complete modeling (over 18 million cpu-hours at the price over 90,000US $), or an estimate of about 12 man-months and 165000 US$ in infrastructure if using trial-and-error experimental high-throughput screening.

The catalysts identified with the screening methods herein described allow in several embodiments, to optimize the reaction conditions of important reaction otherwise held at extreme and expensive condition. For example, with the iron catalysts of formula one, the extreme conditions of industrial ammonia synthesis (HB) process, typically held at 773-823 K and total pressure of 150-250 atm, are optimized by reducing temperature by 100-150 K and pressures by a factor of 10. This will allow one to reduce the cost of production plant which are presently ranging between 500.00 and 2000.00 US$ per $NH_3$ ton produced annually down to 100-450 US$ per $NH_3$ ton in 2019 dollar. The optimized catalysts can also drastically reduce production times by a factor between 1 and 2 orders of magnitude.

As a consequence, the methods herein described make it practical to examine very complex catalysts such as heterogeneous multicomponent catalysts having a large plurality of candidate configurations including compositional and/or structural changes which can affect the reaction rate of a target reaction (reaction of interest) under target reaction conditions (reaction conditions of interest).

An exemplary multicomponent catalyst obtained through the screening methods of the instant disclosure is an exemplary multilayer multicomponent transition metal heterogeneous catalyst doped with at least one dopant atom on at least one of the three outer surface layers of the transition metal and capable of catalyzing at least a solid-gas heterogeneous chemical reaction.

In particular, the exemplary catalyst is a multilayer multicomponent iron catalyst capable of catalyzing formation of ammonia from hydrogen and nitrogen gas through Haber-Bosch synthesis, at an improved reaction rate than an iron catalyst identified following simulation with the screening method of the disclosure.

In particular, the multilayer multicomponent iron catalysts have been designed to have one or more additives in each of the first three layers of the multilayers selecting for stability in each layer. (Examples 15 and 16)

In particular the composition of the catalyst was selected to be controlled by the thermodynamics so that in view of their affinity for the catalyst layers, upon annealing the dopants will be predominantly located in the outer three layers of the catalyst. The catalyst will have many other layers in addition to the outer three layers, but the outer are the layers that can affect the rates and selectivity of the catalysts In particular in the exemplary multicomponent iron catalyst screened with the methods of the disclosure, Rh, Pd, Pt, Cu, Zn, Ag, Au, Cd each have a preferential affinity for the outmost atomic layer of iron. Therefore, Rh, Pd, Pt, Cu, Zn, Ag, Au, Cd when used a dopant in the exemplary iron catalyst, they will be present at at least 10 times atom percentage compared to the second layer of iron or third layer of iron. Accordingly when an iron alloy of appropriate amounts of Rh, Pd, Pt, Cu, Zn, Ag, Au, and/or Cd is annealed at sufficiently high temperature and for enough time, Rh, Pd, Pt, Cu, Zn, Ag, Au, Cd will populate the top layer of iron at at least 10 times atom percentage that of second layer of iron or third layer of iron. Similarly, Ni, Co, Cr, and Si as dopant will have the highest affinity and will be located after in the second layer, and Ga as a dopant will have the highest affinity and will be located in the third layer Detection of the atoms predominant location in the exemplary iron catalyst and in other multicomponent multilayer multicomponent catalysts can be performed with Transmission Electron Microscopy (TEM), X-ray Photoelectron Spectroscopy (XPS) or additional techniques identifiable by a skilled person In those embodiments the additives in each of the first layer, second layer and/or third layer can be present in each of in each of the first layer, second layer and/or third layer, in an amount 5 to 10 times higher than in other layers. In particular in some of these embodiments, a fraction of the additives in the first layer can be less than 50% of the additives of the first layer but present in the first the second layer 5 or 10 times more than they are in the $2^{nd}$, $3^{rd}$, and deeper layers, a fraction of the additives in the second layer can be less than 50% of the additives of the second layer but present in the second the second layer 5 or 10 times more than they are in the $1^{st}$, $3^{rd}$, and deeper layers; and/or a fraction of the additives in the third layer can be less than 50% of the additives of the second layer but present in the in the $3^{rd}$ layer 5 or 10 times more than they are in the first two layer and deeper layers In some of those embodiments one or more layers can be designed not to have additives.

In those embodiments, most preferred dopants Rh, Pt, Pd and Cu have been identified for the first layer, and four most preferred dopants Ni, Co, Cr, and Si, have been identified for the second layer.

Additional configurations of the exemplary doped iron catalyst have been identified based on the above simulation that are expected to be stable and are expected to have a reaction activity for Haber-Bosch ammonia synthesis higher than iron catalysts without dopant.

The exemplary multicomponent catalyst comprises iron doped with at least one dopant atom on at least one of two or three outmost surface layers of the catalyst, having a Formula (I)

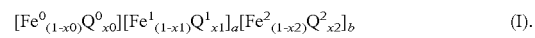

$$[Fe^0_{(1-x0)}Q^0_{x0}][Fe^1_{(1-x1)}Q^1_{x1}]_a[Fe^2_{(1-x2)}Q^2_{x2}]_b \quad (I).$$

in which $Fe^0$, $Fe^1$, and $Fe^2$ represent iron atom on an outmost first layer, iron atom on a second layer, and iron atom on a third layer of an iron crystal or iron film, respectively;

$Q^0$, $Q^1$, and $Q^2$ represent at least one dopant atom on the outmost first layer, at least one dopant atom on the second layer, and at least one dopant atom on the third layer of the iron crystal or iron film, respectively, x0, x1, and x2 represent an atom percentage of the at least one dopant on the outmost first layer, an atom percentage of the at least one dopant on the second layer, and an atom percentage of the at least one dopant on the third layer of an iron crystal or iron film, respectively, and (1-x0), (1-x1), and (1-x2) represent an atom percentage of the iron atom on the outmost first layer, an atom percentage of the iron atom on the second layer, and an atom percentage concentration of the iron atom on the third layer of an iron crystal or iron film, respectively; and a, and b respectively represent a ratio of total atoms on second layer, and a ratio of total atoms on third layer relative to a number of total atoms first layer of an iron crystal or iron film, respectively and wherein $Q^0$, $Q^1$, and $Q^2$ are independently selected from Sc, Ti, V, Cr, Mn, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ce, Eu, Er, Tm, Si, Ga or any combinations thereof;

x0, x1, and x2 each range independently from 0 to 0.5, preferably from 0 to 0.4 with the proviso that x0+x1+x2 ranges from 0.2 to 1.2, preferably from 0.2 to 0.4; and a and b independently range from 0.5 to 2.

Accordingly, in the multicomponent iron catalyst of in Formula (I), in an iron crystal or iron film, at least one dopant $Q^0$, $Q^1$, and $Q^2$ are each independently selected from Sc, Ti, V, Cr, Mn, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ce, Eu, Er, Tm, Si, Ga or any combination thereof; x0, x1, and x2 each range independently from 0 to 0.5, preferably from 0 to 0.4 with the proviso that x0+x1+x2 ranges from 0.2 to 1.2, preferably from 0.2 to 0.4 and a and b independently range from 0.5 to 2.

The term "crystal" in the sense of the disclosure indicates a material whose basic structure corresponds to a regular periodic arrangement of atoms. In an iron crystal in the sense of the disclosure, an Fe body-centered cubic (bcc) crystal structure has atoms at each of the eight corners of a cube plus one atom in the center of the cube in its unit cell and the Fe crystal is a regular periodic arrangement of this unit cell along three dimensions. Fe crystal structures and other crystal structure are detectable with X-ray diffraction and other techniques identifiable by a skilled person upon reading of the present disclosure Additional features of crystal structures in the sense of the disclosure are indicated for example in ref [35] incorporated herein by reference in its entirety and in other sources identifiable by a skilled person.

The word "film", when used in connection with catalysts in the sense of the disclosure indicates a thin film that may range from a few nm to a micrometer or larger deposited on a support. In catalyst, a film of a material can be deposited on a different material also indicated as a support. For example, gallium arsenide compounds are usually deposited by repeatedly applying a layer of gallium and then followed by depositing a layer of the arsenic. An iron film according to the present disclosure can be detected by TEM or XPS. Additional features of film structures for catalyst are indicated in Ref [36] incorporated herein by reference in its entirety and in other sources identifiable by a skilled person.

In particular, in embodiments of the multicomponent catalyst of Formula (I) according to the present disclosure $Q^0$ is the sum of the dopants Sc, Ti, V, Cr, Mn, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ce, Eu, Er, Tm, Si, and/or Ga present on the first layer of the iron crystal or iron film, the atom percentage of each dopant in the first layer is indicated herein as $q^0_{Sc}$, $q^0_{Ti}$, $q^0_V$, $q^0_{Cr}$, $q^0_{Mn}$, $q^0_{Co}$, $q^0_{Ni}$, $q^0_{Cu}$, $q^0_{Zn}$, $q^0_Y$, $q^0_{Zr}$, $q^0_{Nb}$, $q^0_{Mo}$, $q^0_{Tc}$, $q^0_{Ru}$, $q^0_{Rh}$, $q^0_{Pd}$, $q^0_{Ag}$, $q^0_{Cd}$, $q^0_{La}$, $q^0_{Hf}$, $q^0_{Ta}$, $q^0_W$, $q^0_{Re}$, $q^0_{Os}$, $q^0_{Ir}$, $q^0_{Pt}$, $q^0_{Au}$, $q^0_{Hg}$, $q^0_{Ce}$, $q^0_{Eu}$, $q^0_{Er}$, $q^0_{Tm}$, $q^0_{Si}$, and $q^0_{Ga}$ respectively, and x0 is the summation of the atom percentage $q^0_{Sc}$, $q^0_{Ti}$, $q^0_V$, $q^0_{Cr}$, $q^0_{Mn}$, $q^0_{Co}$, $q^0_{Ni}$, $q^0_{Cu}$, $q^0_{Zn}$, $q^0_Y$, $q^0_{Zr}$, $q^0_{Nb}$, $q^0_{Mo}$, $q^0_{Tc}$, $q^0_{Ru}$, $q^0_{Rh}$, $q^0_{Pd}$, $q^0_{Ag}$, $q^0_{Cd}$, $q^0_{La}$, $q^0_{Hf}$, $q^0_{Ta}$, $q^0_W$, $q^0_{Re}$, $q^0_{Os}$, $q^0_{Ir}$, $q^0_{Pt}$, $q^0_{Au}$, $q^0_{Hg}$, $q^0_{Ce}$, $q^0_{Eu}$, $q^0_{Er}$, $q^0_{Tm}$, $q^0_{Si}$, and/or $q^0_{Ga}$ present in the first layer, as will be understood by a skilled person.

Similarly, in embodiments of the multicomponent catalyst of Formula (I) according to the present disclosure $Q^1$ is the sum of the atom percentage of the dopants Sc, Ti, V, Cr, Mn, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ce, Eu, Er, Tm, Si, and/or Ga present on the second layer of the iron crystal or iron film, the atom percentage of each dopant of the second layer is indicated herein as $q^1_{Sc}$, $q^1_{Ti}$, $q^1_V$, $q^1_{Cr}$, $q^1_{Mn}$, $q^1_{Co}$, $q^1_{Ni}$, $q^1_{Cu}$, $q^1_{Zn}$, $q^1_Y$, $q^1_{Zr}$, $q^1_{Nb}$, $q^1_{Mo}$, $q^1_{Tc}$, $q^1_{Ru}$, $q^1_{Rh}$, $q^1_{Pd}$, $q^1_{Ag}$, $q^1_{Cd}$, $q^1_{La}$, $q^1_{Hf}$, $q^1_{Ta}$, $q^1_W$, $q^1_{Re}$, $q^1_{Os}$, $q^1_{Ir}$, $q^1_{Pt}$, $q^1_{Au}$, $q^1_{Hg}$, $q^1_{Ce}$, $q^1_{Eu}$, $q^1_{Er}$, $q^1_{Tm}$, $q^1_{Si}$, and/or $q^1_{Ga}$ respectively, and x1 is the summation of the atom percentage concentration of $q^1_{Sc}$, $q^1_{Ti}$, $q^1_V$, $q^1_{Cr}$, $q^1_{Mn}$, $q^1_{Co}$, $q^1_{Ni}$, $q^1_{Cu}$, $q^1_{Zn}$, $q^1_Y$, $q^1_{Zr}$, $q^1_{Nb}$, $q^1_{Mo}$, $q^1_{Tc}$, $q^1_{Ru}$, $q^1_{Rh}$, $q^1_{Pd}$, $q^1_{Ag}$, $q^1_{Cd}$, $q^1_{La}$, $q^1_{Hf}$, $q^1_{Ta}$, $q^1_W$, $q^1_{Re}$, $q^1_{Os}$, $q^1_{Ir}$, $q^1_{Pt}$, $q^1_{Au}$, $q^1_{Hg}$, $q^1_{Ce}$, $q^1_{Eu}$, $q^1_{Er}$, $q^1_{Tm}$, $q^1_{Si}$, and $q^1_{Ga}$; present in the second layer, as will be understood by a skilled person.

Further, in embodiments of the multicomponent catalyst of Formula (I) according to the present disclosure $Q^2$ is the sum of the atom percentage of the dopants Sc, Ti, V, Cr, Mn, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ce, Eu, Er, Tm, Si, and/or Ga present on the third layer of the iron crystal or iron film, the atom percentage of each dopant in the third layer is indicated herein as $q^2_{Sc}$, $q^2_{Ti}$, $q^2_V$, $q^2_{Cr}$, $q^2_{Mn}$, $q^2_{Co}$, $q^2_{Ni}$, $q^2_{Cu}$, $q^2_{Zn}$, $q^2_Y$, $q^2_{Zr}$, $q^2_{Nb}$, $q^2_{Mo}$, $q^2_{Tc}$, $q^2_{Ru}$, $q^2_{Rh}$, $q^2_{Pd}$, $q^2_{Ag}$, $q^2_{Cd}$, $q^2_{La}$, $q^2_{Hf}$, $q^2_{Ta}$, $q^2_W$, $q^2_{Re}$, $q^2_{Os}$, $q^2_{Ir}$, $q^2_{Pt}$, $q^2_{Au}$, $q^2_{Hg}$, $q^2_{Ce}$, $q^2_{Eu}$, $q^2_{Er}$, $q^2_{Tm}$, $q^2_{Si}$, and/or $q^2_{Ga}$ respectively, and x2 is the summation of $q^2_{Sc}$, $q^2_{Ti}$, $q^2_V$, $q^2_{Cr}$, $q^2_{Mn}$, $q^2_{Co}$, $q^2_{Ni}$, $q^2_{Cu}$, $q^2_{Zn}$, $q^2_Y$, $q^2_{Zr}$, $q^2_{Nb}$, $q^2_{Mo}$, $q^2_{Tc}$, $q^2_{Ru}$, $q^2_{Rh}$, $q^2_{Pd}$, $q^2_{Ag}$, $q^2_{Cd}$, $q^2_{La}$, $q^2_{Hf}$, $q^2_{Ta}$, $q^2_W$, $q^2_{Re}$, $q^2_{Os}$, $q^2_{Ir}$, $q^2_{Pt}$, $q^2_{Au}$, $q^2_{Hg}$, $q^2_{Ce}$, $q^2_{Eu}$, $q^2_{Er}$, $q^2_{Tm}$, $q^2_{Si}$, and/or $q^2_{Ga}$, as will be understood by a skilled person.

In some embodiments of the multicomponent iron catalyst of Formula (I) for synthesis of ammonia from $N_2$ and $H_2$, the iron crystal has a body-centered-cubic crystal lattice having one lattice point in the center of the unit cell in addition to the eight corner points of a cube. It has a net total of 2 lattice points per unit cell ($\frac{1}{8} \times 8 + 1$).

In some embodiments of the multicomponent iron catalyst of in Formula (I), each of the first layer, the second layer, and the third layer are on Fe(111) face. As used herein, an Fe(111) face refers to a crystal face of iron wherein Miller indices h, k, l are 1, 1, and 1 respectively.

In some embodiments of the multicomponent iron catalyst of in Formula (I), in Formula (I) each of the first layer, the second layer, and the third layer are on Fe(211) face. As used herein, an Fe(211) face refers to a crystal face of iron wherein Miller indices h, k, l are 2, 1, and 1 respectively.

In some embodiments of the multicomponent iron catalyst of in Formula (I) for synthesis of ammonia from $N_2$ and $H_2$, x0 is preferably equal to or larger than any of 5 times of x1 or 5 times of x2.

In some embodiments of the multicomponent iron catalyst of in Formula (I) for synthesis of ammonia from $N_2$ and $H_2$, x0 is preferably equal to or larger than any of 10 times of x1 or 10 times of x2.

In some embodiments of the multicomponent iron catalyst of in Formula (I) for synthesis of ammonia from $N_2$ and $H_2$, x1 is preferably equal to or larger than any of 5 times of x0 or 5 times of x2.

In some embodiments of the multicomponent iron catalyst of in Formula (I) for synthesis of ammonia from $N_2$ and $H_2$, x1 is preferably equal to or larger than any of 10 times of x0 or 10 times of x2.

In some embodiments of the multicomponent iron catalyst of in Formula (I) for synthesis of ammonia from $N_2$ and $H_2$, x2 is preferably equal to or larger than any of 5 times of x0 or 5 times of x1.

In some embodiments of the multicomponent iron catalyst of in Formula (I) for synthesis of ammonia from $N_2$ and $H_2$, x2 is preferably equal to or larger than any of 10 times of x0 or 10 times of x1.

In some embodiments of the multicomponent iron catalyst of in Formula (I) for synthesis of ammonia from $N_2$ and $H_2$, each x0, x1, and x2 each preferably range independently from 0 to 0.4.

In some embodiments of the multicomponent iron catalyst of Formula (I) for synthesis of ammonia from $N_2$ and $H_2$,
the at least one dopant $Q^0$, $Q^1$, and $Q^2$ are each independently selected from Cr, Co, Ni, Cu, Zn, Rh, Pd, Ag, Cd, Ir, Pt, Au, Si, Ga or any combination thereof,
x0 is the summation of $q^0_{Cr}$, $q^0_{Co}$, $q^0_{Ni}$, $q^0_{Cu}$, $q^0_{Zn}$, $q^0_{Rh}$, $q^0_{Pd}$, $q^0_{Ag}$, $q^0_{Cd}$, $q^0_{Ir}$, $q^0_{Pt}$, $q^0_{Au}$, $q^0_{Si}$, and $q^0_{Ga}$ present in the first layer,
x1 is the summation of $q^1_{Cr}$, $q^1_{Co}$, $q^1_{Ni}$, $q^1_{Cu}$, $q^1_{Zn}$, $q^1_{Rh}$, $q^1_{Pd}$, $q^1_{Ag}$, $q^1_{Cd}$, $q^1_{Ir}$, $q^1_{Pt}$, $q^1_{Au}$, $q^1_{Si}$, and $q^1_{Ga}$
x2 is the summation of $q^2_{Cr}$, $q^2_{Co}$, $q^2_{Ni}$, $q^2_{Cu}$, $q^2_{Zn}$, $q^2_{Rh}$, $q^2_{Pd}$, $q^2_{Ag}$, $q^2_{Cd}$, $q^2_{Ir}$, $q^2_{Pt}$, $q^2_{Au}$, $q^2_{Si}$, and $q^2_{Ga}$, and
x0, x1, and x2 each range independently from 0 to 0.4 with the proviso that x0+x1+x2 is >0.2, preferably ranging from 0.2 to 0.4, is preferably less than 1.2;
Preferably in some of these embodiments,
a sum of $q^0_{Cu}$, $q^0_{Zn}$, $q^0_{Rh}$, $q^0_{Pd}$, $q^0_{Ag}$, $q^0_{Cd}$, $q^0_{Pt}$, and $q^0_{Au}$ is equal to or larger than any of 5 times of sum of $q^1_{Cu}$, $q^1_{Zn}$, $q^1_{Rh}$, $q^1_{Pd}$, $q^1_{Ag}$, $q^1_{Cd}$, $q^1_{Pt}$, and $q^1_{Au}$ or 5 times of sum of $q^2_{Cu}$, $q^2_{Zn}$, $q^2_{Rh}$, $q^2_{Pd}$, $q^2_{Ag}$, $q^2_{Cd}$, $q^2_{Pt}$, and $q^2_{Au}$; preferably equal to or larger than any of 10 times of sum of $q^1_{Cu}$, $q^1_{Zn}$, $q^1_{Rh}$, $q^1_{Pd}$, $q^1_{Ag}$, $q^1_{Cd}$, $q^1_{Pt}$, and $q^1_{Au}$ or 10 times of sum of $q^2_{Cu}$, $q^2_{Zn}$, $q^2_{Rh}$, $q^2_{Pd}$, $q^2_{Ag}$, $q^2_{Cd}$, $q^2_{Pt}$, and $q^2_{Au}$; most preferably equal to or larger than any 20 times of sum of $q^1_{Cu}$, $q^1_{Zn}$, $q^1_{Rh}$, $q^1_{Pd}$, $q^1_{Ag}$, $q^1_{Cd}$, $q^1_{Pt}$, and $q^1_{Au}$ or 20 times of sum of $q^2_{Cu}$, $q^2_{Zn}$, $q^2_{Rh}$, $q^2_{Pd}$, $q^2_{Ag}$, $q^2_{Cd}$, $q^2_{Pt}$, and $q^2_{Au}$;
a sum of $q^1_{Cr}$, $q^1_{Co}$, $q^1_{Ni}$, and $q^1_{Si}$ is equal to or larger than any of 5 times of sum of $q^0_{Cr}$, $q^0_{Co}$, $q^0_{Ni}$, and $q^0_{Si}$ or 5 times of sum of $q^2_{Cr}$, $q^2_{Co}$, $q^2_{Ni}$, and $q^2_{Si}$; preferably equal to or larger than any of 10 times of sum of $q^0_{Cr}$, $q^0_{Co}$, $q^0_{Ni}$, and $q^0_{Si}$ or 10 times of sum of $q^2_{Cr}$, $q^2_{Co}$, $q^2_{Ni}$, and $q^2_{Si}$; most preferably equal to or larger than any 20 times of sum of $q^0_{Cr}$, $q^0_{Co}$, $q^0_{Ni}$, and $q^0_{Si}$ or 20 times of sum of $q^2_{Cr}$, $q^2_{Co}$, $q^2_{Ni}$, and $q^2_{Si}$; and/or
a sum of sum of $q^2_{Ir}$, and $q^2_{Ga}$ is equal to or larger than any of 5 times of sum of sum of $q^0_{Ir}$, and $q^0_{Ga}$ or 5 times of sum of sum of $q^1_{Ir}$, and $q^1_{Ga}$; preferably equal to or larger than any of 10 times of sum of $q^0_{Ir}$, and $q^0_{Ga}$ or 10 times of sum of $q^1_{Ir}$, and $q^1_{Ga}$; most preferably equal to or larger than any 20 times of sum of $q^0_{Ir}$, and $q^0_{Ga}$ or 20 times of sum of $q^1_{Ir}$, and $q^1_{Ga}$.

In some embodiments of the multicomponent iron catalyst of Formula (I) for synthesis of ammonia from $N_2$ and $H_2$, the at least one dopant $Q^0$, $Q^1$, and $Q^2$ are each independently selected from Rh, Pd, Pt, Cu, Zn, Ag, Au, and Cd, or any combination thereof,
x0 is the summation $q^0_{Rh}$, $q^0_{Pd}$, $q^0_{Pt}$, $q^0_{Cu}$, $q^0_{Zn}$, $q^0_{Ag}$, $q^0_{Au}$, and/or $q^0_{Cd}$ present in the first layer,
x1 is the summation of $q^0_{Rh}$, $q^0_{Pd}$, $q^0_{Pt}$, $q^1_{Cu}$, $q^1_{Zn}$, $q^1_{Ag}$, $q^1_A$ and/or $q^0_{Cd\,u}$, present in the second layer,
x2 is the summation $q^2_{Rh}$, $q^1_{Pd}$, $q^2_{Pt}$, $q^2_{Cu}$, $q^2_{Zn}$, $q^2_{Ag}$, $q^2_{Au}$, and/or $q^2_{Cd}$ present in the third layer, and
x0, x1, and x2 each range independently from 0 to 0.4 with the proviso that x0+x1+x2 is >0.2, preferably ranging from 0.2 to 0.4, is preferably less than 1.2.

In preferred embodiments of the multicomponent iron catalyst of in Formula (I) for synthesis of ammonia from $N_2$ and $H_2$,
$Q^0$ is selected from Cu, Zn, Rh, Pd, Ag, Cd, Pt, and Au, or any combination thereof, wherein each dopant on the first layer is present in a corresponding atom percentage of $q^0_{Cu}$, $q^0_{Zn}$, $q^0_{Rh}$, $q^0_{Pd}$, $q^0_{Ag}$, $q^0_{Cd}$, $q^0_{Pt}$, and $q^0_{Au}$;
$Q^1$ is selected from Cu, Zn, Rh, Pd, Ag, Cd, Pt, and Au, or any combination thereof, wherein each dopant on the second layer is present in a corresponding atom percentage of $q^1_{Cu}$, $q^1_{Zn}$, $q^1_{Rh}$, $q^1_{Pd}$, $q^1_{Ag}$, $q^1_{Cd}$, $q^1_{Pt}$, and $q^1_{Au}$;
$Q^2$ is selected from Cu, Zn, Rh, Pd, Ag, Cd, Pt, and Au, or any combination thereof, wherein each dopant on the third layer is present in a corresponding atom percentage of $q^2_{Cu}$, $q^2_{Zn}$, $q^2_{Rh}$, $q^2_{Pd}$, $q^2_{Ag}$, $q^2_{Cd}$, $q^2_{Pt}$, and $q^2_{Au}$;
x0 is equal to or larger than any of 5 times of x1 or 5 times of x2, preferably x0 is equal to or larger than any of 10 times of x1 or 10 times of x2, and most preferably x0 is equal to or larger than any of 20 times of x1 or 20 times of x2, and
x0 ranges from 0.2 to 0.4,
wherein
x0 is the summation of $q^0_{Cu}$, $q^0_{Zn}$, $q^0_{Rh}$, $q^0_{Pd}$, $q^0_{Ag}$, $q^0_{Cd}$, $q^0_{Pt}$, and $q^0_{Au}$;
x1 is the summation of $q^1_{Cu}$, $q^1_{Zn}$, $q^1_{Rh}$, $q^1_{Pd}$, $q^1_{Ag}$, $q^1_{Cd}$, $q^1_{Pt}$, and $q^1_{Au}$; and
x2 is the summation of $q^2_{Cu}$, $q^2_{Zn}$, $q^2_{Rh}$, $q^2_{Pd}$, $q^2_{Ag}$, $q^2_{Cd}$, $q^2_{Pt}$, and $q^2_{Au}$.

In other preferred embodiments of the multicomponent iron catalyst of in Formula (I) for synthesis of ammonia from $N_2$ and $H_2$,
$Q^0$ is selected from the group consisting of Cr, Co, Ni, and Si, or any combination thereof, wherein each dopant on the top layer is present in a corresponding atom percentage $q^0_{Cr}$, $q^0_{Co}$, $q^0_{Ni}$, and $q^0_{Si}$;
$Q^1$ is selected from the group consisting of Cr, Co, Ni, and Si, or any combination thereof, wherein each dopant on the second layer is present in a corresponding atom percentage of $q^1_{Cr}$, $q^1_{Co}$, $q^1_{Ni}$, and $q^1_{Si}$;
$Q^2$ is selected from the group consisting of Cr, Co, Ni, and Si, or any combination thereof, wherein each dopant on the third layer is present in a corresponding atom percentage of $q^2_{Cr}$, $q^2_{Co}$, $q^2_{Ni}$, and $q^2_{Si}$;
x1 is equal to or larger than any of 5 times of x0 or 5 times of x2, preferably x1 is equal to or larger than any of 10 times of x0 or 10 times of x2, and most preferably x1 is equal to or larger than any of 20 times of x0 or 20 times of x2, and
x1 ranges from 0.2 to 0.4.
wherein
x0 is the summation of $q^0_{Cr}$, $q^0_{Co}$, $q^0_{Ni}$, and $q^0_{Si}$;
x1 is the summation of $q^1_{Cr}$, $q^1_{Co}$, $q^1_{Ni}$, and $q^1_{Si}$; and
x2 is the summation of $q^2_{Cr}$, $q^2_{Co}$, $q^2_{Ni}$, and $q^2_{Si}$, wherein In other preferred embodiments of the multicomponent iron catalyst of in Formula (I) for synthesis of ammonia from $N_2$ and $H_2$, wherein
$Q^0$ is selected from the group consisting of Ir, and Ga, or any combination thereof, wherein each dopant on the top layer is present in a corresponding atom percentage of $q^0_{Ir}$, and $q^0_{Ga}$;

$Q^1$ is selected from the group consisting of Ir, and Ga, or any combination thereof, wherein each dopant on the second layer is present in a corresponding atom percentage of $q^1_{Ir}$, and $q^1_{Ga}$;

$Q^2$ is selected from the group consisting of Ir, and Ga, or any combination thereof, wherein each dopant on the third layer is present in a corresponding atom percentage concentration of $q^2_{Ir}$, and $q^2_{Ga}$;

x2 which is sum of $q^2_{Ir}$, and $q^2_{Ga}$ ranges from 0.2 to 0.4, and x2 is equal to or larger than any of 5 times of x0 or 5 times of x1, preferably x2 is equal to or larger than any of 10 times of x0 or 10 times of x1, and most preferably x2 is equal to or larger than any of 20 times of x0 or 20 times of x1, wherein x0 is the summation of $q^0_{Ir}$, and $q^0_{Ga}$;

x1 is the summation of $q^1_{Ir}$, and $q^1_{Ga}$; and x2 is the summation of $q^2_{Ir}$, and $q^2_{Ga}$, In additional preferred embodiments of the multicomponent iron catalyst of Formula (I) for synthesis of ammonia from $N_2$ and $H_2$, $Q^0$ is selected from Rh, Pd, Pt, Cu, Zn, Ag, Au, and Cd, or any combination thereof, wherein Rh, Pd, Pt, Cu, Zn, Ag, Au, and Cd are present in a corresponding atom percentage of $q^0_{Rh}$, $q^0_{Pd}$, $q^0_{Pt}$, $q^0_{Cu}$, $q^0_{Zn}$, $q^0_{Ag}$, $q^0_{Au}$, and $q^0_{Cd}$, and the sum x0 of $q^0_{Rh}$, $q^0_{Pd}$, $q^0_{Pt}$, $q^0_{Cu}$, $q^0_{Zn}$, $q^0_{Ag}$, $q^0_{Au}$, and $q^0_{Cd}$, ranges from 0.2 to 0.4.

In further preferred embodiments of the multicomponent iron catalyst of in Formula (I) for synthesis of ammonia from $N_2$ and $H_2$, $Q^1$ is selected from the group consisting of Ni, Co, Cr, and Si, or any combination thereof, wherein Ni, Co, Cr, and Si are present in a corresponding atom percentage of $q^1_{Ni}$, $q^1_{Co}$, $q^1_{Cr}$, and $q^1_{Si}$, each ranging from 0 to 0.4 with the proviso that the sum of $q^1_{Ni}$, $q^1_{Co}$, $q^1_{Cr}$, and $q^1_{Si}$ x1 ranges from 0.2 to 0.4.

In additional preferred embodiments of the multicomponent iron catalyst of Formula (I) for synthesis of ammonia from $N_2$ and $H_2$, $Q^0$ is selected from Rh, Pd, Pt, Cu, Zn, Ag, Au, and Cd, or any combination thereof, wherein Rh, Pd, Pt, Cu, Zn, Ag, Au, and Cd are present in a corresponding atom percentage of $q^0_{Rh}$, $q^0_{Pd}$, $q^0_{Pt}$, $q^0_{Cu}$, $q^0_{Zn}$, $q^0_{Ag}$, $q^0_{Au}$, and $q^0_{Cd}$, each ranging from 0 to 0.4 with the proviso that the sum of $q^0_{Rh}$, $q^0_{Pd}$, $q^0_{Pt}$, $q^0_{Cu}$, $q^0_{Zn}$, $q^0_{Ag}$, $q^0_{Au}$ x0 ranges from 0.2 to 0.4

In further preferred embodiments, a multicomponent iron catalyst of Formula (I) as described herein $Q_0$ comprises Rh, Pt, Pd and Cu dopants in a first layer of Fe(111) the respective atom percentage $q^0_{Rh}$, $q^0_{Pt}$, $q^0_{Pd}$, $q^0_{Cu}$ are each ranging from 0 to 0.4 and that the sum of $q^0_{Rh}$, $q^0_{Pt}$, $q^0_{Pd}$, $q^0_{Cu}$ x0 is greater than 0.2 but equal or less than 0.4.

In additional preferred embodiments, a multicomponent iron catalyst of Formula (I) as described herein $Q_0$ comprises Rh, Pt, Pd and Cu dopants in a first layer of Fe(111) the respective atom percentage $q^0_{Rh}$, $q^0_{Pt}$, $q^0_{Pd}$, $q^0_{Cu}$ are each ranging from 0 to 0.4 and that x0 which is the sum of $q^0_{Rh}$, $q^0_{Pt}$, $q^0_{Pd}$, $q^0_{Cu}$ ranges from 0.2 to 0.4; and $Q_1$ comprises Rh, Pt, Pd and Cu dopants in a second layer of Fe(111) wherein the respective atom percentage $q^1_{Rh}$, $q^1_{Pt}$, $q^1_{Pd}$, and $q^1_{Cu}$ each range from 0 to 0.02 and that the x1 which is the sum of $q^1_{Rh}$, $q^1_{Pt}$, $q^1_{Pd}$, and $q^1_{Cu}$ ranges from 0 to 0.02.

In other preferred embodiments, a multicomponent iron catalyst of Formula (I) as described herein $Q_0$ comprises Rh, Pt, Pd and Cu dopants in a first layer of Fe(111) wherein the respective atom percentage $q^0_{Rh}$, $q^0_{Pt}$, $q^0_{Pd}$, and $q^0_{Cu}$ each ranges from 0 to 0.4 and x0 which is the sum of $q^0_{Rh}$, $q^0_{Pt}$, $q^0_{Pd}$, and $q^0_{Cu}$ ranges from 0.2 to 0.4; and $Q_2$ comprises Rh, Pt, Pd and Cu dopants in a third layer of Fe(111) wherein the respective atom percentage $q^2_{Rh}$, $q^2_{Pt}$, $q^2_{Pd}$, and $q^2_{Cu}$ each ranges from 0 to 0.02 and x2 which is the sum of $q^2_{Rh}$, $q^2_{Pt}$, $q^2_{Pd}$, and $q^2_{Cu}$ ranges from 0 to 0.02.

In further preferred embodiments, a multicomponent iron catalyst of Formula (I) as described herein $Q_0$ comprises Rh, Pt, Pd and Cu dopants in a first layer of Fe(111) wherein the respective atom percentage $q^0_{Rh}$, $q^0_{Pt}$, $q^0_{Pd}$, and $q^0_{Cu}$ are each ranging from 0 to 0.4 and x0 which is the sum of the sum of $q^0_{Rh}$, $q^0_{Pt}$, $q^0_{Pd}$, $q^0_{Cu}$ is greater than 0.2 but equal or less than 0.4, $Q_1$ comprises Rh, Pt, Pd and Cu dopants in a second layer of Fe(111) which contain wherein the respective atom percentage $q^1_{Rh}$, $q^1_{Pt}$, $q^1_{Pd}$, and $q^1_{Cu}$ each ranges from 0 to 0.04 and x1 which is the sum of the sum of $q^1_{Rh}$, $q^1_{Pt}$, $q^1_{Pd}$, $q^1_{Cu}$ is less than 10% of x0, preferably less than less than 5% of x0, and $Q_2$ comprises Rh, Pt, Pd and Cu dopants in a third layer of Fe(111) wherein the respective atom percentage concentration $q^2_{Rh}$, $q^2_{Pt}$, $q^2_{Pd}$, $q^2_{Cu}$ each ranges from 0 to 0.04 and x2 which is the sum of $q^2_{Rh}$, $q^2_{Pt}$, $q^2_{Pd}$, $q^2_{Cu}$ is less than 10% of x0, preferably less than less than 5% of x0.

In further preferred embodiments, of the multicomponent iron catalyst of Formula (I) for synthesis of ammonia from $N_2$ and $H_2$, $Q^0$ is Zn, and $q^0_{Zn}$ ranges from 0.2 to 0.4.

In additional preferred embodiments, of the multicomponent iron catalyst of Formula (I) for synthesis of ammonia from $N_2$ and $H_2$, $Q^1$ is Si, and $q^1_{Si}$ is greater than 0.2 and less than or equal to 0.4.

In further preferred embodiments, of the multicomponent iron catalyst of Formula (I) for synthesis of ammonia from $N_2$ and $H_2$, $Q^1$ is Si, and $q^1_{Si}$ is greater than 0.2 and less than or equal to 0.3.

In additional preferred embodiments, of the multicomponent iron catalyst of Formula (I) for synthesis of ammonia from $N_2$ and $H_2$, $Q^1$ is Si, and $q^1_{Si}$ is greater than 0.22 and less than or equal to 0.28

In further preferred embodiments, of the multicomponent iron catalyst of Formula (I) for synthesis of ammonia from $N_2$ and $H_2$, $Q^1$ is Si, and $q^1_{Si}$ is greater than 0.24 and less than or equal to 0.26.

In additional preferred embodiments of the multicomponent iron catalyst of in Formula (I) for synthesis of ammonia from $N_2$ and $H_2$, $Q^0$ comprises Zn present in atom percentage of $q^0_{Zn}$, and $Q^1$ comprises Ni, Co, and Si, or any combination thereof, wherein Ni, Co, and Si are present in a corresponding atom percentage of $q^1_{Ni}$, $q^1_{Co}$, and $q^1_{Si}$, each ranging from 0 to 0.4 and the sum of $q^0_{Zn}$, $q^1_{Ni}$, $q^1_{Co}$, and $q^1_{Si}$ x1 ranges from 0.2 to 0.4.

In further preferred embodiments of the multicomponent iron catalyst of in Formula (I) for synthesis of ammonia from $N_2$ and $H_2$, $Q^0$ comprises Zn present in atom percentage of $q^0_{Zn}$, wherein $q^0_{Zn}$ is greater than 0 and less than or equal to 0.4, and $Q^1$ comprises Cr, Ni, Co, and Si, or any combination thereof, wherein Cr, Ni, Co, and Si are present in a corresponding atom percentage of $q^1_{Cr}$, $q^1_{Ni}$, $q^1_{Co}$, and $q^1_{Si}$, each ranging from 0 to 0.4 and wherein sum of $q^0_{Zn}$, $q^1_{Cr}$, $q^1_{Ni}$, $q^1_{Co}$, and $q^1_{Si}$ ranges from 0.2 to 0.4.

In additional embodiments of the multicomponent iron catalyst of in Formula (I) for synthesis of ammonia from $N_2$ and $H_2$, $Q^0$ comprises Zn present in atom percentage $q^0_{Zn}$, ranging from 0.1 to 0.4, and $Q^1$ comprises Ni present in atom percentage $q^1_{Ni}$, ranging from 0.1 to 0.4, wherein $q^0_{Zn}+q^1_{Ni}$ optionally ranges from 0.2 to 0.4.

In some embodiments of the multicomponent iron catalyst of in Formula (I) for synthesis of ammonia from $N_2$ and $H_2$, $Q^0$ comprises Zn present in atom percentage of $q^0_{Zn}$;

$Q^1$ comprises Ni present in atom percentage of $q^1_{Ni}$, wherein $q^0_{Zn}$ is equal or higher than $q^1_{Ni}$, and wherein $q^0_{Zn}+q^1_{Ni}$ optionally ranges from 0.2 to 0.4.

In some of the preferred embodiments of the multicomponent iron catalyst of in Formula (I) for synthesis of ammonia from $N_2$ and $H_2$, x0 is preferably equal to or larger than any one of 10 times of x1 or 10 times of x2.

In some of the preferred embodiments of the multicomponent iron catalyst of in Formula (I) for synthesis of ammonia from $N_2$ and $H_2$, x1 is preferably equal to or larger than any of 5 times of x0 or 5 times of x2.

In some of the preferred embodiments of the multicomponent iron catalyst of in Formula (I) for synthesis of ammonia from $N_2$ and $H_2$, x1 is preferably equal to or larger than any of 10 times of x0 or 10 times of x2.

In some embodiments of the preferred multicomponent iron catalyst of in Formula (I) for synthesis of ammonia from $N_2$ and $H_2$, x2 is preferably equal to or larger than any of 5 times of x0 or 5 times of x1.

In some embodiments of the preferred multicomponent iron catalyst of in Formula (I) for synthesis of ammonia from $N_2$ and $H_2$, x0, x1, and x2 each x0, x1, and x2 each range independently from 0 to 0.4.

In some embodiments of the multicomponent iron catalyst of in Formula (I) for synthesis of ammonia from $N_2$ and $H_2$, the third layer of the iron crystal or iron film can be deposited on a substrate comprising a base layer consisting of at least three layers of iron atoms.

Figure 4:
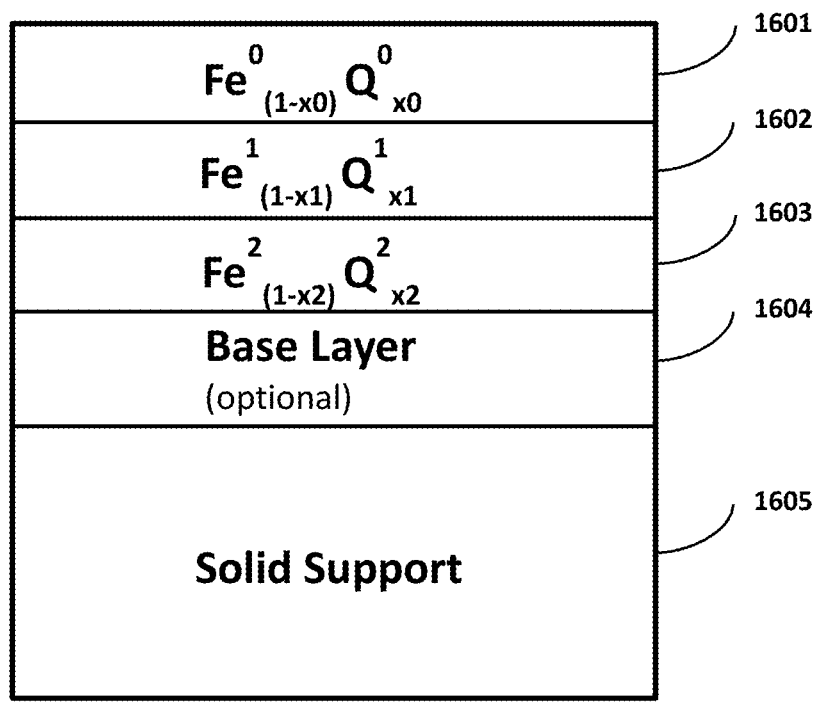
FIG. 4 illustrates an embodiment of the three layers iron catalyst on a substrate herein described.

Reference is made to FIG. 4 which shows a schematic representation of an embodiment of the multicomponent iron catalyst for ammonia synthesis from hydrogen and nitrogen as described herein. In the schematics of FIG. 4, an optional base layer (1604) is disposed on the solid support (1605) to provide a multicomponent catalysts material. The solid support can be selected from the group consisting of metal including bulk iron, metal oxide including alumina, solid inorganic oxide, ceramics, glass, or any combinations thereof. On the optional base layer is disposed a third iron layer $Fe^2_{(1-x2)}Q^2_{x2}$ which is doped with dopant $Q^2_{x2}$. As described herein x2 refers to the atomic percentage of dopant $Q^2$ on the third iron layer. On the third iron layer $Fe^2_{(1-x2)}Q^2_{x2}$ shown as element (1603) is disposed a second iron layer $Fe^1_{(1-x1)}Q^1_{x1}$ which doped with dopant $Q^1_{x1}$. As described herein x1 refers to the atomic percentage of dopant $Q^1$ on the second iron layer. On the second iron layer $Fe^1_{(1-x1)}Q^1_{x1}$ shown as element (1602) is disposed a top iron layer $Fe^0_{(1-x0)}Q^0_{x0}$ (1601) which is doped with dopant $Q^0_{x0}$. As described herein x0 refers to the atomic percentage of dopant $Q^0$ on the top iron layer.

In embodiment of catalyst of Formula (I) herein described a film of Fe was deposited on Al2O3 and then monolayers of the Ni and Si dopants on the top followed by annealing.

A multicomponent iron catalyst of Formula (I) here described, can be produced by a method comprising depositing a third layer of iron atoms $Fe^2$ on a base layer, optionally doping the third layer with dopant $Q^2$, depositing a second layer of iron atoms $Fe^1$ on the third layer of iron atoms $Fe^2$, optionally doping the second layer with dopant $Q^1$, depositing a top layer of iron atoms $Fe^0$ on the second layer of iron atoms $Fe^1$, optionally doping the first layer with dopant $Q^0$, to obtain a three layers structure having a Formula (I) herein described.

In some embodiments, in the method of producing a multicomponent iron catalyst of Formula (I) as described herein, the depositing and/or doping is performed by a step selected from the group consisting of epitaxy, ion sputtering, controlled surface reactions (CSR), atomic layer deposition (ALD), cluster beam deposition, colloidal synthesis and galvanic displacement or any combinations thereof. Optionally the method of producing a multicomponent iron catalyst of Formula (I) as described herein further includes annealing.

In some embodiments, a method of atomic layer deposition (ALD) for preparing a multicomponent iron catalyst of Formula (I) is provided, the method comprising providing a solid support, optionally depositing a base layer of at least three iron layers on the solid support, depositing a third layer of iron and dopant $Fe^2_{(1-x2)}Q^2_{x2}$ on the substrate if present or depositing a third layer of iron $Fe^2_{(1-x2)}Q^2_{x2}$ on the solid support in the absence of the substrate, depositing a second layer of iron $Fe^1_{(1-x1)}Q^1_{x1}$ on the third layer of iron $Fe^2_{(1-x2)}Q^2_{x2}$, and depositing a top layer of iron $Fe^0_{(1-x0)}Q^0_{x0}$ on the second layer of iron $Fe^1_{(1-x1)}Q^1_{x1}$, wherein the ratio of atoms on the third layer to the top layer is b, and the ratio of atoms on the second layer to the top layer is a, to obtain multicomponent iron catalyst of Formula (I).

In In some embodiments, a method of atomic layer deposition (ALD) for preparing a multicomponent iron catalyst of Formula (I) is provided, the method comprising providing a solid support, wherein the solid support comprises the solid support is selected from the group consisting of metal, metal oxide, solid inorganic oxide, ceramics, glass, or any combinations thereof.

In some embodiments, a method of epitaxy for preparing a multicomponent iron catalyst of Formula (I) is provided, the method comprising providing a solid support, optionally depositing a base layer of at least three iron layers on the solid support, depositing a third layer of iron and dopant $Fe^2_{(1-x2)}Q^2_{x2}$ on the substrate if present or depositing a third layer of iron $Fe^2_{(1-x2)}Q^2_{x2}$ on the solid support in the absence of the substrate, depositing a second layer of iron $Fe^1_{(1-x1)}Q^1_{x1}$ on the third layer of iron $Fe^2_{(1-x2)}Q^2_{x2}$, and depositing a top layer of iron $Fe^0_{(1-x0)}Q^0_{x0}$ on the second layer of iron $Fe^1_{(1-x1)}Q^1_{x1}$, wherein the ratio of atoms on the third layer to the top layer is b, and the ratio of atoms on the second layer to the top layer is a, to obtain multicomponent iron catalyst of Formula (I).

In some embodiments, a method of epitaxy for preparing a multicomponent iron catalyst of Formula (I) is provided, the method comprising providing a solid support, wherein the solid support is selected from the group comprising metal, metal oxide, solid inorganic oxide, ceramics, glass, or any combinations thereof.

In some embodiments, a method of preparing a stable multicomponent iron catalyst of Formula (I) is provided, the method comprising providing a solid support, optionally depositing a base layer of at least three iron layers on the solid support, depositing a third layer of iron and dopant $Fe^2_{(1-x2)}Q^2_{x2}$ on the base layer if present or depositing a third layer of iron $Fe^2_{(1-x2)}Q^2_{x2}$ on the solid support in the absence of the base layer, depositing a second layer of iron $Fe^1_{(1-x0)}Q^1_{x1}$ on the third layer of iron $Fe^2_{(1-x2)}Q^2_{x2}$, and depositing a top layer of iron $Fe^0_{(1-x0)}Q^0_{x0}$ on the second layer of iron $Fe^1_{(1-x1)}Q^1_{x1}$, wherein the ratio of atoms on the third layer to the top layer is b, and the ratio of atoms on the second layer to the top layer is a, to obtain a multicomponent iron catalyst of Formula (I), wherein depositing optionally comprise annealing to obtain the multicomponent iron catalyst of Formula (I) as herein described.

In some embodiments, one or more multicomponent iron catalysts of Formula (I) in accordance with the disclosure can be comprised in a multicomponent iron catalyst material wherein the third layer of the iron crystal or iron film is deposited on a substrate comprising a base layer consisting of at least three layers of iron atoms, and wherein the substrate is anchored on a suitable solid support for a catalysis process.

In particular, in some embodiments exemplified by the schematic illustration of FIG. 4, a multicomponent iron catalyst material comprises a multicomponent iron catalyst for synthesis of ammonia from $N_2$ and $H_2$ comprising the three layers structure having a Formula (I) herein described schematically represented by layers (1601) (1602) and (1603), wherein the third layer of the iron crystal or iron film (1603) is deposited on a substrate comprising a base layer (1604) consisting of at least three layers of iron atoms, wherein the substrate is anchored on a suitable solid support (1605) for a catalysis process.

In some embodiments, the base layer comprises three layers of iron atoms of Fe(111) face or three layers of iron atoms of Fe(211) face.

In some embodiments, the base layer is disposed on a solid support capable of forming stable binding interaction with the base layer. The exemplary binding interaction includes van der Waals force, electrostatic interaction, dipolar interaction, charge-dipole interaction, or dispersive interactions. The term stable binding interaction is meant to define a binding force between the base layer and the solid support which is sufficiently strong to impart structural integrity during the catalytic process as described herein. Exemplary solid support includes metal including bulk iron, metal oxide, solid inorganic oxide, ceramics, glass, or any combinations thereof.

In some embodiments, in the multicomponent iron catalyst material as described herein, the base layer of at least three layers of iron atoms comprises three layers of Fe(111) face atoms.

In some embodiments, in the multicomponent iron catalyst material as described herein, the base layer of at least three layers of iron atoms comprises three layers of Fe(211) face atoms.

In some embodiments, in the multicomponent iron catalyst material as described herein, the solid support is selected from the group consisting of metal, metal oxide, solid inorganic oxide, ceramics, glass, or any combinations thereof.

In some embodiments, in the multicomponent iron catalyst material as described herein, the solid support is a metal of iron.

In some embodiments, in the multicomponent iron catalyst material as described herein, the solid support is a silicon dioxide.

In some embodiments, in the multicomponent iron catalyst material as described herein, the solid support is alumina.

In some embodiments, in the multicomponent iron catalyst material as described herein, the solid support is a zirconium oxide.

A multicomponent iron catalyst material comprising a multicomponent catalyst herein described can be further produced by a method comprising
providing a substrate comprising a solid support and a base layer consisting of at least three layers of iron atoms, wherein the base layer is anchored on a suitable solid support for a catalysis process.

The method to provide a multicomponent iron catalyst material comprising a catalyst of Formula (I) herein described further comprises
depositing a third layer of iron atoms $Fe^2$ on the base layer, optionally doping the third layer with dopant $Q^2$,
depositing a second layer of iron atoms $Fe^1$ on the third layer of iron atoms $Fe^2$, optionally doping the second layer with dopant $Q^1$,
depositing a first layer of iron atoms $Fe^0$ on the second layer of iron atoms $Fe^1$, optionally doping the first layer with dopant $Q^0$,
obtaining the multicomponent iron catalyst material comprising a three layers structure having a Formula (I), wherein the depositing optionally includes annealing.

The method to provide a multicomponent iron catalyst material comprising a catalyst of Formula (I) herein described comprises
providing a bulk iron alloy containing sufficient amount of dopant $Q^0$, dopant $Q^1$, and dopant $Q^2$,
dividing, sizing, and/or shaping the bulk iron alloy of dopant $Q^0$, dopant $Q^1$, and dopant $Q^2$ containing sufficient amount of dopant $Q^0$, dopant $Q^1$, and dopant $Q^2$ to a form suitable for catalysis reaction, including particulate shapes of a diameter ranging from 1 microns to 1000 microns or film shape of 1 microns to 1000 microns in thickness,
annealing the divided, sized, and/or shaped the bulk iron alloy of dopant $Q^0$, dopant $Q^1$, and dopant $Q^2$ to obtain the multicomponent iron catalyst material comprising a catalyst of Formula (I).

In some embodiments an iron catalyst of Formula (I) in accordance with the disclosure can be provided by a method of producing a multicomponent iron catalyst comprising
providing an $Fe^0\ Fe^1\ Fe^2$ iron atoms three layers structure,
contacting a dopant or a dopant precursor with the $Fe^0\ Fe^1\ Fe^2$ iron atoms three layers structure,
annealing the $Fe^0\ Fe^1\ Fe^2$ iron atoms three layers structure following the contacting, to allow the dopant replace part of the $Fe^0$ iron atoms with a $Q^0$ dopant, part of the $Fe^1$ iron atoms with a $Q^1$ dopant and part of the $Fe^2$ iron atoms with a dopant $Q^2$.

The term annealing as used herein refers to a process of diffusion or migration of a dopant atom from one atomic position to another atomic position of a solid material or from one solid material to another solid material that are in physical contact under conditions to allow formation of a stable composition of the solid material containing the dopant.

In some embodiments, a multicomponent catalysts of Formula (I) can be prepared by epitaxy, ion sputtering, controlled surface reactions (CSR), atomic layer deposition (ALD), cluster beam deposition, colloidal synthesis and galvanic displacement.

In some embodiments, a multicomponent catalysts of Formula (I) prepared by epitaxy, ion sputtering, controlled surface reactions (CSR), atomic layer deposition (ALD), cluster beam deposition, colloidal synthesis and galvanic displacement can be annealed and converted to a thermodynamically stable state.

In some embodiments, the annealing of dopant in an Fe can occurs at a temperature ranging from 100 to 700° C.

In some embodiments, the annealing of dopant in an Fe can occurs in 0.1 to 24 hours. The calculated atomic radii in Angstrom (Å) for exemplary dopants and iron are shown in the parenthesis for each elements Sc (1.84), Ti (1.76), V (1.71), Cr (1.66), Mn (1.61), Fe (1.56), Co (1.52), Ni (1.49), Cu (1.45), Zn (1.42), Y (2.12), Zr (2.06), Nb (1.98), Mo (1.90), Tc (1.83), Ru (1.78), Rh (1.73), Pd (1.69), Ag (1.65), Cd (1.61), La (2.26), Hf (2.08), Ta (2.00), W (1.93), Re (1.88), Os (1.85), Ir (1.80), Pt (1.77), Au (1.74), Hg (1.71), Ce (2.10), Eu (2.13), Er (2.26), Tm (2.22), Si (1.11), Ga (1.36). (See [37]).

In some embodiment, the relative atom percentage concentration of dopant atoms for the multicomponent catalysts of Formula (I) as described herein are selected based on the relative difference in absolute number in calculated atomic radii from iron. Therefore, when more than one dopant atom is present in at least one of top layer, second layer or third layer of the catalyst, a dopant that is closer in atomic radius to the atomic radius of Fe will be present in a larger amount.

In some embodiments, dopants with corresponding difference in atomic radii from iron in parentheses including Rh (+0.17 Å), Pd (+0.13 Å), Pt (+0.21 Å), Cu (−0.11 Å), Zn (−0.14 Å), Ag (+0.09 Å), Au (+0.18 Å), and Cd (+0.05 Å), or any combination thereof are present in a top layer of the multicomponent catalysts of Formula (I) as described herein, wherein the atom percentage concentration for each dopant is in the decreasing order of $q^o_{Cd}$, $q^o_{Ag}$, $q^o_{Cu}$, $q^o_{Pd}$, $q^o_{Zn}$, $q^o_{Rh}$, $q^o_{Au}$, and $q^o_{Pt}$.

In accordance with the present disclosure, multicomponent catalysts of Formula (I) and related catalyst materials herein described can be used in a method for synthesis of ammonia from $N_2$ and $H_2$ is described. The method for synthesis of ammonia from $N_2$ and $H_2$ comprises contacting $N_2$ and $H_2$ the multicomponent iron catalyst of Formula (I) and/or the multicomponent iron catalyst material comprising the multicomponent iron catalyst of Formula (I) for a time and under conditions to obtain ammonia.

Figure 5:
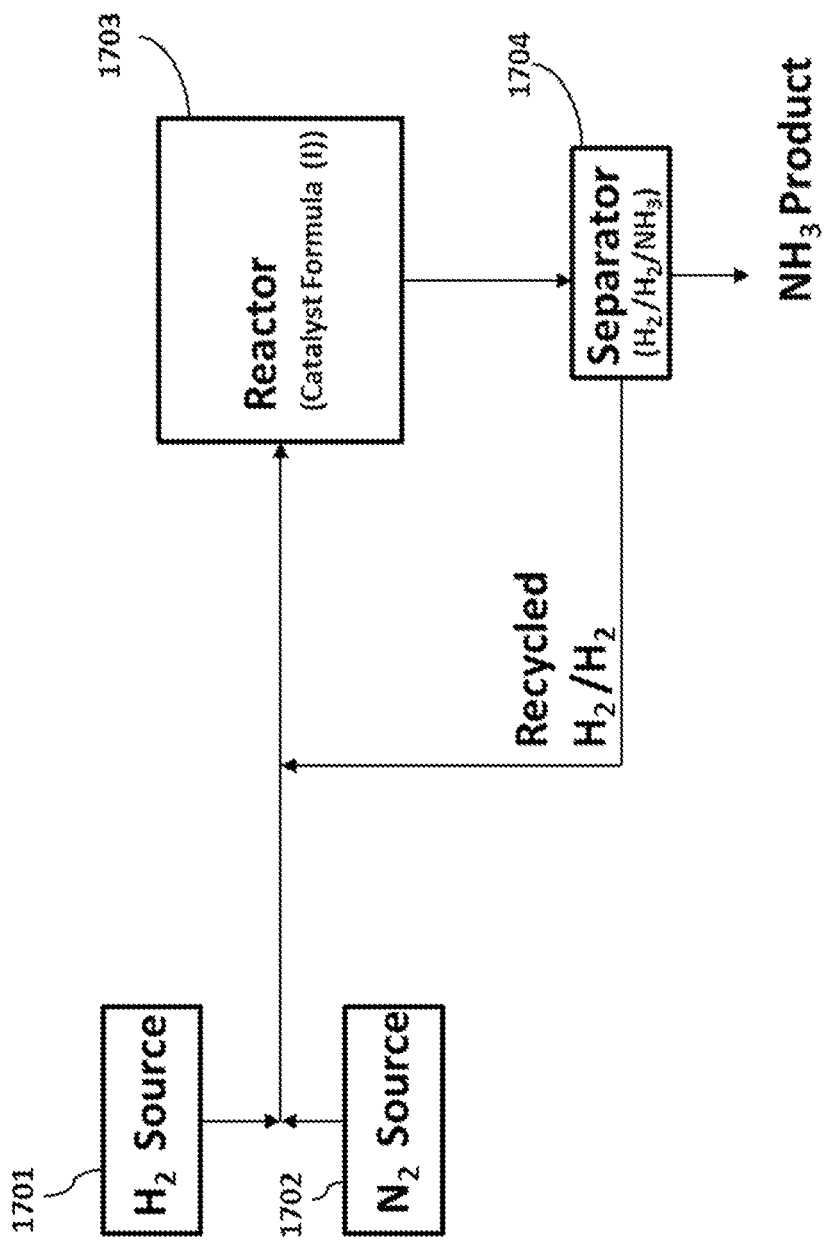
FIG. 5 illustrates an embodiment of hardware implementation for the method for synthesis of ammonia herein described.

Reference is made in this connection to FIG. 5 which shows a schematic illustrating the synthesis ammonia from reaction of hydrogen and nitrogen catalyzed by the catalyst as described herein. A hydrogen source (1701) and a nitrogen source (1702) are provided. The hydrogen and nitrogen are combined and conducted to reactor (1703) containing catalyst of Formula (I) as described herein. The hydrogen and nitrogen are reacted in the reactor (1703) as catalyzed by the catalyst of Formula (I) to form ammonia. The reaction mixture comprising ammonia and the unreacted hydrogen and nitrogen are passed to a separator (1707) in which ammonia product is isolated from hydrogen and nitrogen. The unreacted hydrogen and nitrogen are combined with the fresh hydrogen and nitrogen from hydrogen source (1701) and a nitrogen source (1702) and recycled to the reactor (1703) containing catalyst of Formula (I) for a subsequent reaction cycle forming ammonia from reaction of hydrogen and nitrogen catalyzed by the catalyst as described herein.

In some embodiments, in the method for synthesis of ammonia from $N_2$ and $H_2$ as described herein, the $N_2$ and the $H_2$ are at a partial pressure up to 1 to 250 atmospheric pressure and a temperature of 50 to 650° C.

In some embodiments, in the method for synthesis of ammonia from $N_2$ and $H_2$ as described herein, the $N_2$ and the $H_2$ are at a partial pressure up to 20 to 200 atmospheric pressure and a temperature of 150 to 450° C.

In some embodiment, nitrogen and hydrogen gas are combined to form a mixture. The mixture of nitrogen and hydrogen gas is passed through a catalyst of Formula (I) at a temperature of 50 to 650° C. and wherein the $N_2$ and the $H_2$ are at a partial pressure up to 1 to 250 atmospheric pressure to produce ammonia at in a yield of at least 10% based on $H_2$.

In some embodiments, in the method for synthesis of ammonia from $N_2$ and $H_2$ as described herein, the $N_2$ and the $H_2$ are at a partial pressure up to 25 to 75 atmospheric pressure and a temperature of 175 to 250° C.

In some embodiments, in the method for synthesis of ammonia from $N_2$ and $H_2$ as described herein, the $N_2$ and the $H_2$ are at a combined partial pressure of up to 30 to 50 atmospheric pressure and a temperature of 200 to 225° C.

In some embodiments, the method for synthesis of ammonia from $N_2$ and $H_2$ as described herein, wherein the $N_2$ and the $H_2$ are at a partial pressure up to 30 to 50 atmospheric pressure and a temperature of 200 to 225° C.

Additional, embodiments of the screening methods and related catalysts, material, compositions methods and systems will become apparent to a skilled person upon reading of the entire disclosure inclusive of drawings and claims and are further illustrated with the aid of the following examples which are not intended to be limiting.

EXAMPLES

The following examples show exemplary methods and systems of screening candidate catalysts for energy intensive Haber-Bosch ammonia synthesis and related catalyst obtainable therefrom. A skilled person will be able to apply the guidance provided in the following examples for screening candidate catalysts of other chemical reactions in accordance with the disclosure.

Accordingly, the following examples are provided for further illustration of embodiments of the present disclosure and are not intended to be limiting in any way.

General Computational Procedures

The same first-principles approach as in Ref. [2] was used, i.e., DFT with the Perdew-Burke-Ernzerhof (PBE) [19] [20] exchange-correlation functional including Grimme-D3 empirical corrections for long range London dispersion (van der Waals attraction) [22] i.e. PBE-D3. Small differences in the energetics with respect to Ref. [2] are due to the fact that here the VASP code [19] [20] was consistently used for both gas-phase and surface species instead of the Jaguar code for gas-phase molecules as in Ref. [2] and the reaction network of 26 states have been streamlined to 21, thus leading to small differences in the predicted rates of ammonia production. The electron partial occupancies were determined using the tetrahedron method with Blöchl corrections. It was established that an energy cutoff of 600 eV leads to converged energies, forces and geometries. In all calculations the energy convergence of $10^{-6}$ eV was used for terminating electronic self-consistent field (SCF) and the force criterion of $10^{-3}$ eV/Å. The K-point sampling was chosen to be 4×4×1 in which z direction is the vacuum direction. All calculations are spin-polarized. The PBE-D3(BJ) calculated lattice parameter is 2.807 Å for the bulk Fe bcc structure at 0 K. A slab model with 6 Fe layers was used, of which the top 3 layers are allowed to relax, with the bottom two layers fixed.

15 Å of vacuum was included in the z direction to minimize possible interactions between the replicated cells.

For the phonon calculations density functional perturbation theory (DFPT) is used to calculate the phonon density of states and $10^{-6}$ eV energy convergence threshold. The same procedure was applied for the transition states free energy correction. It is noted that some of the frequencies correspond to hindered translational or rotational modes, for which the harmonic oscillator description is less accurate. In these cases, namely NH3 and N2 desorption calculations, only ZPE corrections is used.

All raw energy data are provided in Table 4 reported in Example 10.

Example 1: Rate Limiting Steps

Figure 6:
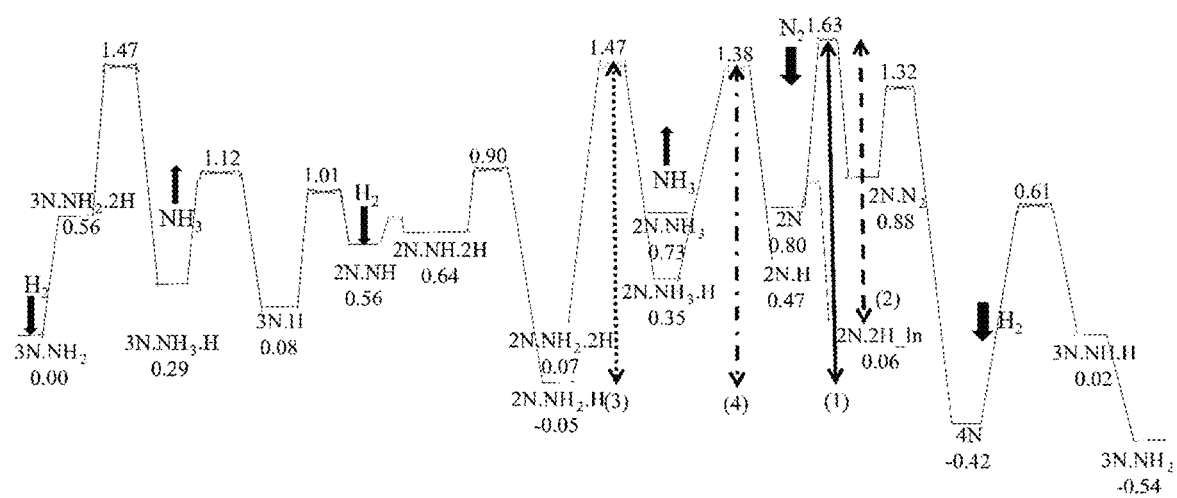
FIG. 6 illustrates a plot showing in one embodiment the standard state free energy diagram at the density functional theory (DFT) with Perdew-Burke-Ernzerhof (PBE) and dispersion (D3) level for ammonia synthesis over a (2×2) unit cell of the Fe(111) surface, evaluated at 673 K, $P(H_2)=15$ atm, $P(N_2)=5$ atm, $P(NH_3)=1$ atm [1] [2]. The barriers selected for high-throughput screening are represented by various vertical lines. Black is the linear pathway for the optimum reaction barriers. The notations for the adsorbed species represent the key configurations (FIG. 8) along the reaction path. Free energies in eV.

Rate limiting steps have been determined on a free energy diagram the exemplary reference catalyst Fe(111) with respect to the chemical reaction Haber-Bosch ammonia synthesis, as illustrated in FIG. 6.

In the illustration of FIG. 6, the rate-determining step having the highest energy barrier corresponds to $N_2$ desorption/dissociation, therefore ranked the first place. The rate-determining step having the second highest energy barrier corresponds to $H_2$ poisoning to the $N_2$ adsorption, ranked the second place. The rate-determining step having the third highest energy barrier corresponds to $NH_x$ hydrogenation, ranked the third place. The rate-determining step having the fourth highest energy barrier corresponds to $NH_3$ desorption, ranked the fourth place (FIG. 6).

Example 2: Exemplary Screening Criteria

In an exemplary embodiment, the following screening criteria were used when empirical correction are applied.

barrier(1)=ΔE{4N->2N[zig-zag]+N2}−0.358 eV constraint: ΔE{2N_N2[γ,zig-zag]->2N[zig-zag]+N2}>0.5 eV barrier(2)=ΔE{2N_2H[linear2]->2N[zig-zag]+H2}+0.113 eV barrier(3)=ΔE{4N+3½H2->2N_NH3H[zig-zag]+NH3}+3.340 eV barrier(4)=ΔE{4N+3½H2->2N_NH3H[zig-zag]+NH3}+3.2955 eV barrier(1-4)=barrier(1-4)+max{ΔE{4N[subsurface-dopant]->4N[surface-dopant]},0}

Example 3: In Silico Strategy for Doped Fe(111) Catalysts for HB Synthesis

In criterion 1, a component of the largest barrier is due to $N_2$ adsorption on 2N[zig-zag] to give 2N_N2[γ,zig-zag], i.e., $N_2$ adsorbed on a top site of the Fe(111) surface (the γ state is named in keeping with Ref. [2]). This barrier is the sum of the reaction free energy (0.08 eV) plus the desorption enthalpy o $N_2$ from 2N_N2[γ,zig-zag]. This component is expected to be roughly constant upon variations of the N2 adsorption energy. It is also noted that there are three possible doping sites for 2N_NH2_H, three doping sites for 2N_N2, and only one doping site for 2N (FIG. 3). The doping site associated with lowest-energy for 2N_NH2_H was used to estimate barrier(1).

Figure 11:
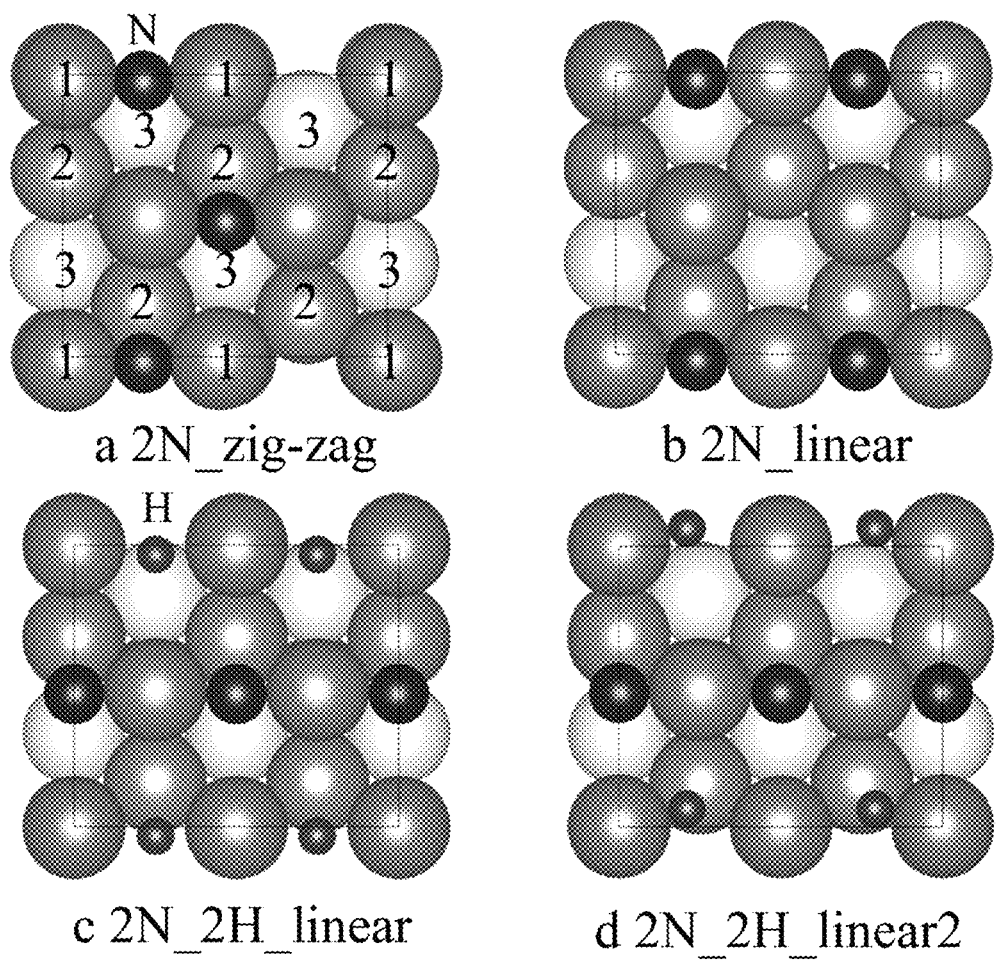
FIG. 11 shows a schematic illustration of: (a) "linear" and (b) "zig-zag" configurations for the 2N system; and (c) linear and (d) linear2 configurations for the 2N_2H system [1]. The 2N_2H[linear] structure is higher in electronic energy by 0.12 eV than 2N_2H[linear2]. However, the free energy of 2N_2H[linear] is 0.02 eV lower than that of 2N_2H[linear2] at 673 K.

In criterion 2, there exist 2 different 2N_2H[linear] structures, that are named as 2N_2H[linear] and 2N_2H[linear2], see FIG. 11(c,d). 2N_2H[linear] is electronically less stable than 2N_2H[linear2] at 0 K but becomes more stable after including entropic corrections at 673 K. 2N_2H[linear2] is used as the reference structure in HTS because of its lower electronic energy.

In criterion 3, the 2N_NH3_H configuration was used, rather than 2N_NH3, which is also involved in the NH3 desorption barrier of the next step: this suggests that the third and fourth criteria might be merged, but they were kept separate because they are physically different and could be formally distinguished using alternative screening criteria for barrier(3), such as the energy difference between 2N_NH2_H and 2N_NH2_2H configurations plus the barrier for the "2N_NH2_2H->2N_NH3_H" step.

In criterion 5, the stability estimation could be improved and made more precise by considering the ΔE of the inverse-segregation process for the resting state of each barrier and add it to that barrier, but the present choice should be sufficient for a first quick screening (under steady-state conditions the most abundant surface configuration exhibit only a partial coverage by NHy-species, such as 2N_NH2_H or 2N_2H, see Table 2 in Ref. [2]).

Overall, the above analysis and results can be summarized into the rationale that the optimal dopant elements should decrease the stability of the resting states (i.e., 2N_NH2_H or 4N configurations) with respect to the active states of the catalyst involved in the absorption and dissociation of N2 (the 2N[zigzag] configuration) as well as the barriers in the hydrogenation of NHy-adsorbed species to $NH_3$, and should also not increase sensitivity to hydrogen poisoning nor hinder the desorption of $NH_3$.

Example 4: kMC Simulations

Rate constants of individual steps are derived from transition state theory as (kBT/h)exp(−ΔG†/kBT), wherein −ΔG† is the difference in free energy between the starting state and the saddle point. For reactions involving adsorption of gas-phase species, transition state theory was used for the reverse desorption process, and microscopic reversibility principle was invoked to calculate the rate of the direct process. 20 independent replicas and 2×109 kMC steps each were used (checking that the results are converged within 5% with respect to a test case using 100 replicas and 2×1010 kMC steps) for a total simulated time of 530 s (pure Fe surface) and 3702 s (Rh-doped surface), under conditions of T=673 K, P(H2)=15 atm, P(N2)=5 atm, and P(NH3)=1 atm.

Example 5: Energy Diagram of Rh-Doped Fe Catalyst

Figure 9:
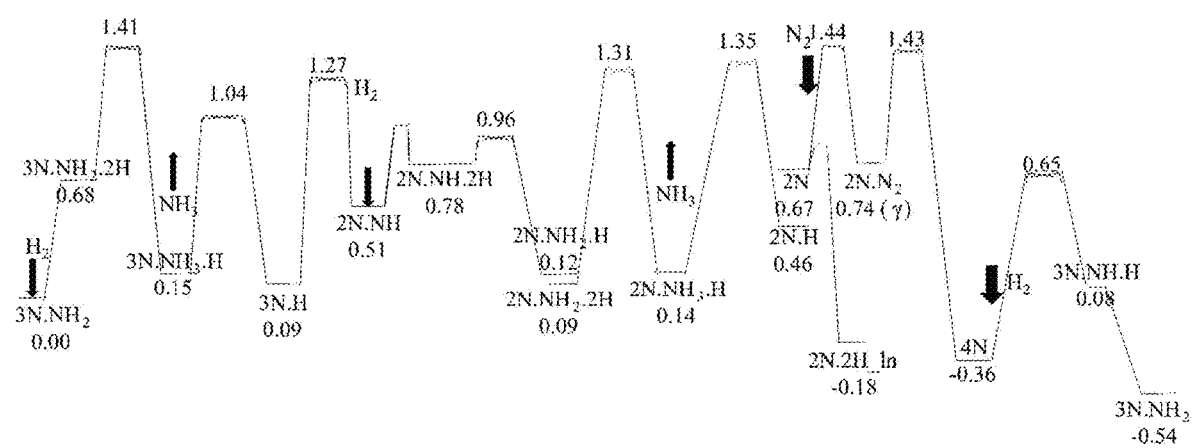
FIG. 9 illustrates a plot showing the standard state energy landscape for $NH_3$ synthesis reactions on Rh-doped Fe(111) surface under 673 K and 20 atm conditions [1]. The lowest energy state $3N\_NH_2$ is taken as reference, with a free energy of zero. Black is the linear pathway from the optimum reaction barriers. The notations for the adsorbed species represent the key configurations (FIG. 12) along the reaction path. To be consistent with FIG. 6, the same symbols are used for adsorbed species.

FIG. 9 displays the reaction energy diagram of Rh-doped Fe system. The three highest-energy states which play the most important role in determining the reaction rate in kMC model are described below.

(1) 2N->2N_N2 ($N_2$ gas->$N_2$ triple bonded, top layer). This step involves N2 adsorption (G†=1.44) and its resting state is 2N_2H[linear] (linear configuration, FIG. 11) with G=−0.18, together making this barrier 1.44+0.18=1.62 in kMC.

(2) 2N_N2->4N ($N_2$*—>N*+N*)G†=1.43 is the highest barrier along $N_2$ dissociation, see FIG. 16. This involves a complex reaction pathway: triple-bonded $N_2$ adsorbed on top of first layer Fe (σN≡N-T or γ)->triple-bonded $N_2$ adsorbed on the second layer (σN≡N—S or δ)->doublebonded $N_2$ to a bridge site ($\pi N=N\eta_2$ or $\alpha$)->single-bonded $N_2$ at a 3-fold site ($2\pi N$—$N\eta_3$ or $\alpha'$)->the dissociated state 4N ($\beta$) (FIG. 16). The maximum barrier is 1.43 eV from the $\alpha'$->$\beta$. All the barriers in the $N_2$ dissociation are considered in the kMC model.

(3) 3N_NH2_2H->3N_NH$_3$_H ($NH_2$*+H*->$NH_3$*). This step involves hydrogenation or H migration (G†=1.41) and its resting state is 3N_NH$_2$ with G=0. Therefore, this barrier is 1.41 in kMC.

Example 6: Analyze Free Energy Network of Haber-Bosch Ammonia Synthesis Process Over Fe(111)

The hierarchical high-throughput screening approach herein described is demonstrated using Haber-Bosch ammonia synthesis process over Fe(111) as an example.

The free-energy reaction network for ammonia synthesis (HB) process over Fe(111) derived in Ref. [2]was used, in which density-functional theory (DFT) predictions[19] [20] [21] [22] free energies and reaction rates used the (2×2) unit cell of Fe(111) (PBE-D3) [19] [20]exchange correlation functional, see Ref. [2]for computational details). This is one of the most extensive first-principles-based investigation of a heterogeneous catalytic reaction ever reported. This free-energy reaction network, evaluated at 673 K, P(H2)=15 atm, P(N2)=5 atm, P(NH3)=1 atm, is shown as a linear diagram in FIG. 6. The predicted Turn-Over-Frequency (TOF) of 17.7 NH3/sec for our 2×2 computational cell is in excellent agreement with the TOF=9.7 NH3/sec from single crystal experiments [2] (changing the barrier for the rate determining step by 0.04 eV, would reduce the predicted rate to 9.7 showing the sensitivity of TOF to the reaction barriers).

The energy diagram shown FIG. 6 suggests that the barrier for N2 absorption/desorption is the highest. But the kinetic Monte Carlo analysis show that the dissociative chemisorption of H2 and the desorption of NH3 play an essential role in providing the empty sites required for the N2 to bind and as the NN bonds are reduced from 3 to 0. As a result, the desorption of NH3 is also rate limiting for Fe(111). Additional potential RDSs involve the successive addition of H* to NHx* via Langmuir-Hinshelwood (LH) additions, leading to 4 possible RDSs, that also depend on H2 chemisorption and NH3 desorption of H. Thus, there are at least 10 potential RDS, each of which may require specific types of sites.

Example 7: Identify and Rank Rate Determining Steps 10 potentially rate determining steps in the free energy network were identified and then partitioned into 4 distinct and diverse processes that may become determining as the Fe catalyst are doped:

(i) activation of the N—N bond (itself composed of 4 different steps, from adsorption from the gas phase to interconversion between different adsorption modes),
(ii) hydrogenation of NHx-adsorbed species (itself also distinguished into 3 different steps with x=0-2),
(iii) desorption of the NH3 product (in 2 different points along the catalytic path), and
(iv) poisoning of catalytically active sites by reactant (H2) or product (NH3) species.

All 10 of these distinct steps could be rate-determining. As the first step, the full kMC kinetic analysis was used to simplify this reaction network to single out the minimum number of processes (4) and corresponding reaction free energies required to estimate the overall catalytic rate with minimum computational effort but simultaneously with sufficient accuracy to avoid missing any potential candidates.

In details, the Dijkstra's algorithm [27] was used to single out the shortest (minimum-barrier) path between initial and final states within the given reaction network, which gives the largest contribution to the rate constant under steady-state conditions. This path was then sectioned into a sequence of lowest-free-energy resting states and highest-free-energy transition states, in which the resting states are local minima of the free-energy profile while transition states are the highest-free-energy points between two resting states. The free-energy difference between each couple of transition and resting states defines our set of free-energy barriers, which are then arranged in decreasing order. It can be noted in this connection that, for the largest barrier, its resting state exhibits the most negative degree of rate control (DRC) index and its transition state exhibits the most positive DRC index as defined by Campbell et al. [38], but the second-largest and lower barriers typically exhibit negligible DRC indexes.

It is noted that the free-energy diagram and thus the associated hierarchy of reaction barriers depend also on the experimental conditions, i.e., temperature and pressure of reactants and products. Here T=673 K, P(H2)=15 atm, P(N2)=5 atm, and P(NH3)=1 atm were selected.

Accordingly, 4 distinct steps in the N2 reduction, three distinct steps in adding H* to NHx* and two distinct NH3 desorption steps were found. Based on the relative barriers the above steps were further reduced to two potential RDS for N2 desorption, one for H* plus NHx, and one NH3 desorption. This is especially important when optimization approaches the ideal catalyst presenting a uniform energy landscape, in which all the potentially rate-determining steps exhibit similar barriers and similar rates. Thus, screening methods of the disclosure (herein also HHTS) consider a diversity of energetic and barrier calculations. This makes HHTS much more likely to succeed for a much wider and rigorous applicability. The only assumption in HHTS is that the dopants can change the relative energies of the configurations and therefore the kinetics, but do not significantly change the overall reaction mechanism.

Example 8: Modify the Fe(111) Catalyst to Generate Candidate Catalysts

Fe(111) catalyst is used as the reference catalyst for modification to generate a number of candidate catalysts. To modify the Fe(111) catalyst, one of the 4 topmost Fe atoms in the (2×2) unit cell was replaced with one from a set of 34 metal elements covering a large portion of the periodic table (substitutional surface doping, see FIG. 7, panel A,B, with the set of dopants shown in FIG. 7, panel C). The 29 transition metal elements, plus selected lanthanides for a total of 34 elements were considered as dopants (alkalis such as K are not considered since they adopt non-substitutional configurations)

Example 9: Define a Criterion to Estimate the Effect of the Proposed Change in the Catalyst on Each Energy Barrier Each RDS is associated with an energy barrier. For each barrier a simple criterion was defined to estimate how the given barrier will be affected by a change in the catalyst.

Figure 8:
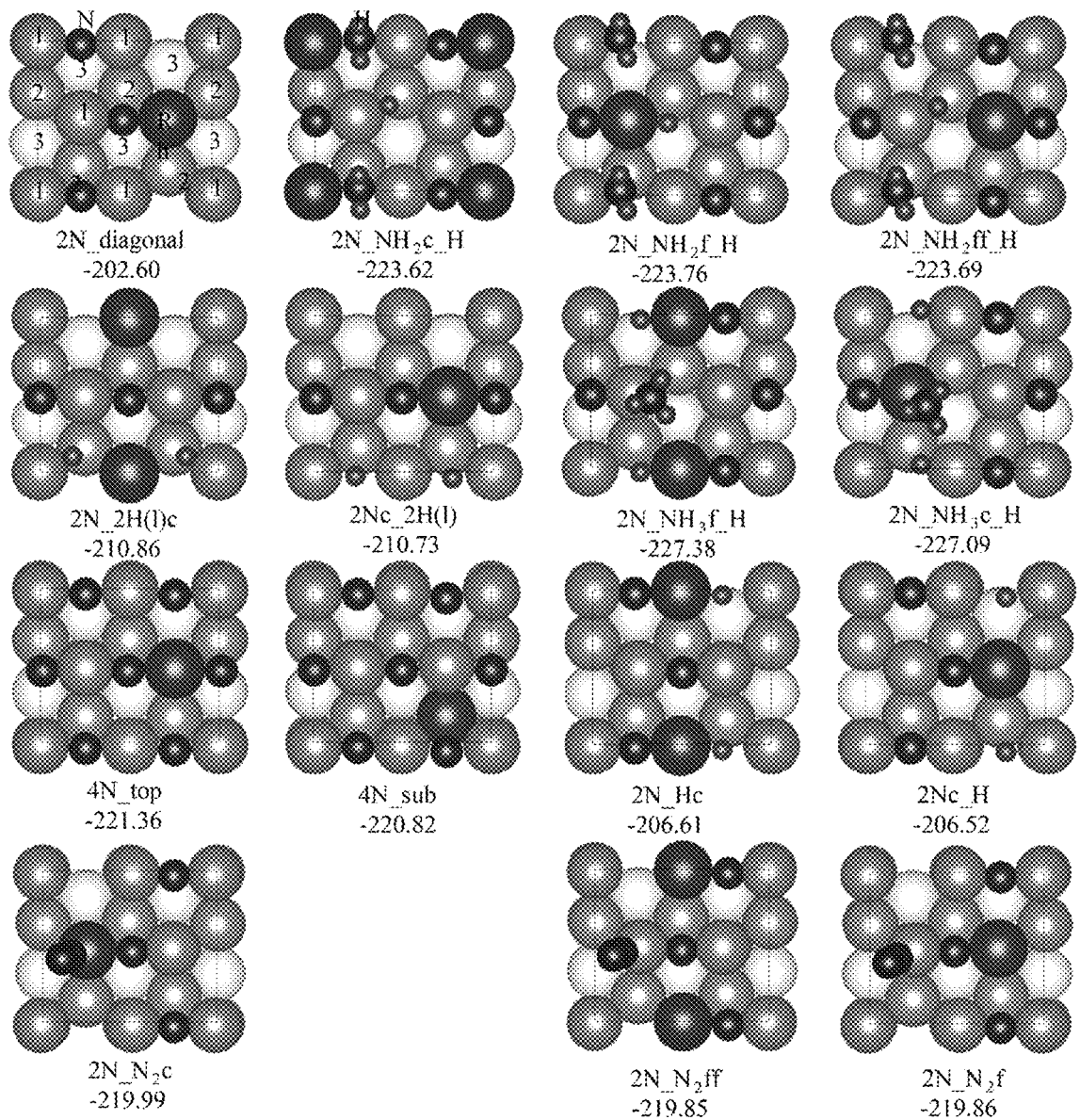
FIG. 8 illustrates in an exemplary embodiment schematic depictions of the configurations used for reaction energies (the numbers are electronic energies (eV) from DFT simulations) for estimating barriers (energies for Rh-doping case) [1]. The Rh, N and H atoms are represented by large, medium, and small balls, respectively. To represent the complexity of various doping sites, symbols are used here for adsorbed species different from FIGS. 6 and 9. The symbol (l) represents the linear 2N_2H[linear2] structure while the symbol c (or f) represents a doping element put close to (or far from) the N, H, $NH_2$ and $NH_3$ species.

This was done by associating a reaction to each barrier and using the corresponding electronic reaction energy (same DFT approach and VASP software as in Ref. [2]) to estimate the change in free-energy barrier. In other words, only the free-energy of reference states were explicitly calculated. In general, the free-energy of transition states can be explicitly calculated or estimated via Brønsted-Evans-Polanyi (BEP) relations [33, 34]. But the key barriers for $N^2$ adsorption and hydrogen migration are essentially constant (independent of the dopant), which corresponds to assuming unitary slope BEP linear relationship between free energy barrier and reaction free energies. In some cases, for example, for the predicted best dopant, Rh, the barriers were calculated. The good correspondence of this full predicted with the in-silico estimates justifies the approximation. Simple DFT geometry relaxations are needed to evaluate such criteria for each element. FIG. 8 illustrates the configurations used in the screening procedure.

Example 10: Evaluate Each Criterion in the Order of Decreasing Barrier

The previous QM studies for HB on Fe(111) found 4 reaction barriers: two are involved in adsorbing/dissociating N2, one is involved in Had reacting with NHx to form NHx+1, one is associated with H2 poisoning, and one involves NH3 adsorption/desorption. But in analyzing the rates using kMC these rates can be related back to fundamental differences in free energies of various intermediates which allows one to minimize the states that is analyzed.
Criterion 1. Triple Bonded N2 Absorption Over 2N State The largest free-energy barrier in the diagram of FIG. 6—yellow line, barrier (1)—is associated with N2 adsorption over the 2N state. The system first transforms from its low-energy resting state with a high coverage of NHy-absorbed species into the 2N[zig-zag] configuration (FIG. 8, A), which has two nearest-neighbor vacant bridge sites so that it can dissociate $N_2$, which is followed by $N_2$ adsorption and dissociation. It is noted[8] that the 2N[zig-zag] configuration is named "zig-zag" because an alternative "linear" configuration with the same stoichiometry exists, as illustrated in FIG. 11(a,b) (the same alternative applies to configurations with different stoichiometry such as 2N_NH$_2$_H, 2N_N$_2$[γ], etc.). A high energy price is associated with generating the 2N[zig-zag] configuration on Fe(111). An improved catalyst should decrease this energy price and thus the stability of N adatoms on the surface, while still exhibiting a sufficiently large affinity to nitrogen to be able to dissociate $N_2$ effectively. The first criterion is identified as being connected with the N2 adsorption/dissociation barrier, with the electronic reaction energy from the 2N_NH2_H[zig-zag] (FIG. 8, B-D) resting state to 2N[zig zag]; "2N_NH2_H[zig-zag]+NH3" (see FIG. 8 for pictorial illustrations). Note that the highest saddle point for subsequent $N_2$ dissociation is 0.3 eV below the saddle point corresponding to barrier(1). This might become rate determining when the $N_2$ absorption energy onto the catalyst surface is too small. The first criterion is thus complemented by evaluating the $N_2$ adsorption energy on 2N[zig-zag], i.e., the energy difference between the "2N[zig-zag]+N2gas-phase" and 2N_N2[γ,zig-zag] configurations, and ensuring that this adsorption energy is >0.5 eV as an additional constraint. Barrier(1) is estimated via the formulae:

$$\text{barrier}(1) = \Delta E\{2N\_NH2\_H[\text{zig-zag}] \to 2N[\text{zig-zag}] + NH3\} - 0.104 \text{ eV} \quad (1)$$

$$\text{constraint: } \Delta E\{2N\_N2[\gamma,\text{zig-zag}] \to 2N[\text{zig-zag}] + N2\} > 0.5 \text{ eV} \quad (2)$$

wherein 2N_NH2_H[zig-zag], 2N[zig-zag] and 2N_N2[γ, zig-zag] (FIG. 8, M-O) correspond to the surface configurations discussed above, $N_2$ and $NH_3$ refer to molecules in the gas phases, and "ΔE" refers to the electronic energy difference between the states after arrow and states before arrow. The energy value "0.104 eV" was computed based on the free energy corrections of the pure Fe(111) surface. The barrier (1) corresponds to the energy barrier (1) values in FIG. 6 for the pure Fe(111) surface. All the electronic energies of the doped configurations are listed in the

TABLE 4

Exemplary electronic energies of the doped configurations

| Element | 4N_subsurface | 4N_top_layer |
|---|---|---|
| Pd | −218.3993357 | −219.1870789 |
| Pt | −219.5902159 | −219.9878914 |
| Cu | −217.0311185 | −217.2738684 |
| Ni | −219.3320788 | −219.2568385 |
| Co | −220.98062 | −220.8070058 |
| Fe | −222.19011584 | −222.19011584 |
| Rh | −220.8212514 | −221.3573372 | barrier(1-4) = barrier(1-4) + max{ DE{4N[subsurface-dopant] → 4N[surface-dopant] }, 0} wherein Fe has the same electronic energy for top layer and subsurface layer.
Criterion 2. H2 Poisoning N2 Dissociation Via the 2N_2H Resting State The second highest barrier in FIG. 6—blue line, barrier (2)—is associated with the same saddle point, but is connected with the observation that the 2N_2H[linear] (FIG. 3 E-F) configuration can represent a resting state under some conditions (e.g. at low NH3 pressure) which can slow down catalysis (H2 poisoning). Therefore, the second criterion is expressed by the formula:

$$\text{barrier}(2) = \Delta E\{2N\_2H[\text{linear2}] - 2N[\text{zig-zag}] + H2\} + 0.113 \text{ eV} \quad (3)$$

where 2N_2H[linear2] corresponds to the surface configuration (FIG. 11) discussed above, and H2 refers to hydrogen in the gas phase. The energy value "0.113 eV" was computed based on the free energy corrections of the pure Fe(111) surface.
Criterion 3. $H_{ad}$ Migration to NH2Ad to Form NH3adx The conversion of adsorbed N into NHy species is also associated with high energy barriers, the third largest in the free-energy diagram of FIG. 6—green line, barrier(3)—, and our third criterion estimates these barriers. The highest-barrier hydrogenation (or hydrogen migration) mechanistic step was focused on, which is the hydrogenation of 2N_NH2_H: "2N_NH2_H->2N_NH3". The Brønsted-Evans-Polanyi principle was used assuming that the energy barrier of this step will be a linear function of the energy difference between 2N_NH2_H and 2N_NH3_H configurations (FIG. 8, G-H), thus estimating the third barrier with the formula:

$$\text{barrier}(3) = \Delta E\{2N\_NH2\_H[\text{zig-zag}] + \tfrac{1}{2}H2 \to 2N\_NH3\_H[\text{zig-zag}]\} + 1.549 \text{ eV} \quad (4)$$

where the 2N_NH3_H[zig-zag] corresponds to the surface configuration discussed above. The energy value "1.549 eV" was computed based on the free energy corrections of the pure Fe(111) surface.
Criterion 4. NH3 Desorption NH3 desorption can be rate-limiting—red line, barrier (4)—, so the fourth criterion ensures that a high NH3 desorption energy does not decrease in the overall rate. The largest NH3 desorption barrier is expected close to the 2N[zig-zag] state, for the 2N_NH3_H[zig-zag] configuration, and is estimated with respect to the 2N_NH2_H[zig-zag] resting state as follows:

$$\text{barrier}(4) = \Delta E\{2N\_NH2\_H[\text{zig-zag}] + \frac{1}{2} H2 \rightarrow 2N\_NH3\_H[\text{zig-zag}]\} + \Delta H\{2N\_NH3\_H[\text{zigzag}] \rightarrow 2N\_H[\text{zig-zag}] + NH3\} + 0.425 \text{ eV} \quad (5)$$

Criterion 5. Preference of Dopant in Top Layer Versus Second Layer

The above criteria assume that the overall free-energy diagram is only altered quantitatively, not qualitatively, by the proposed change in the catalyst. The fifth and last criterion tests that the catalyst change does not introduce qualitative alterations of the diagram, i.e., the insurgence of degradation mechanisms. Inverse segregation of the dopant element into the bulk is a common mechanism for dopants that reduces the interaction of the catalyst surface with NHy-adsorbed species [39]. This degradation mechanism was only evaluated for the 4N configuration (FIG. 8,I) and for the dopant going from the top surface layer into the subsurface layer (FIG. 8,J). The increase in the previous barriers was estimated as follows:

$$\text{barrier}(1\text{-}4) = \text{barrier}(1\text{-}4) + \max\{\Delta E\{4N[\text{subsurface-dopant}] \rightarrow 4N[\text{surface-dopant}]\}, 0\} \quad (6)$$

where 4N[subsurface-dopant] and 4N[surface-dopant] correspond to the configurations discussed above, "max" refers to the maximum between the two numbers in the bracket, and "barrier(1-4)" refers to the maximum barrier for steps 1 to 4.

Example 11: Application of Hierarchical in Silico Screening to 34 Dopants

Figure 7:
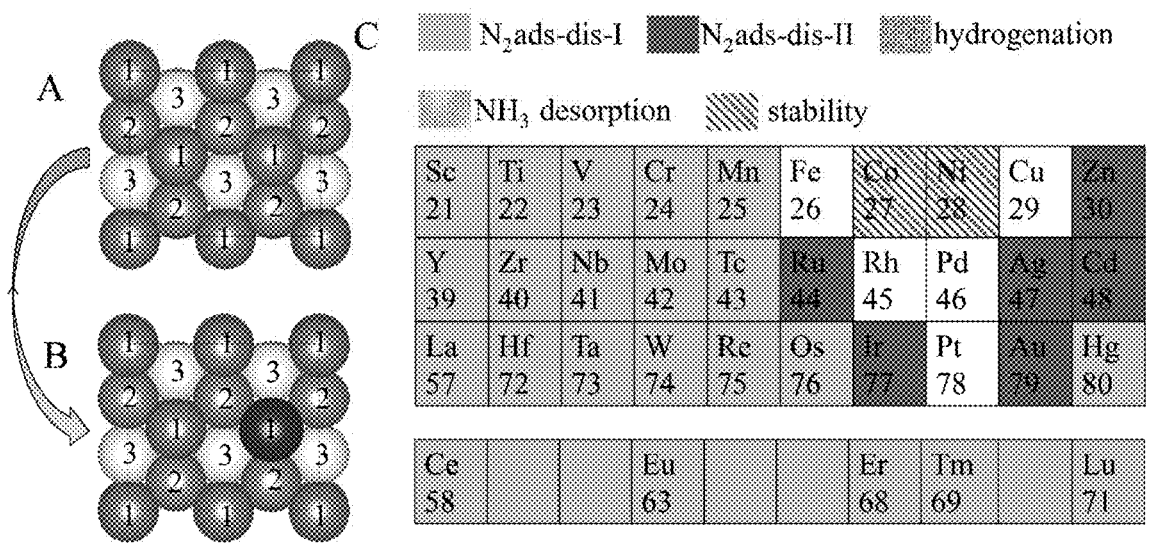
FIG. 7 illustrates schematic depictions of the (2×2) unit cell of Fe(111) both pure (panel A) and with one substitutional dopant (panel B) [1]. The top, $2^{nd}$ and $3^{rd}$ layers are marked with 1, 2, and 3, respectively. In (B) one dopant atom (dark large ball) replaces one topmost Fe atom. (C) Portion of the periodic table selected for catalyst screening (34 elements). In the top row the screening criteria are indicated in colors and textures, and the elements are also highlighted using the color and texture of the criterion which has sifted them out.
Figure 10:
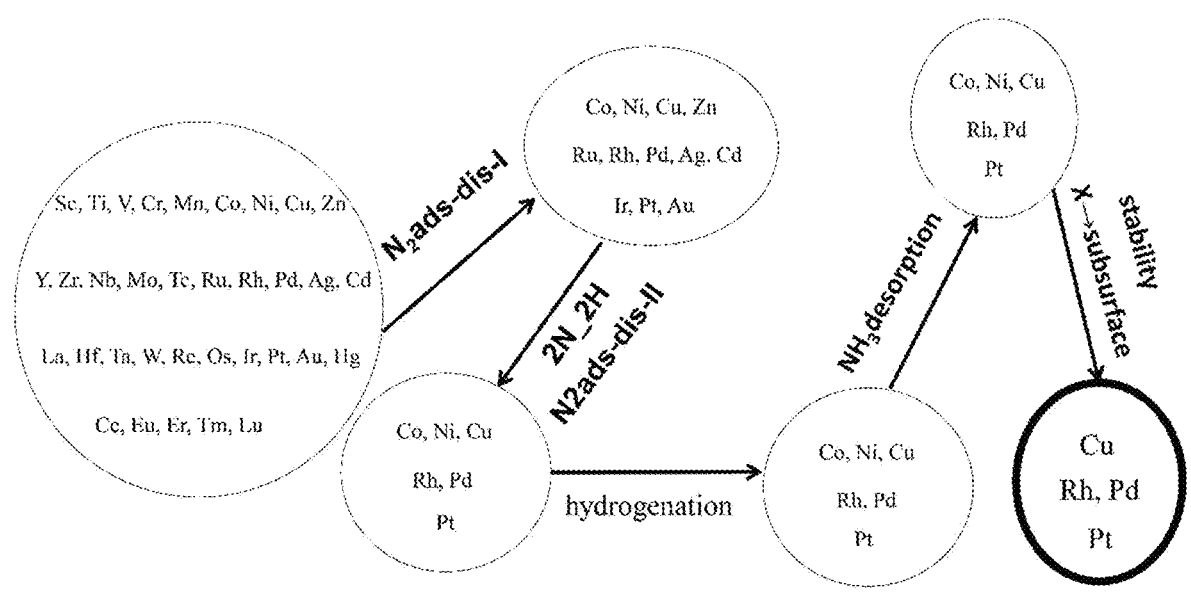
FIG. 10 shows an alternative illustration of the screening protocol as applied to ammonia synthesis over a singly, surface-substitutionally doped Fe(11) surface [1].

The application of the rapid in silico screening to HB over singly-top-surface-substitutionally-doped Fe(111) is illustrated in FIGS. 7 and 10 using the original free energy diagram.8 The electronic energy results of the five criteria are listed in Table 5 (with a complete report in Table 4).

Table 5 lists barriers of rate-determining steps in ammonia synthesis over pure and doped Fe(111) surface estimated via the Brønsted-Evans-Polanyi (BEP) principle as discussed in the text. Barrier-5 corresponds to the maximum of barrier (1-4) plus the stability penalty term. Rightmost column is the expected NH3 production rate per (2×2) unit cell per second. Free energies in eV.

Criterion 1. N2 Desorption/Dissociation

Of the 34 dopants, only 12 led to a barrier lower than the 1.68 eV for Fe, but an additional 3 that were only a little above 1.68 were kept, as shown in Table 5. The other 19 cases were not examined further. Of these 19, 14 are more electropositive than Fe (electronegativity ($\chi$)=1.8), while Mo is the same and Tc, Re, and Hg (all $\chi$=1.9) are only slightly more electronegative. This indicates that alloying a more electronegative element helps with N2 dissociation. Thus the elimination of Os ($\chi$=2.2) is the only outlier. It is interesting that Haber found that pure Os does do NH3 synthesis. Of these 12 selected dopants, none violate the constraint equation (2). It is noted that the best two, Rh and Pd, with a barrier lower by 0.17 eV might lead to a rate increase by a factor of 18.75 for our target conditions.

Criterion 2. H2 Poisoning to the N2 Adsorption

Here 6 more are eliminated. This includes the 4 closed shell elements (Cd, Au, Ag, and Zn). This suggests that open-shell d-electrons are preferred for good N2 dissociation barriers. It is not obvious why Ir and Ru have a high barrier. It is interesting that pure Ru (hcp crystal structure) does do NH3 synthesis.

Criterion 3. NHx Hydrogenation

All 6 remaining candidates are better than Fe.

Criterion 4. NH3 Desorption

All 6 remaining candidates are better than Fe. It is worth noting that criterion NH3 desorption becomes an important step for some (e.g. Pt-) doped systems. Note that these steps would not be considered within a DRC approach because of their low DRC indexes on the undoped catalyst.

Criterion 5. Surface Stability

Here two cases: Co and Ni, prefer subsurface. This may be because they are slightly smaller than Fe.

Selected Candidate Catalysts

Four catalysts are left: Rh and Pt predicted to be 4 times better than pure Fe and Pd and Cu predicted to be 2 times better than pure Fe.

Rh and Pt lead to a reduction in the overall barrier of 0.06 eV: hydrogen poisoning limits the potential reduction of 0.17 or 0.13 eV according to criterion (1). Reducing the overall barrier by 0.06 eV would not allow dramatically less extreme industrial conditions, but—if realized—should guarantee a reduction by a factor of ~4 in the energy consumption even maintaining the same conditions (≈200 atm total pressure and 773-823 K temperature) and indus-

| Element | barrier-1 | barrier-2 | barrier-3 | barrier-4 | barrier-5 | Rate($S^{-1}$, K) 673 |
|---|---|---|---|---|---|---|
| Rh | 1.51 | 1.60 | 1.31 | 1.44 | 1.60 | 14.61 |
| Pd | 1.51 | 1.63 | 1.42 | 1.51 | 1.63 | 8.71 |
| Pt | 1.55 | 1.59 | 1.36 | 1.60 | 1.60 | 14.61 |
| Cd | 1.55 | 1.84 | | | | |
| An | 1.57 | 1.82 | | | | |
| Co | 1.58 | 1.51 | 1.42 | 1.45 | 1.76 | |
| Ag | 1.59 | 1.81 | | | | |
| Ni | 1.60 | 1.39 | 1.48 | 1.53 | 1.68 | |
| Cu | 1.64 | 1.61 | 1.56 | 1.52 | 1.64 | 7.33 |
| Zn | 1.64 | 1.79 | | | | |
| Ir | 1.65 | 1.88 | | | | |
| Rn | 1.67 | 1.76 | | | | |
| Fe | 1.68 | 1.57 | 1.53 | 1.43 | 1.68 | 3.68 |
| Os | 1.73 | | | | | |
| Mn | 1.73 | | | | | |
| Ce | 1.74 | | | | | | trial plants as used presently. Further improvements can likely be achieved by implementing multiple doping strategies. The HHTS-estimated NH3 production rates for optimal dopants are also listed in Table 5.

Figure 12:
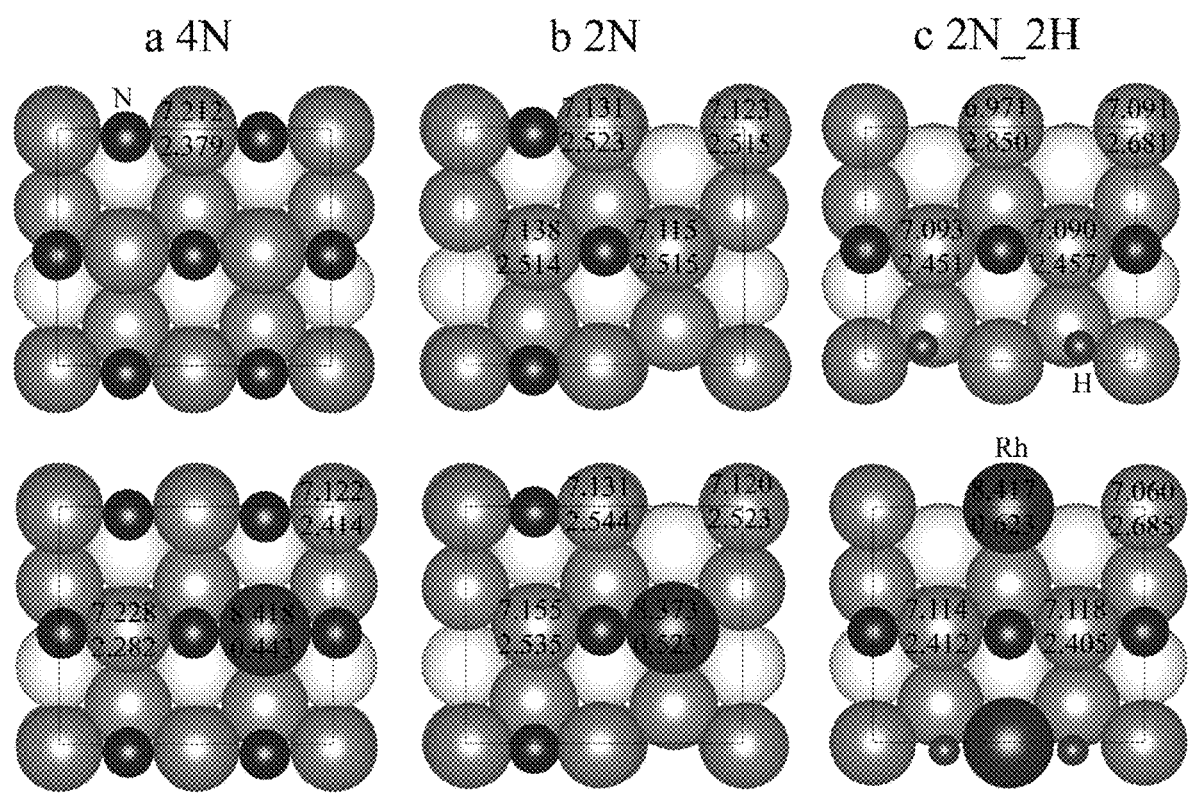
FIG. 12 illustrates the analysis of atomic charges and spins for selected configurations [1]. On top of surface atoms, the above number (bold face) and the bottom number (italics) are the charge and magnetic moment (in μB), respectively. The atom of Fe layer is the same as FIG. 8.

As discussed in Ref. [8], the barriers associated with these phenomena are also intimately related to the charge and magnetic state of surface atoms, as confirmed by an analysis of the changes in charges and spins of surface atoms upon doping, illustrated in FIG. 12.

Example 12: Full QM Analysis and Kinetic Study of Rh-Doping

Figure 13:
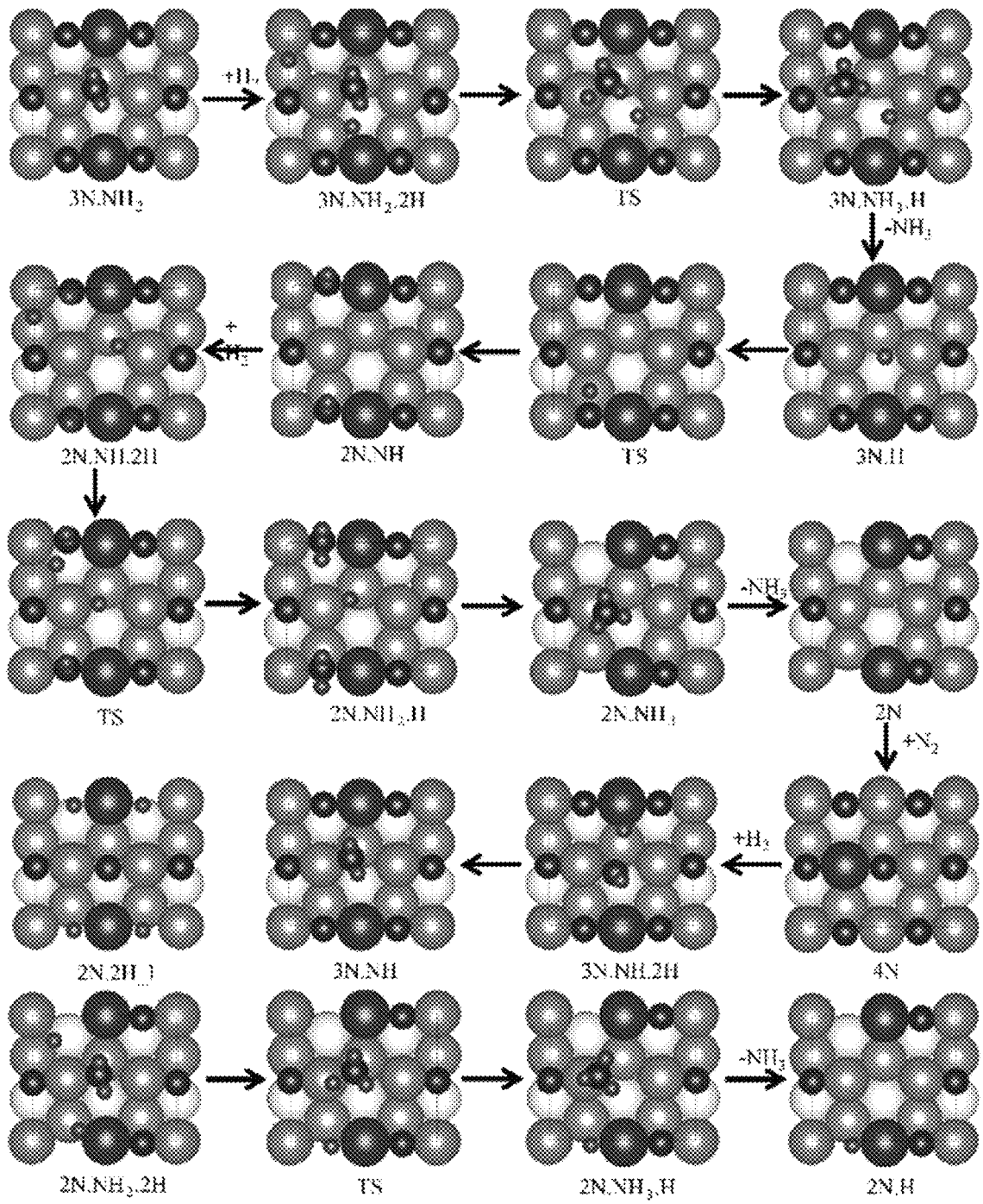
FIG. 13 illustrates in one embodiment the surface structure for reaction steps in FIG. 9. Every intermediate and transition state (TS) structure is geometrically optimized (or constrained optimized for TS with the results summarized to illustrate the adsorption sites for various species, and interaction between these adsorbed species. Only 4 TS structures with the highest free energy barriers are shown. The Rh, N and H atoms are represented by large, medium, and small balls, respectively. The atom of Fe layer is the same as shown in FIG. 8.
Figure 14:
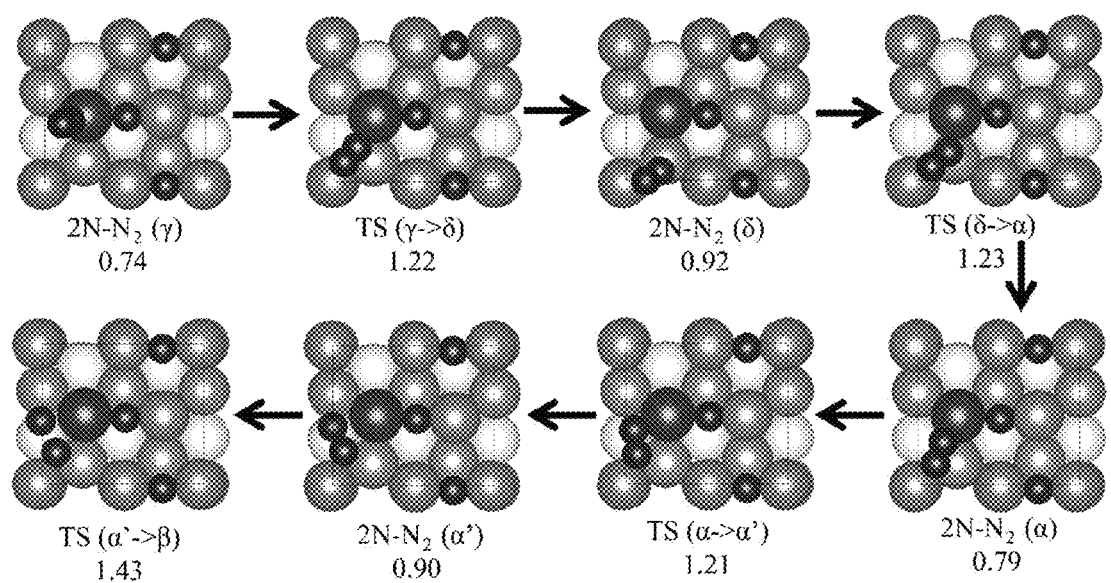
FIG. 14 illustrates in one embodiment the $N_2$ dissociation steps on Rh-doped Fe(111) surface [1]. The free energy (in eV) are listed below the status, and evaluated at 673 K, $P(H_2)$=15 atm, $P(N_2)$=5 atm, $P(NH_3)$=1.0 atm. The Rh and N are represented by large and medium balls, respectively. The atom of Fe layer is the same as FIG. 8.

The above in silico analysis focused on 11 key states that determine the major barriers. This allowed us to reduce the candidates from 34 to 4. Now the full analysis will be considered for one of the winners, Rh, which is estimated as being 4 times better than Fe. To this end the study is extended from the 11 configurations considered above and consider the 21 configurations and 13 barriers most important for the kinetics (FIGS. 13-14).

QM simulations were performed on a (2×2) unit cell of the Fe(111) surface substitutionally doped in the top layer with one Rh atom and reconstructed a substantial portion of the reaction energy diagram, as shown in FIG. 9. A simplified reaction pathway is illustrated pictorially in FIG. 13 showing the surface structure step by step, to clarify the nature of each adsorption site and the interactions between these adsorbed species. The favorable mechanistic paths are the same as on the pure Fe surface.8 FIG. 9 plots a standard state free energy diagram which does not include the configurational entropy of adsorbates. However, configurational effects are taken into account in our kMC simulations model by including the configuration counting into the rate constants.

To validate our assumptions, the 4 key reaction steps used in the HHTS approach were compared between pure Fe and Rh-doped catalysts. For the pure Fe catalyst, the free energy barriers for N2 adsorption (step1), H2-poisoning (step2), H migration (step3), and NH3 desorption (step4) are 1.68, 1.57, 1.52, and 1.43 eV, respectively. Based on our assumptions, the estimated barriers from HHTS for Rh-based catalyst are 1.51, 1.60, 1.31 and 1.44 eV for these 4 steps, respectively, whereas explicit calculations on the Rh-doped catalyst give values of: 1.44, 1.62, 1.31 and 1.35 eV, respectively. The difference between estimated and explicit calculations is within a maximum error of 0.09 eV, thus validating our free-energy barrier estimates.

The energetics from the free-energy diagrams of FIGS. 6 and 9 were used as input to kinetic Monte Carlo (kMC) simulations, using the same set of 21 configurations and 13 barriers for both pure and Rh-doped Fe(111).

On pure Fe(111), this leads to production of 2441 NH3 molecules produced by our (2×2) unit cell, corresponding to a predicted TOF=4.6 NH3/sec per (2×2) site, which can be compared to TOF=3.68 for our simplified model.

On Rh-doped Fe(111), this leads to production of 35980 NH3 molecules produced by our (2×2) unit cell, corresponding to a predicted TOF=9.7 NH3/sec per (2×2) site, which can be compared to 14.6 in our simplified model.

However, the Rh-doped system can be further improved by exploiting its sensitivity to H2 poisoning and working in a lean-H2 régime. Thus reducing the H2 pressure from 15 to 6.5 atm: under conditions of T=673 K, P(H2)=6.5 atm, P(N2)=5 atm, and P(NH3)=1 atm, it is predicted TOF=15.3 NH3/sec per (2×2) site, which is a factor of 3.3 larger than on Fe(111), in good agreement with expectations from the HHTS estimates. Thus it is estimated that Rh doped Fe might lead to an overall TOF that is ~3.3 times the current Fe based catalysts. Note that reducing H2 pressure slows down the reaction rate for Fe, but increases it for Rh. Given the high cost of H2, working under lean-H2 conditions may be beneficial in terms of production costs.

Finally, to provide information on mechanistic details, the steady-state apparent ΔG (i.e., the logarithm of the relative populations or residence times) for the most important states are reported in FIG. 17 for both pure and doped Fe(111).

Example 13: Modifications of the PBE-D3(BJ) Free-Energy Diagram

Figure 15:
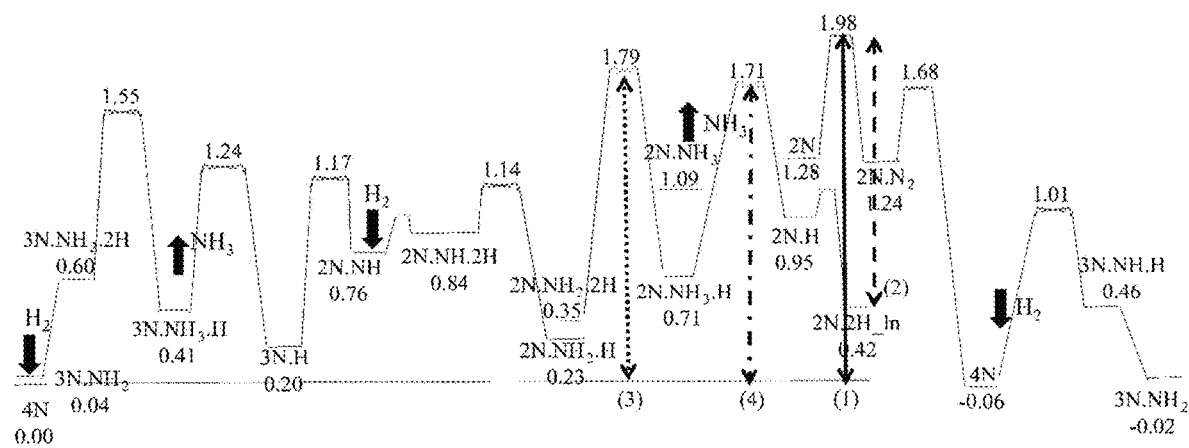
FIG. 15 illustrates in one embodiment the DFT/PBE-D3 free energy diagram for ammonia synthesis over a (2×2) unit cell of the Fe(111) surface, modified by including semi-empirical corrections as described in the detailed description, and evaluated at 673 K, $P(H_2)$=15 atm, $P(N_2)$=5 atm, $P(NH_3)$=1.0 atm [1]. As in FIG. 6, the barriers selected for high-throughput screening are represented by various vertical lines. Free energies in eV.

Any HTS approach depends on the accuracy of the assumed free-energy diagram. The one employed here was derived using the DFT/PBE-D3 method,8 and leads to excellent agreement with experimental ammonia production rates at low NH3 pressure [40](theory: 17.7/sec for a 2×2 surface cell; experiment 9.7). In this example, experiments were performed to test how robust our analysis is with respect to a change in the system energetics. In particular, one issue of FIG. 6 is that the overall free-energy change (δG) ammonia synthesis reaction [N2+3 H2->2 NH3] is predicted by PBE-D3(BJ) to be −0.54 eV at 673° K, and 5:15:1 atm of N2, H2 and NH3, respectively. In contrast the experimental value is δG=−0.06 eV under the same conditions.[27] To test how sensitive the HHTS predictions are to this issue, an empirical correction [28]is used and the free-energy diagram of FIG. 6 is modified by adding a quantity of [0.08·y] eV to the free energy of NHy surface species. This corresponds to assuming that PBE-D3(BJ) overestimates the N—H vs. N—Fe bond strength by this quantity (for transition states corresponding to hydrogenation mechanisms half of the 0.08 eV correction is used). The overall gas-phase energetics of the HB reaction is so recovered by distributing the PBE-D3(BJ) error in δG uniformly over the energetics of surface species. The free-energy diagram resulting after applying these corrections is reported in FIG. 15, under the same conditions of FIG. 6: T=673 K, P(H2)=15 atm, P(N2)=5 atm, P(NH3)=1 atm (thermodynamic equilibrium conversion using experimental energetics corresponds to 1.7 atm NH3 pressure, thus P(NH3)=1 atm is consistent with roughly 50% conversion typically used in the industrial HB process). The five basic criteria described in the proceeding examples need to be only slightly modified after applying these corrections (the main difference being that the resting state of the system is now the 4N configuration), and are detailed in the Example 2.

The high-throughput screening protocol was applied using these new criteria. Interestingly, the 5 elements (Rh, Pt, Cu, Pd, with the addition of Ni which is roughly identical to Fe) which are suggested as promising using the free-energy diagram of FIG. 6 are still present in the final HHTS set derived using the diagram of FIG. 15, as illustrated in FIG. 16. The major difference is that:

(1) the NH3 production rate at P(NH3)=1 atm by the Fe(111) surface is decreased (the production rate at low NH3 pressure using FIG. 15 does not change much and is also consistent with the experiment23), (2) therefore, the expected acceleration due to doping is increased, and (3) more elements are included in the set of potentially promising dopants, such as Zn, Ag, Au, Cd. In particular Zn seems particularly appealing due to its small size mismatch with Fe.

Apart from calling for a proper experimental validation of the accuracy of DFT for this system, these finding suggests that, overall, the set of optimal dopants determined in FIG. 7 is reasonably robust to a change in the theoretical method. Much larger enhancements in production rates are predicted when using the free energy diagram of FIG. 15. The expected maximum in catalytic activity is realized for Cu, Ni, and Pd, with a reduction in overall barrier amounting to 0.35-0.37 eV, thus translating into a potential speed-up by more than factor of 100 in HB process rate.

In view of the above, it is noted, clearly, several variants of HHTS can be conceived. For example, the kinetic model can be analyzed and solved via other methods not considered in this work, such as micro-kinetic modeling as in the DRC approach [38]. In this connection, note that, to implement our hierarchical approach, DRC indexes could be defined for each section of the free-energy diagram potentially leading to rate-determining steps. The screening criteria can be improved by explicit transition state calculations. The free-energy diagram can be made more accurate, e.g., by improving over the harmonic approximation to evaluate entropic contributions, using more accurate exchange-correlation functionals or higher-level computational methods, or adjusting empirical corrections to the energetics of different metals. Other strategies for changing the catalyst such as multiple (ternary, etc.) doping can be investigated. Finally, catalytic selectivity rather than simple activity can be targeted for optimization.

Example 14: Performing Stability Test to Select Catalysts Having a Stable Configuration The stability of Si dopant on Fe(111) subsurface was computed. The 4N configurations were used in the stability calculation since it is the most stable configuration. The electronic energy of following configurations were computed: (1) Si doped on subsurface (E_sisub); (2) Si doped on top surface (E_sitop); (3) Si doped on third layer (E_Si3rd); and (4) undoped Fe(111)+$SiH_4$ (This illustrate possible vaporization reactions of 4N(Si-sub)+Fe(bulk)+$2H_2$->4N (undoped)+$SiH_4$). The calculation indicated that the subsurface configuration is the most stable configuration (1.15 eV, 0.60 eV and 2.73 eV lower in energy than (2), (3) and (4)). Thus, the Si dopant passes the stability criterion.

Example 15: Hierarchical Screening of Target Properties for Exemplary Multicomponent Iron Catalyst for Ammonia Synthesis Activity, stability and selectivity target properties of catalyst of Haber-Bosch ammonia synthesis have been evaluated to determine preferred hierarchical screening of these properties with screening method of the disclosure.

For the Haber-Bosch ammonia synthesis, selectivity of a catalyst is not an important factor since NH3 is the most likely product from reducing N2 with H2, while stability of the catalyst is an important property of since the catalyst might decompose or be poisoned by many side reactions and activity is paramount since the Fe catalyst forces performing the reaction at extreme conditions of pressure (200 atm) and temperature (500 C) as will be understood by a skilled person Additionally, with respect to stability for many additives of iron catalyst of the Haber-Bosch ammonia synthesis there is a strong preference to be at the surface layers while other additives prefer the second layer and others prefer the third layer over going deeper in the catalyst particle. Generally such data is not available from experiment, so this aspect of stability has not previously been a component of catalyst design.

Accordingly for catalyst of the Haber-Bosch ammonia synthesis, stability and selectivity are expected to require screening of a high number of candidate catalysts to identify rate-selected catalyst having an enhanced reaction rate with respect to a reference iron catalyst, are expected to be computationally costly, while screening of selectivity can be omitted.

Therefore screening for catalyst of the Haber-Bosch ammonia synthesis is performed with screening method for activity and stability of the present disclosure, and catalyst identified according to the approach outlined in Example 17.

Example 16: Hierarchical Screening for Activity of a Plurality of Candidate Exemplary Multicomponent Iron Catalysts for Ammonia Synthesis Hierarchical screening of a plurality of candidate catalysts multicomponent iron catalysts for Haber-Bosch ammonia synthesis has been performed in accordance with screening method for hierarchical screening of activity and stability of the disclosure.

In particular, a plurality of candidate catalysts comprising a large set (34) of dopants that are expected to affect the rates of Haber Bosch ammonia synthesis with respect to the pure Fe catalyst were simulated. More particularly, considering just single dopants the screening methods herein described have selected catalysts with additional small amounts of Rh or Pt that can dramatically favor the top surface and can increase the rate by a factor of 3. More impressive is the identification of rate selected catalysts supporting the conclusion that addition small amounts of Ni that dramatically favor the second layer can increase the rate by a factor of 16 while small amount of Si that also dramatically favors the second layer can increase the rate by a factor of 32. Such dramatic increases in rates for rate-selected iron catalysts for Haber Bosch ammonia synthesis according to screening method of the disclosure is expected to enable much lower pressures and temperatures while retaining the same overall rates. Such a change in reaction conditions is expected to dramatically lower the costs of manufacturing plants from billions of US dollars to modest levels that would allow the production of NH3 to be carried out small production sites to be located globally where the NH3 can be converted to fertilizer.

In outcome of the exemplary screening of iron catalyst for Haber Bosch ammonia synthesis performed herewith four most preferred dopants Rh, Pt, Pd and Cu for the first layer, and four most preferred dopants Ni, Co, Cr, and Si, in the second layer have been identified Candidate catalysts comprising these most preferred dopants are expected to be capable according to the simulation of significantly accelerating Haber Bosch rates with respect to the pure Fe catalyst. Additionally in view of performance of stability test driven by thermodynamics, it is expected these surface concentrations to be maintained during the reactions by using the proper concentrations that maintain low levels in the bulk that can re-equilibrate with the surface concentrations as surface species evaporate or become oxidized. <

Example 17: Hierarchical Screening of Target Properties for Exemplary Multicomponent Cu Catalyst for Electrocatalysis of CO Although not as important for NH3 synthesis, (see Example 15) selectivity is a key issue for other catalysts such as the VPO butane to maleic anhydride catalyst or the propane and propene ammoxidation catalysts with high selectivity are paramount.

A good example for comparison referred herein is the electrocatalysis of CO shown in FIG. 7. The common intermediate for forming C2H4 and C2H5OH is HOCCH*. Since the free energy barrier for going to the C2H4 branch is 0.61 eV while the free energy barrier for going to the C2H5OH branch is 0.67 eV it is expected that at 298K there will be 11 times more C2H4 produced than C2H5OH. The experiments find 14 times higher rate for C2H4, indicating that the difference in barriers is 0.066 not 0.06 eV. This is sufficiently accurate to be used to examine ways to change this ratio from 14:1 to 1:14 by alloying with additives, surface modifications, electrolyte modifications, and additional modifications identifiable by a skilled person.

Indeed experiments and theory show that on Cu NP, this preference is completely flipped, with C2H5OH formation ~10 times that of C2H4. The changes identified in the catalyst surface responsible for this has been determined by combining QM and ReaxFF methods with machine learning. [41]

Therefore, HHTS screening methods of the disclosure for screening can be used for optimization of electrocatalysts for activity and selectivity in CO2 and CO reduction to specific desired products. Here again a mix of QM and. QM trained ReaxFF reactive MD enables a further screening of the stability as will be understood by a skilled person upon reading of the present disclosure.

Example 18: Preparation of Multicomponent Iron Catalyst for Ammonia Synthesis In industrial practice the multicomponent iron catalyst after optimization with HHTS will probably be prepared as bulk homogeneous alloys $Fe^b_{(1-xb)}A^b_{q_A}B^b_{q_B}C^b_{q_C}\ldots$ where $0<x_b<1$ and $x_b=Sum(q^b_A\, q^b_B$ and $q^b_C\ldots; 1=M)$. Here the values of $x_i$ for the bulk alloy have been calculated from the theory based on the predicted free energy of binding to each of the top 3 layers versus the predicted bulk solubility so that the surface concentrations match an initial design. Annealing at appropriate conditions is expected to lead to the target surface concentrations, which can be checked by Auger. XPS and other surface science tools for optimization preparation conditions. However laboratory experimental validation can use atomic layer deposition (ALD) where specific fractions of a monolayer are laid down sequentially on a support by ion sputtering, controlled surface reactions (CSR), cluster beam deposition, colloidal synthesis, or galvanic displacement as well as additional techniques for synthesizing metallic catalysts identifiable by a skilled person.

Typically to incorporate additives into the Fe catalyst for NH3 synthesis at the designed surface concentration one might mix the appropriate amounts based on the calculated free energies, and then heat to appropriate temperatures for appropriate times in appropriate environments to distribute the additives over the catalyst particles and deposit on an appropriate support.

Since the screening methods of the disclosure selects additives that prefer to segregate to the $1^{st}$, $2^{nd}$ or $3^{rd}$ layers with predominantly in a single surface layer in view of the related affinity, it is expected that rather small amounts of the additives can be used in the synthesis of the catalyst for laboratory ALD testing and for practical industrially prepared catalysts, while one can rely on thermodynamics to partition a high fraction of the additive between the bulk and the surface layers.

However, in validating the optimum choices for the additives, Atomic Layer Deposition (ALD) is expected to be preferred for the laboratory validation.

For example, in the synthesis procedure of a catalyst of Formula (I) herein described an Fe film can be deposited on an appropriate support, such as Al2O3. Then thin layers of the additives can be sequentially deposited on the surface. Thus to make a catalyst that has 25% Rh in the top layer and 25% Ni in the $2^{nd}$ layer, it is expected to be possible to lay down first an amount corresponding to one monolayer that is 75% Fe and 25% Ni followed by an amount corresponding to one monolayer that is 75% Fe and 25% Rh. The resulting product will be annealed and then examined with surface science techniques to determine if the desired rations have been achieved.

Then catalysis of the ammonia synthesis can be performed at various conditions to validate the performance. These conditions will then be possibly modified to improve the overall performance of the catalyst.

After optimizing performance using ALD, faster more economical approaches are expected to be identifiable based on alloying of the metal particles that can be more appropriate for large scale industrial implementation.

Example 19: Preparation of Multicomponent Iron Catalyst by Hydrogen Reduction A multicomponent iron catalyst on a substrate can prepared by contacting iron on a substrate with a sufficient amount of at least one dopant oxide or dopant chloride to form a mixture. The mixture was heated at 400 to 450° C. under an atmosphere of hydrogen ($H_2$) to reduce the dopant oxide or dopant chloride to elemental dopant on the surface of the iron, thus obtaining a dopant coated iron on a substrate. (U.S. Pat. No. 3,770,658).

Example 20: Preparation of Multicomponent Iron Catalyst by Annealing

A dopant coated iron on a substrate can be annealed under vacuum or in an inner gas atmosphere including $N_2$, Ar, and He at a temperature ranging from 300° C. to 600° C. for a sufficient amount of time for a dopant to migrant to iron atom top layer, iron atom second layer, iron atom third layer of an iron crystal or iron film. The total concentration would be based on the predicted free energies of binding to the top 3 layers versus bulk.

The annealing process can be monitored upon completion in different modalities via AC-HR-TEM, e.g., ex-situ at constant time intervals until no changes in the particle structure is observed. ([42] [43].

Example 21: Characterization of Multicomponent Iron Catalyst

Typically the surface character and concentration of as prepared and annealed catalysts before and after use for catalysis, will be examined with Transmission Electron Microscopy (TEM), Scanning Transmission Electron Microscopy (STEM), X-ray Photoelectron Spectroscopy (XPS), Stron Anion Exchange (SAX), X-ray Diffraction (XRD), Auger electron spectroscopy and similar techniques routinely in preparation and testing. Information on the experimental structure of catalyst particles with a spatial resolution down to the atomic scale (Å or $10^{-10}$ m) and therefore to detect the structure and composition of the catalyst with its precise distribution of atoms can be achieved via aberration-corrected high-resolution transmission electron microscope (AC-HR-TEM). (Ling, T. et al., Icosahedral Face-Centered Cubic Fe Nanoparticles: Facile Synthesis and Characterization with Aberration-Corrected TEM, Nano Letters, Vol. 9, No. 4, 2009, 1572-1576). Multi-component systems can be imaged and characterized as well via AC-HR-TEM. [43]

Example 22: Synthesis of Ammonia Catalyzed by a Multicomponent Iron Catalyst of Formula (I)

Reaction of hydrogen and nitrogen to form ammonia catalyzed by a multicomponent iron catalyst is expected to be carried out in a reactor containing an exemplary catalyst of Formula (I) and was heated at a temperature of 50 to 650° C. as is illustrated in FIG. 5.

Hydrogen and nitrogen with the molar ratio near 3:1 (and examples where 1:1 gives faster rates) are expected to be combined and introduced to the reactor. For standard Fe based Haber-Bosch catalysts, the ammonia product is a poison so optimum throughput requires extraction of products along with some H2 and N2 as the reaction proceeds.

The unreacted hydrogen and nitrogen is expected to continuously recycled to the reactor for further reaction. The total yield of ammonia is expected to be at least 99.9 based on starting amount of hydrogen upon recycled reactions.

In summary provided herein are screening methods to select catalysts having a desired set of target properties from a reference catalyst, and catalysts so obtained, as well as related catalysts material, composition, methods and systems. In particular, computer-based screening methods of the disclosure comprise
- hierarchically screening the plurality of candidate catalysts for activity alone or in combination with stability and/or selectivity for a target chemical reaction under a target condition,
- the hierarchically screening performed with respect to a rate-limiting step of the target chemical reaction under the target reaction condition,
- to provide a selected active catalyst optionally stable and/or selective for the target chemical reaction, the selected active catalyst having a reaction rate under the target reaction conditions higher than the reaction rate of the reference catalyst.

Example 23: Derivation of a Free Energy Reaction Network

In describing the first step of hierarchical screnning method of the disclosure performed to identify the best single dopants for the top layer, $2^{nd}$ layer, and $3^{rd}$ layer, QM methods were used (primarily PBE-D3 flavor of DFT). Such calculations are at the practical limits of <300 atoms and <50 picoseconds of QM based MD. However it has been established that such approach is accurate to 0.05 eV, making this our preferred methodology.

Similarly QM methods are known to work out the mechanism for the butane to maleic anhydride VPO catalyst [13]. Also QM have been used to determine the mechanism for the M1 phase of the MoVNbTeOx catalyst to activate propane to propene [13].

However methods can be used for calculating rates on much larger systems (up to millions of atoms) using the ReaxFF reactive force field. [9] This allows using hierarchal methods herein described or larger systems, but with less accuracy than QM. For example for the V2O5 catalyst to convert propane into propene, the accuracy was 0.25 eV [13]. This is still adequate for understanding the mechanism and for catalyst optimization but with more uncertainty.

For example to understand why 10-20 nm nanoparticles (NP) of Cu with 200,000 atoms lead to very high selectivity for ethanol, the ReaxFF reactive force field was used to grow the NP, [41] but to predict reaction rates, surface clusters were used with ~100 atoms in QM reactions to predict the optimum catalyst structure responsible for the selective production of ethanol. [41] Here machine learning has been used to identify the structures of the optimum sites. [41]

For systems too large for QM ReaxFF was shown to be able to reliably distinguish the key reactions steps and catalysts sites. For example, for the M2 phase of the MoVNbTeOx ammoxidation catalyst ReaxFF was able to show that the Te=O surface sites are responsible for the activation of propene. [4] Reaction dynamics with ReaxFF can determine the full set of reaction kinetics for complex reactions. [4]

Thus, the methodology developed using screening method herein described is not limited to those small enough for QM. The approach in using ReaxFF for screening method herein described is that the enormous database of QM reaction free energies and activation barriers from the screening method of the disclosure performed on single additive, have been used to retrain the ReaxFF to predict these energies to 0.05 eV. This will use the machine learning tools described recently in [41]. Then ReaxFF will be used to predict single additive systems with sizes of 10,000 atoms or more that will allow us to refine the optimum surface concentrations (only 0, 0.25, or 0.5) with the small systems for QM.

Then for the multicomponent catalyst cells with ~50,000 atoms will be used for reactive molecular dynamics to optimize the surface concentrations in the top 3 layers to optimize activity, selectivity, and stability (forming gas phase products with the additives that evaporate or oxidize). This will be done first for the surfaces studied by QM (111, 210, 110, 100). But then the catalyst preparation will be simulated to be used in experiments (ALD, bulk annealing) allowing grain particles for more realistic simulations of the experimental systems. This can consider 10-20 nm nanoparticles (100,000's of atom). At this level good agreement with experiment is expected.

The examples set forth above are provided to give those of ordinary skill in the art a complete disclosure and description of how to make and use the embodiments of the screening method and related catalysts, materials, compositions, methods and systems of the disclosure, and are not intended to limit the scope of what the Applicants regard as their disclosure. Modifications of the above-described modes for carrying out the disclosure can be used by persons of skill in the art and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. An, Q., et al., *QM-mechanism-based hierarchical high-throughput in silico screening catalyst design for ammonia synthesis*. Journal of the American Chemical Society, 2018. 140(50): p. 17702-17710.
2. Qian, J., et al., *Reaction mechanism and kinetics for ammonia synthesis on the Fe (111) surface*. Journal of the American Chemical Society, 2018. 140(20): p. 6288-6297.
3. Lum, Y., et al., *Electrochemical CO reduction builds solvent water into oxygenate products*. Journal of the American Chemical Society, 2018. 140(30): p. 9337-9340.
4. Cheng, M.-J. and W. A. Goddard, *The Mechanism of Alkane Selective Oxidation by the M1 Phase of Mo—V—Nb—Te Mixed Metal Oxides: Suggestions for Improved Catalysts*. Topics in Catalysis, 2016. 59(17-18): p. 1506-1517.
5. Grasselli, R. K., *Ammoxidation of propylene and propane to acrylonitrile*. chapter 5 of RSC Nanoscience & Nanotechnology No. 19 Nanostructured Catalysts: Selective Oxidations Edited by Christian Hess and Robert Schloegl, in Royal Society of Chemistry 2011 Published by the Royal Society of Chemistry, 2011.
6. Xiao, H., T. Cheng, and W. A. Goddard III, *Atomistic mechanisms underlying selectivities in C1 and C2 products from electrochemical reduction of CO on Cu (111)*. Journal of the American Chemical Society, 2016. 139(1): p. 130-136.
7. Ertl, G., et al., *Handbook of heterogeneous catalysis Second, Completely Revised Edition, Enlarged*. 2008.
8. Kakaei, K., M. D. Esrafili, and A. Ehsani, *Graphene Surfaces: Particles and Catalysts*. Vol. 27. 2019: Academic Press.
9. Senftle, T. P., et al., *The ReaxFF reactive force-field: development, applications and future directions*. npj Computational Materials, 2016. 2: p. 15011.

10. Fuller, J., et al., *Reaction mechanism and kinetics for ammonia synthesis on the Fe (211) reconstructed surface.* Physical Chemistry Chemical Physics, 2019. 21: p. 11444-11454.
11. Goddard III, W. A., *Quantum mechanics based mechanisms for selective activation of hydrocarbons by mixed metal oxide heterogeneous catalysts—A tribute to Robert Grasselli.* Catalysis Today, 2019.
12. Chenoweth, K., et al., *Development and application of a ReaxFF reactive force field for oxidative dehydrogenation on vanadium oxide catalysts.* The Journal of Physical Chemistry C, 2008. 112(37): p. 14645-14654.
13. Cheng, M.-J. and W. A. Goddard III, *The critical role of phosphate in vanadium phosphate oxide for the catalytic activation and functionalization of n-butane to maleic anhydride.* Journal of the American Chemical Society, 2013. 135(12): p. 4600-4603.
14. Jang, Y. H. and W. A. Goddard, *Mechanism of selective oxidation and ammoxidation of propene on bismuth molybdates from DFT calculations on model clusters.* The Journal of Physical Chemistry B, 2002. 106(23): p. 5997-6013.
15. Wiki, *Ethylene oxide.* web.archive.org/web/20170314133026/https://en.wikipedia.org/wiki/Ethylene_oxide, 2017.
16. Wiki, *Steam reforming.* web.archive.org/web/20170412014610/https://en.wikipedia.org/wiki/Steam_reforming, 2017.
17. Mcdonald, M., et al., *Highly Efficient Ni-Doped Iron Catalyst for Ammonia Synthesis from QM-Based Hierarchical High Throughput Catalyst Screening.* The Journal of Physical Chemistry C, 2019. 123: p. 17375-17383
18. Qian, J., A. Fortunelli, and W. A. Goddard III, *Effect of Co doping on mechanism and kinetics of ammonia synthesis on Fe (111) surface.* Journal of Catalysis, 2019. 370: p. 364-371.
19. Perdew, J. P., K. Burke, and M. Ernzerhof, *Generalized gradient approximation made simple.* Physical review letters, 1996. 77(18): p. 3865-3868.
20. Perdew, J. P., K. Burke, and M. Ernzerhof, *Generalized gradient approximation made simple.* Physical review letters, 1997. 78: p. 1396-1396
21. Johnson, E. R. and A. D. Becke, *A post-Hartree-Fock model of intermolecular interactions: Inclusion of higher-order corrections.* The Journal of chemical physics, 2006. 124(17): p. 174104.
22. Grimme, S., et al., *A consistent and accurate ab initio parametrization of density functional dispersion correction (DFT-D) for the 94 elements H—Pu.* The Journal of chemical physics, 2010. 132(15): p. 154104.
23. Cheng, T., H. Xiao, and W. A. Goddard, *Full atomistic reaction mechanism with kinetics for CO reduction on Cu (100) from ab initio molecular dynamics free-energy calculations at 298 K.* Proceedings of the National Academy of Sciences, 2017. 114(8): p. 1795-1800.
24. Laio, A. and M. Parrinello, *Escaping free-energy minima.* Proceedings of the National Academy of Sciences, 2002. 99(20): p. 12562-12566.
25. Iannuzzi, M., A. Laio, and M. Parrinello, *Efficient exploration of reactive potential energy surfaces using Car-Parrinello molecular dynamics.* Physical Review Letters, 2003. 90(23): p. 238302.
26. Fleurat-Lessard, P. and T. Ziegler, *Tracing the minimum-energy path on the free-energy surface.* The Journal of chemical physics, 2005. 123(8): p. 084101.
27. Dijkstra, E. W., *A note on two problems in connexion with graphs.* Numerische mathematik, 1959. 1(1): p. 269-271.
28. al., L. H.e., *SPPARKS Kinetic Monte Carlo Simulator.* spparks.sandia.gov.
29. Hoffmann, M. J., kmos.mhoffman.github.io/kmos/.
30. Stamatakis, M., *Kinetic modelling of heterogeneous catalytic systems.* Journal of Physics: Condensed Matter, 2014. 27(1): p. 013001.
31. Hermes, E. D., A. N. Janes, and J. Schmidt, *Micki: A python-based object-oriented microkinetic modeling code.* The Journal of chemical physics, 2019. 151(1): p. 014112.
32. Martin, R. M. and R. M. Martin, *Electronic structure: basic theory and practical methods.* 2004: Cambridge university press.
33. Nørskov, J. K., et al., *Towards the computational design of solid catalysts.* Nature chemistry, 2009. 1(1): p. 37-46.
34. Jacobsen, C. J., et al., *Catalyst design by interpolation in the periodic table: bimetallic ammonia synthesis catalysts.* Journal of the American Chemical Society, 2001. 123(34): p. 8404-8405.
35. Kittel, C., *Introduction to solid state physics*, John Wiley & Sons. Inc., New York, 2005.
36. Nalwa, H. S., *Handbook of thin film materials.* 2002: Academic Press.
37. Wiki, *Atomic radius* web.archive.org/web/20190331021653/https://en.wikipedia.org/wiki/Atomic_radius 2019.
38. Wolcott, C. A., et al., *Degree of rate control approach to computational catalyst screening.* Journal of catalysis, 2015. 330: p. 197-207.
39. Mortensen, J. J., et al., *Nitrogen adsorption and dissociation on Fe (111).* Journal of Catalysis, 1999. 182(2): p. 479-488.
40. Somorjai, G. A. and N. Materer, *Surface structures in ammonia synthesis.* Topics in Catalysis, 1994. 1(3-4): p. 215-231.
41. Huang, Y., et al., *Identification of the Selective Sites for Electrochemical Reduction of CO to C2+ Products on Copper Nanoparticles by Combining Reactive Force Fields, Density Functional Theory, and Machine Learning.* ACS Energy Letters, 2018. 3(12): p. 2983-2988.
42. Ling, T., et al., *Icosahedral face-centered cubic Fe nanoparticles: facile synthesis and characterization with aberration-corrected TEM.* Nano letters, 2009. 9(4): p. 1572-1576.
43. Piccolo, L., et al., *Understanding and controlling the structure and segregation behaviour of AuRh nanocatalysts.* Scientific reports, 2016. 6: p. 35226.

The invention claimed is:

1. A multicomponent iron catalyst for synthesis of ammonia from $N_2$ and $H_2$ comprising a three-layer structure having a Formula (I)

$$[Fe^0_{(1-x0)}Q^0_{x0}][Fe^1_{(1-x1)}Q^1_{x1}]_a[Fe^2_{(1-x2)}Q^2_{x2}]_b \qquad (I)$$

in which $Fe^0$, $Fe^1$, and $Fe^2$ represent iron atom on a first layer, iron atom on a second layer, and iron atom on a third layer of an iron crystal or iron film, respectively;

$Q^0$, $Q^1$, and $Q^2$ represent at least one dopant atom on the first layer, at least one dopant atom on the second layer, and at least one dopant atom on the third layer of the iron crystal or iron film, respectively, x0, x1, and x2 represent an atom percentage of the at least one dopant on the first layer, an atom percentage of the at least one dopant on the second layer, and an atom percentage of the at least one dopant on the third layer of an Iron crystal or iron film, respectively, and (1−x0), (1−x1), and (1−x2) represent an atom percentage of the iron atom on the first layer, an atom percentage of the iron atom on the second layer, and an atom percentage concentration of the iron atom on the third layer of an iron crystal or iron film, respectively; and a, and b respectively represent a ratio of total atoms on second layer, and a ratio of total atoms on third layer relative to a number of total atoms on first layer of an iron crystal or iron film, respectively and wherein $Q^0$ is selected from the group consisting of Cu, Zn, Rh, Pd, Ag, Cd, Au, or any combination thereof, wherein each dopant on the top layer is present in a corresponding atom percentage $q^0_{Cu}$, $q^0_{Zn}$, $q^0_{Rh}$, $q^0_{Pd}$, $q^0_{Ag}$, $q^0_{Cd}$, and $q^0_{Au}$;

$Q^1$ is selected from the group consisting of Cr, Co, Ni, Si, or any combination thereof, wherein each dopant on the second layer is present in a corresponding atom percentage $q^1_{Cr}$, $q^1_{Co}$, $q^1_{Ni}$ and $q^1_{Si}$;

$Q^2$ is selected from the group consisting of Ga or any combination thereof, wherein each dopant on the third layer is present in a corresponding atom percentage $q^2_{Ir}$, and $q^2_{Ga}$;

wherein x0 is the summation of $q^0_{Cu}$, $q^0_{Zn}$, $q^0_{Rh}$, $q^0_{Pd}$, $q^0_{Cd}$ and $q^0_{Au}$;

x1 is the summation of $q^1_{Cr}$, $q^1_{Co}$, $q^1_{Ni}$ and $q^1_{Si}$; and x2 is the summation of $q^2_{Ir}$, and $q^2_{Ga}$; and and wherein x0, x1, and x2 each range independently from 0.2 to 0.4, with the proviso that x0+x1+x2 ranges from 0.2 to 1.2; and a and b independently range from 0.5 to 2.

2. The multicomponent iron catalyst of claim 1, wherein each of the first layer, the second layer, and the third layer are an iron film or crystal.

3. The multicomponent iron catalyst of claim 2, wherein the iron crystal has a body-centered-cubic crystal lattice.

4. The multicomponent iron catalyst of claim 1, wherein each of the first layer, the second layer, and the third layer are on Fe(111) face, Fe(211) face, Fe(110) face, Fe(100) face.

5. The multicomponent iron catalyst of claim 1, wherein $Q^0$ is Zn, and $Q^1$ is selected from the group consisting of Ni, Co, and Si, or any combination thereof, wherein $q^0_{Zn}$, $q^1_{Ni}$, $q^1_{Co}$, and $q^1_{Si}$ each ranges from 0 to 0.4 and wherein sum of $q^0_{Zn}$, $q^1_{Ni}$, $q^1_{Co}$, and $q^1_{Si}$ ranges from 0.2 to 0.4.

6. The multicomponent iron catalyst of claim 1, wherein $Q^0$ is Zn, and $Q^1$ is Ni, wherein $q^0_{Zn}$ is equal or larger than $q^1_{Ni}$, wherein $q^0_{Zn}$, and $q^1_{Ni}$ each ranges from 0 to 0.4 and wherein sum of $q^0_{Zn}$ and $q^1_{Ni}$ ranges from 0.2 to 0.4.

7. The multicomponent iron catalyst of claim 1, wherein the third layer of the iron crystal or iron film is deposited on a substrate comprising a base layer consisting of three layers of iron atoms.

8. A multicomponent iron catalyst material comprising a multicomponent iron catalyst for synthesis of ammonia from $N_2$ and $H_2$ according to claim 1 wherein the third layer of the iron crystal or iron film is deposited on a substrate comprising a base layer consisting of three layers of iron atoms, and wherein the substrate is anchored on a solid support for a catalysis process.

9. The multicomponent catalyst of claim 1, wherein $Q_0$ is selected from Zn, Pd, Rh and Cu.

10. The multicomponent catalyst of claim 1, wherein $Q_0$ is Zn.

11. The multicomponent catalyst of claim 10, wherein $q^0_{Zn}$ ranges from 0.2 to 0.4.

12. The multicomponent catalyst of claim 1, wherein $Q_1$ is Si.

13. The multicomponent catalyst of claim 12, wherein, $q^1_{Si}$ is greater than 0.2 and less than or equal to 0.4.

14. The multicomponent catalyst of claim 12, wherein $q^1_{Si}$ is greater than 0.2 and less than or equal to 0.3.

15. The multicomponent catalyst of claim 12, wherein $q^1_{Si}$ is greater than 0.22 and less than or equal to 0.28.

16. The multicomponent catalyst of claim 12, wherein $q^1_{Si}$ is greater than 0.24 and less than or equal to 0.26.

17. The multicomponent catalyst of claim 1, wherein $Q_2$ is Ga.

18. The multicomponent catalyst of claim 1, wherein Qo is Zn, $Q_1$ is Si, and $Q_2$ is Ga.

19. A method for synthesis of ammonia from $N_2$ and $H_2$, the method comprising contacting $N_2$ and $H_2$ with the multicomponent iron catalyst according to claim 1 and/or a multicomponent iron catalyst material comprising the multicomponent iron catalyst according to claim 8 under a temperature 150 to 450° C. to produce ammonia.

* * * * *